(12) United States Patent
Rader et al.

(10) Patent No.: US 11,197,934 B2
(45) Date of Patent: Dec. 14, 2021

(54) DUAL VARIABLE DOMAIN IMMUNOCONJUGATES AND USES THEREOF

(71) Applicant: THE SCRIPPS RESEARCH INSTITUTE, La Jolla, CA (US)

(72) Inventors: Christoph Rader, Jupiter, FL (US); Alex Nanna, Jupiter, FL (US); William Roush, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 292 days.

(21) Appl. No.: 15/760,316

(22) PCT Filed: Sep. 16, 2016

(86) PCT No.: PCT/US2016/052214
§ 371 (c)(1),
(2) Date: Mar. 15, 2018

(87) PCT Pub. No.: WO2017/049139
PCT Pub. Date: Mar. 23, 2017

(65) Prior Publication Data
US 2018/0250415 A1  Sep. 6, 2018

Related U.S. Application Data

(60) Provisional application No. 62/327,849, filed on Apr. 26, 2016, provisional application No. 62/220,148, filed on Sep. 17, 2015.

(51) Int. Cl.
| | |
|---|---|
| *A61K 47/68* | (2017.01) |
| *C07K 16/28* | (2006.01) |
| *C07K 16/32* | (2006.01) |
| *A61K 39/00* | (2006.01) |
| *A61P 35/00* | (2006.01) |
| *A61K 45/06* | (2006.01) |

(52) U.S. Cl.
CPC ...... *A61K 47/6803* (2017.08); *A61K 47/6849* (2017.08); *A61K 47/6851* (2017.08); *A61K 47/6855* (2017.08); *C07K 16/28* (2013.01); *C07K 16/2896* (2013.01); *C07K 16/32* (2013.01); *A61K 45/06* (2013.01); *A61K 2039/505* (2013.01); *A61P 35/00* (2018.01); *C07K 2317/35* (2013.01); *C07K 2317/55* (2013.01); *C07K 2317/60* (2013.01); *C07K 2317/73* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 2003/0175921 | A1* | 9/2003 | Barbas | C07K 14/005 506/9 |
| 2006/0205670 | A1* | 9/2006 | Bradshaw | A61P 35/00 514/13.3 |
| 2009/0215992 | A1* | 8/2009 | Wu | C07K 16/245 530/387.3 |
| 2011/0091463 | A1* | 4/2011 | Ghayur | C07K 16/00 424/136.1 |

FOREIGN PATENT DOCUMENTS

WO   WO 2014/028865   *   2/2014   .......... G01N 33/563

OTHER PUBLICATIONS

Mariuzza (Annu. Rev. Biophys. Biophys. Chem., 16: 139-159, 1987).*

* cited by examiner

*Primary Examiner* — Nelson B Moseley, II
(74) *Attorney, Agent, or Firm* — Hugh Wang; Thomas Fitting

(57) ABSTRACT

Dual variable domain (DVD) immunoconjugates and uses thereof are provided. Aspects of the subject immunoconjugates include a DVD immunoglobulin molecule having a first and a second variable domain, and a cargo moiety (e.g., a drug moiety) that is covalently conjugated to the second variable domain via a linker. Methods of making and using the subject immunoconjugates in the prevention and/or treatment of cancer and other diseases are also provided.

21 Claims, 65 Drawing Sheets

Specification includes a Sequence Listing.

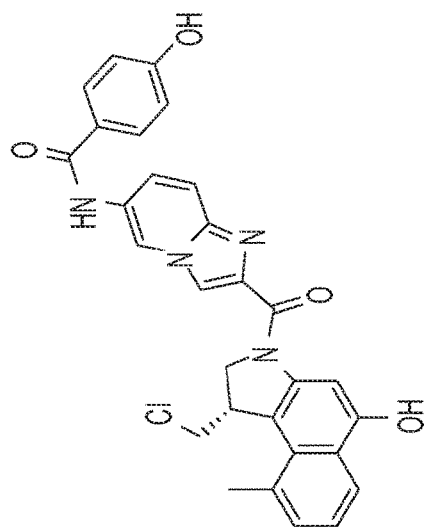
DUOCARMYCINS
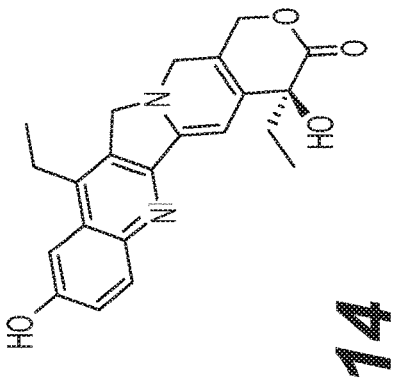
CAMPTOTHECINS (SN-38 SHOWN)
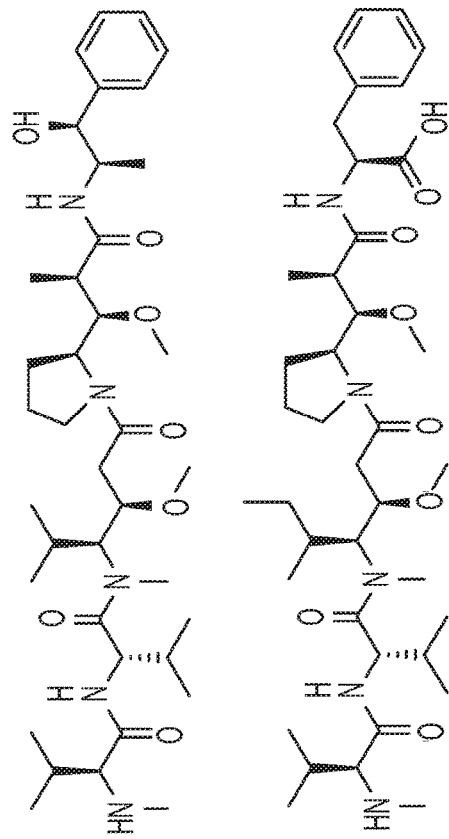
MMAE AND MMAF
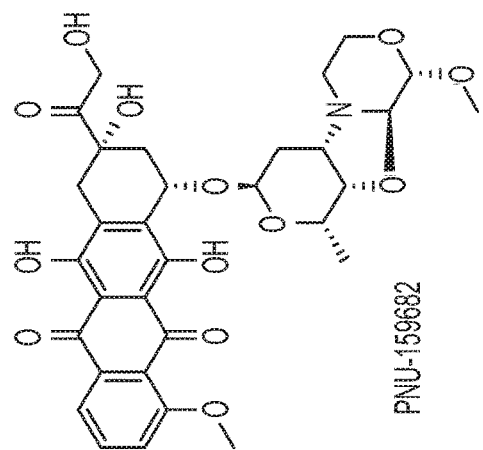
PNU-159682
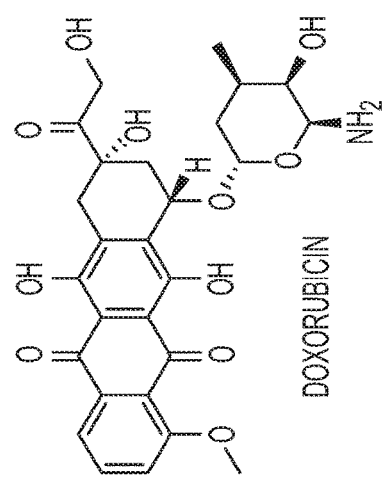
DOXORUBICIN
FIG. 14

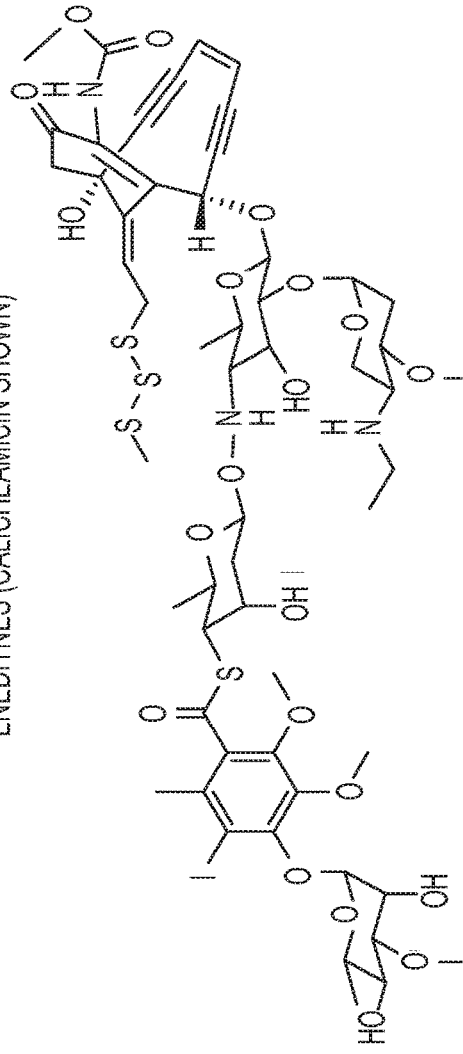
ENEDIYNES (CALICHEAMICIN SHOWN)
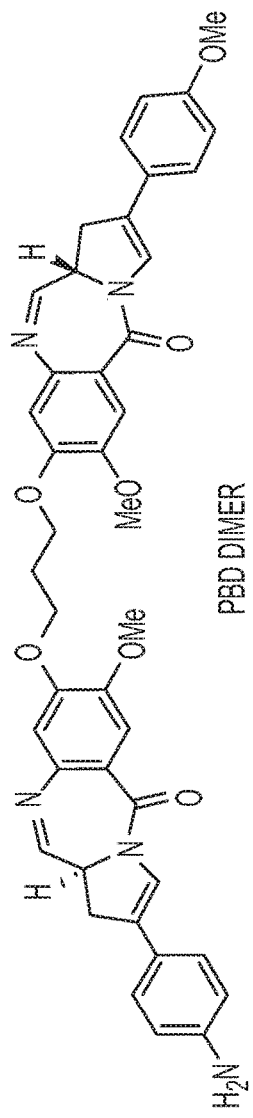
PBD DIMER
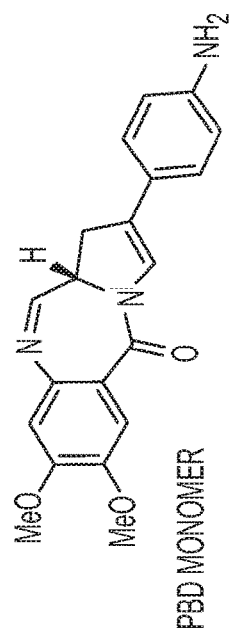
PBD MONOMER
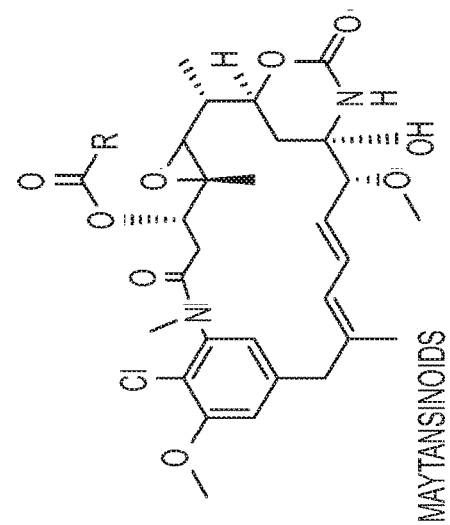
MAYTANSINOIDS
FIG. 14 (CONT.)

β-Lactam-HYDROCARBON LINKER-MMAF

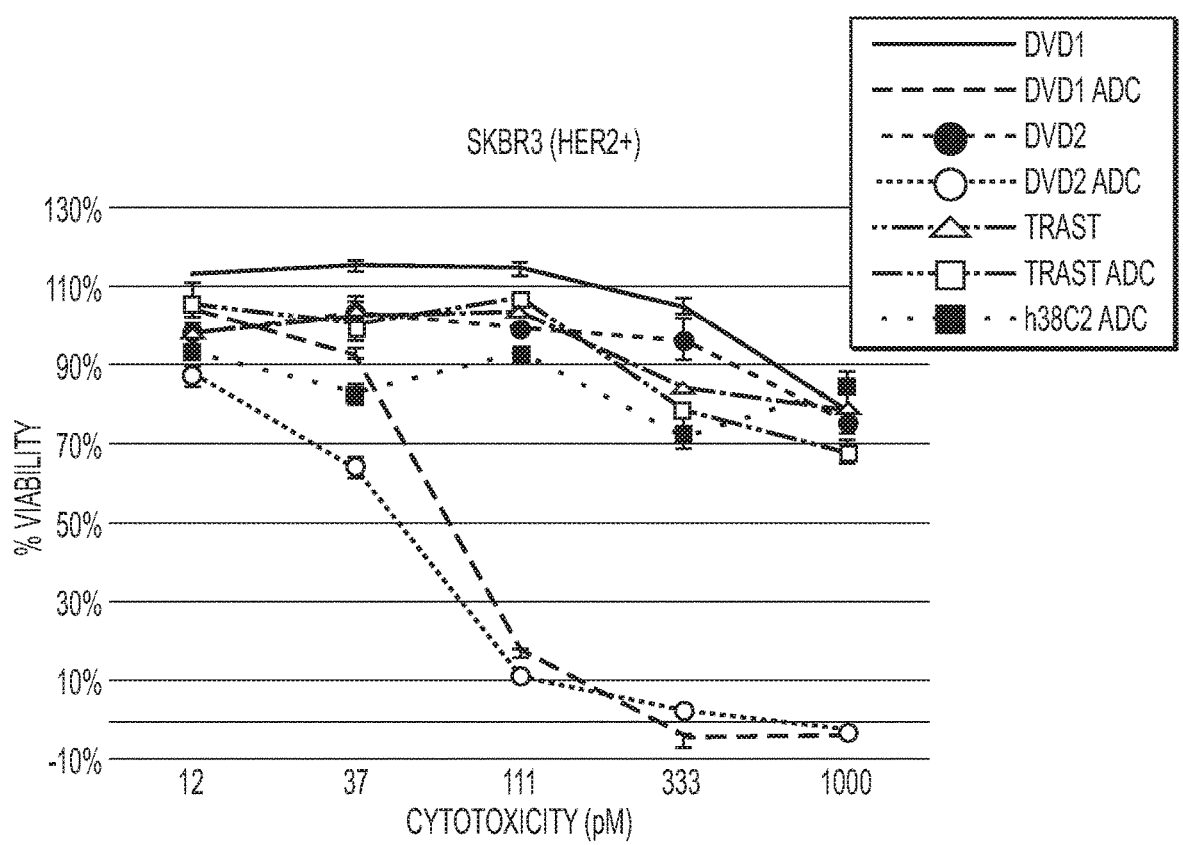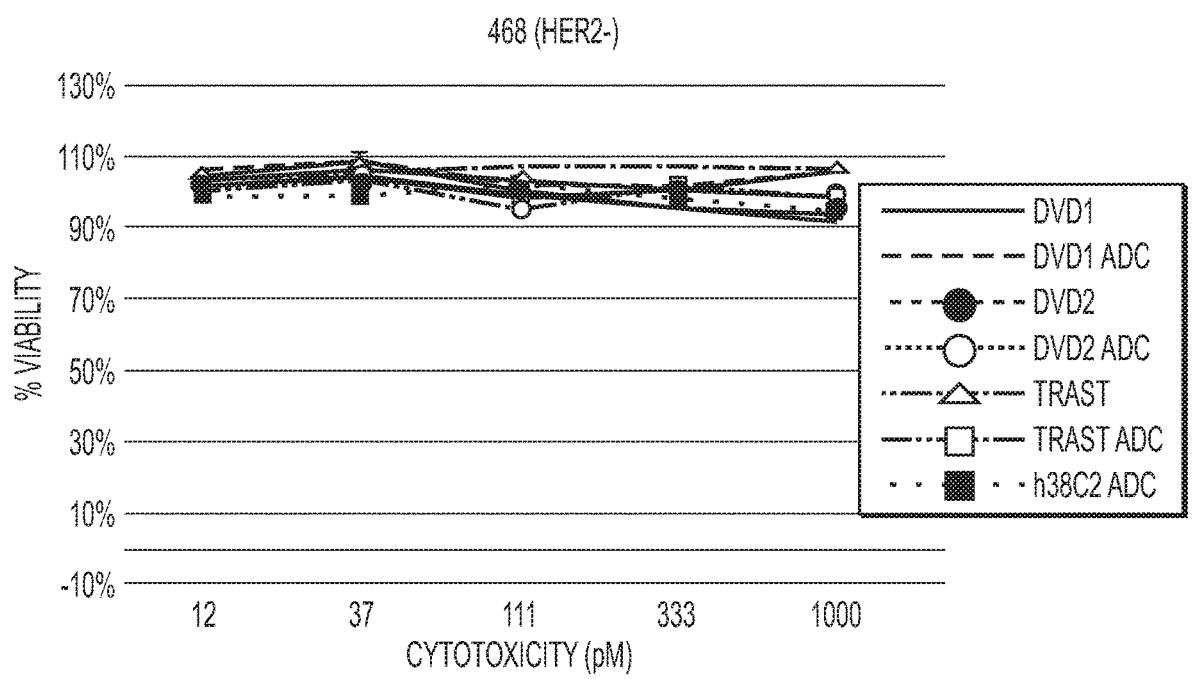
FIG. 20

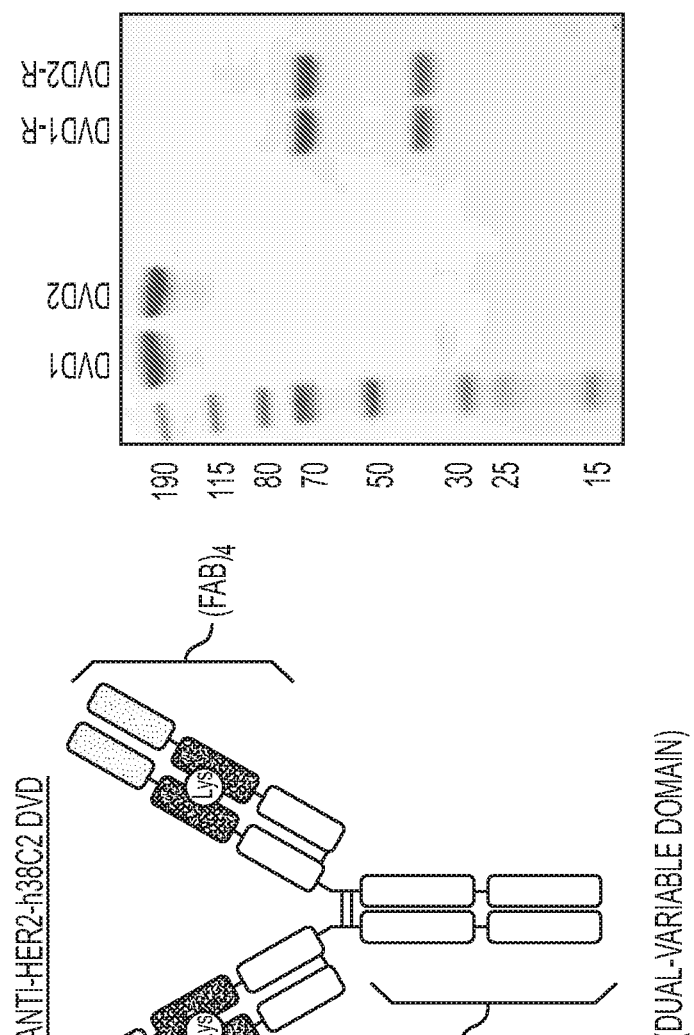
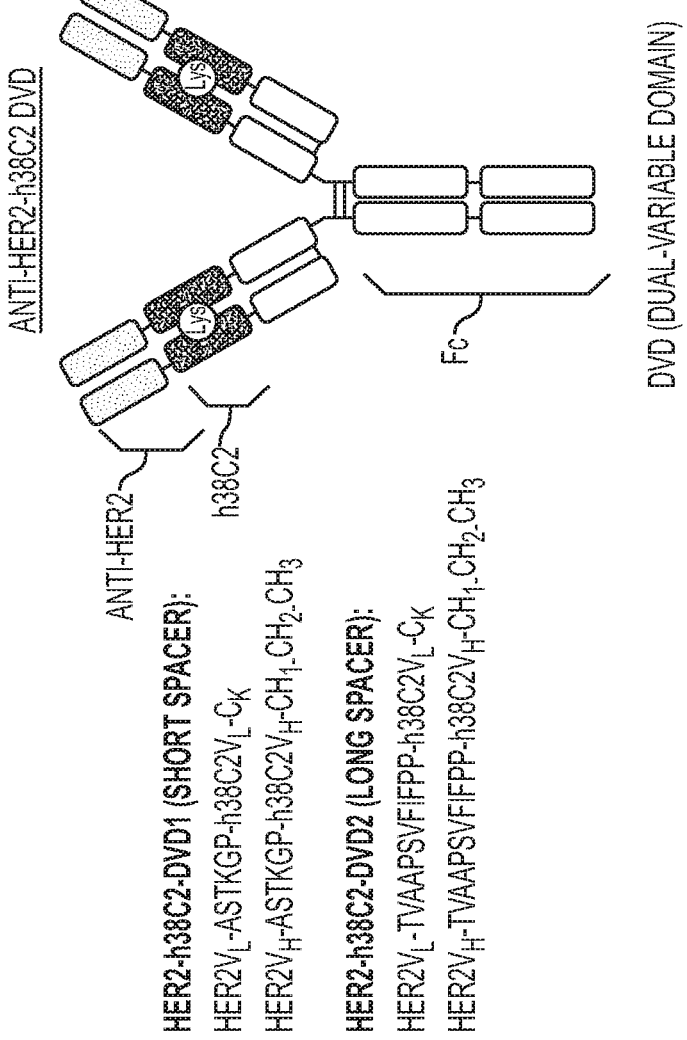
FIG. 21

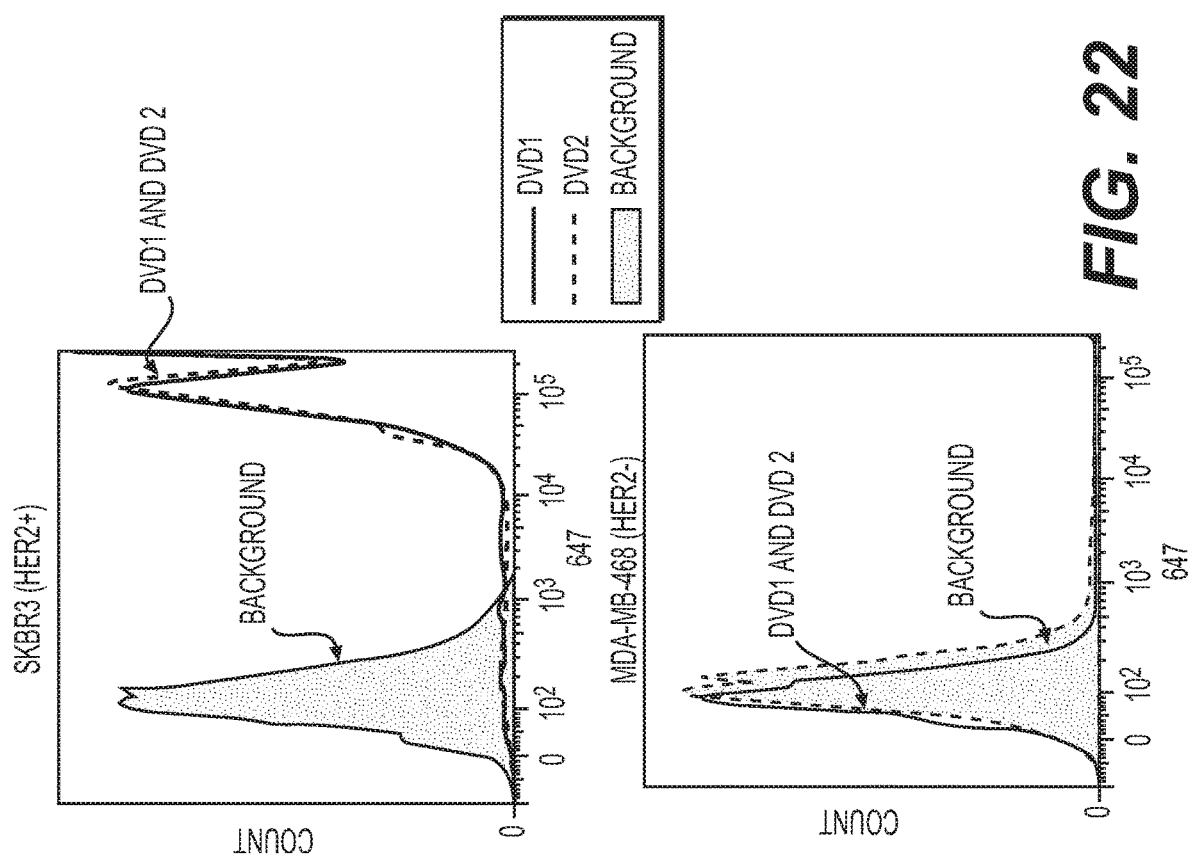
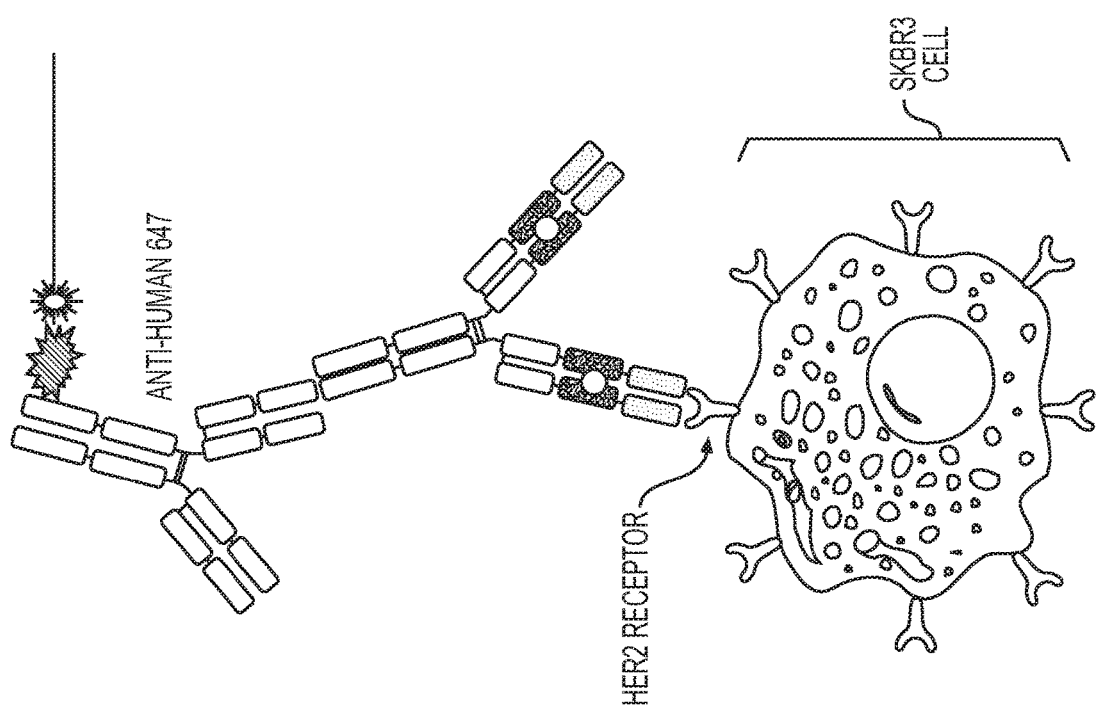
FIG. 22

BIOTIN β-LACTAM (CONT. 1)

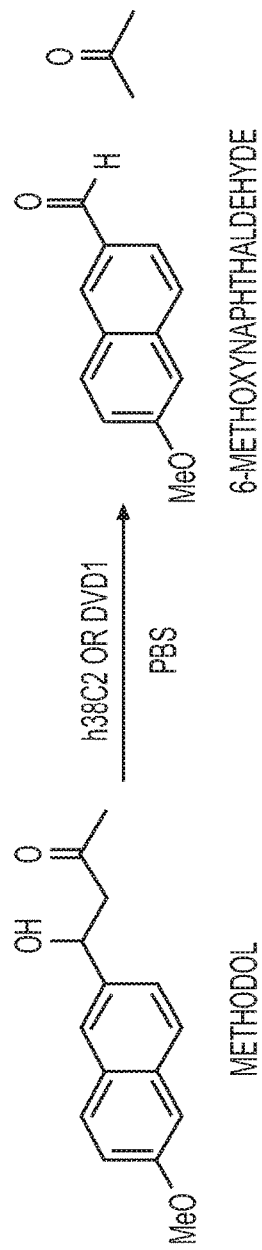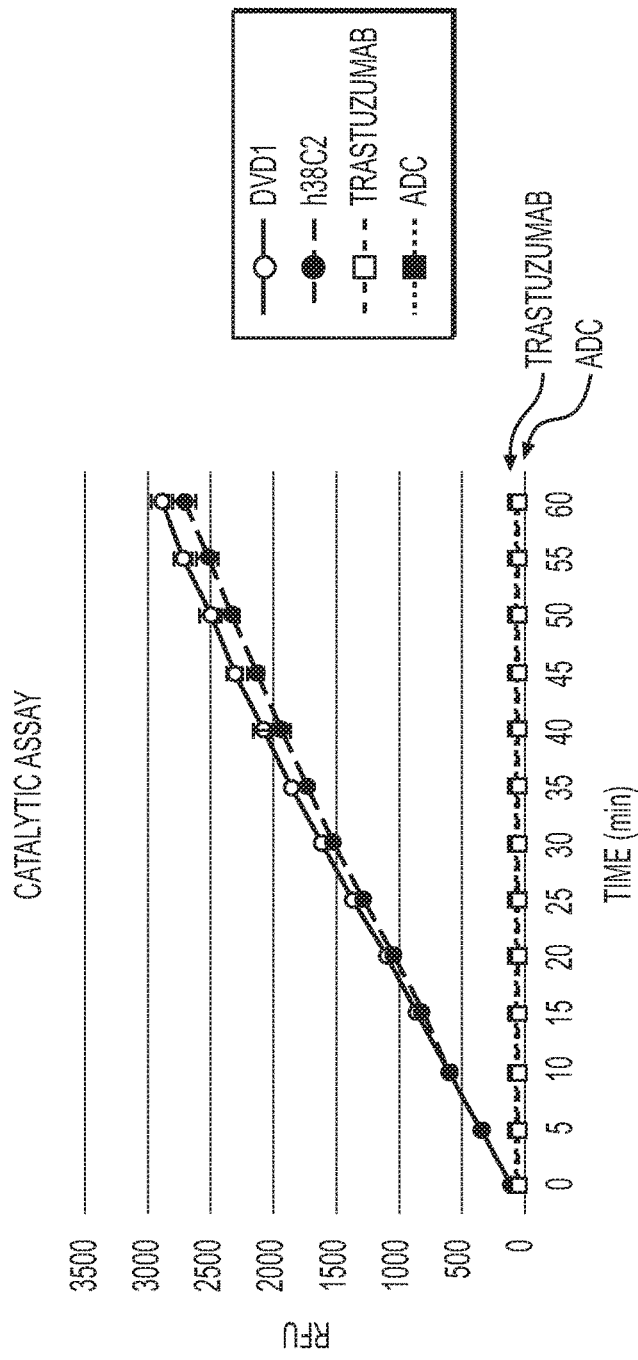
FIG. 28

(CONT. 1)

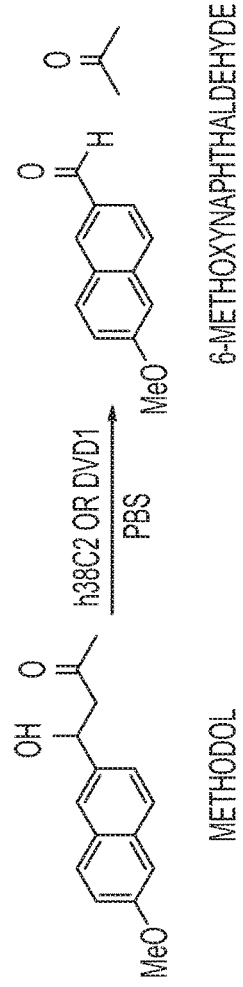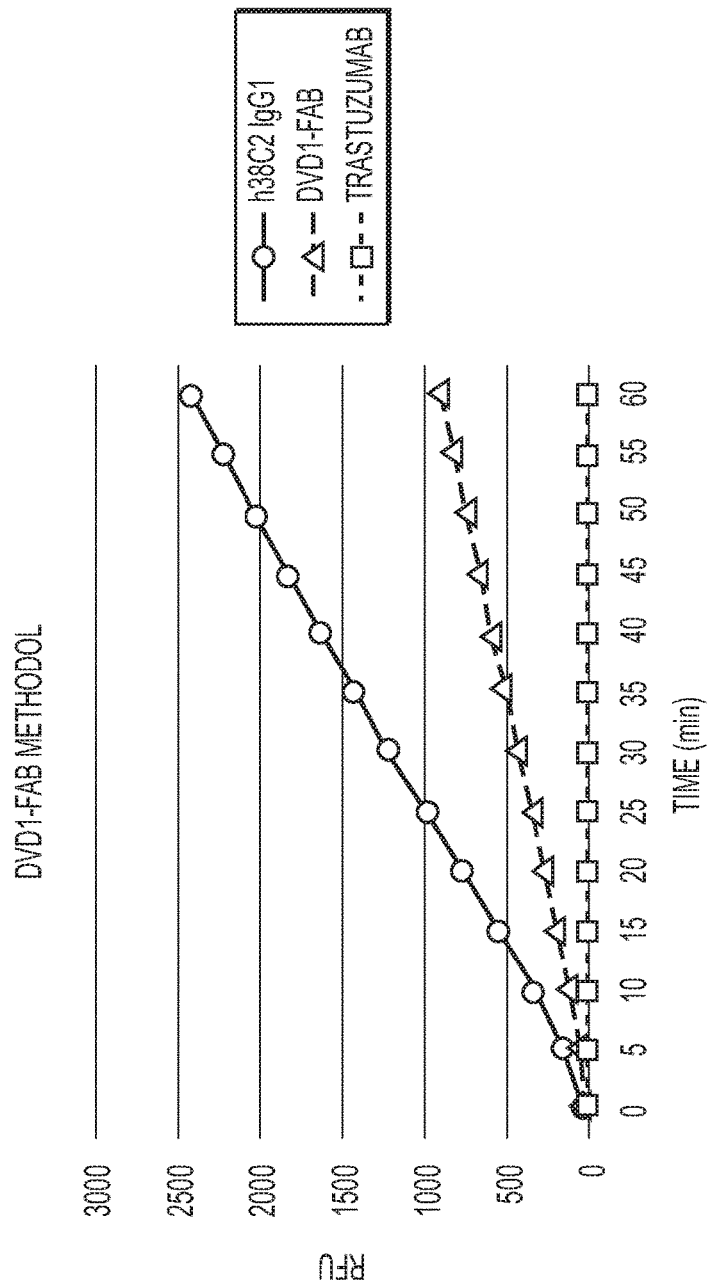
FIG. 32 (CONT.)

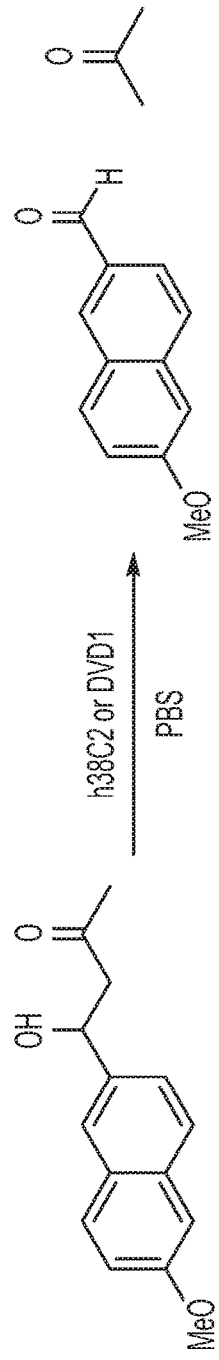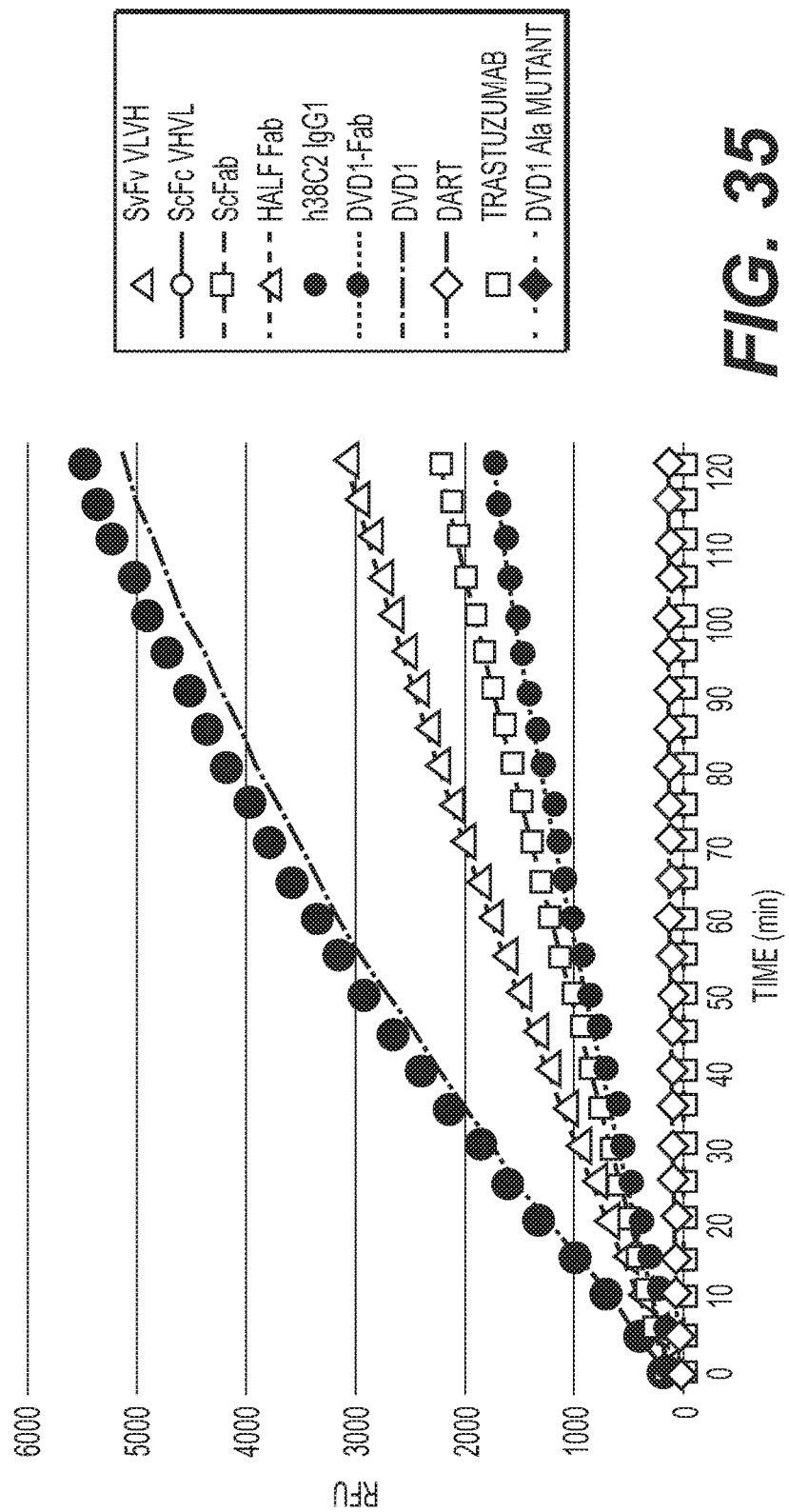
FIG. 35

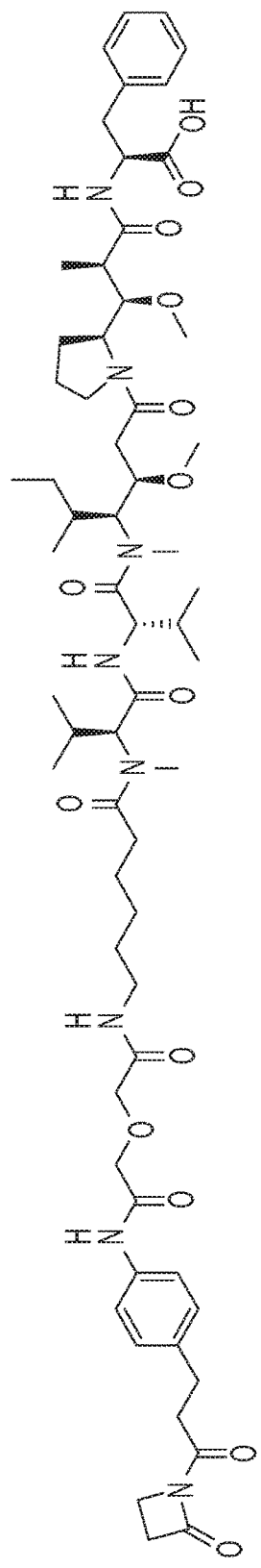
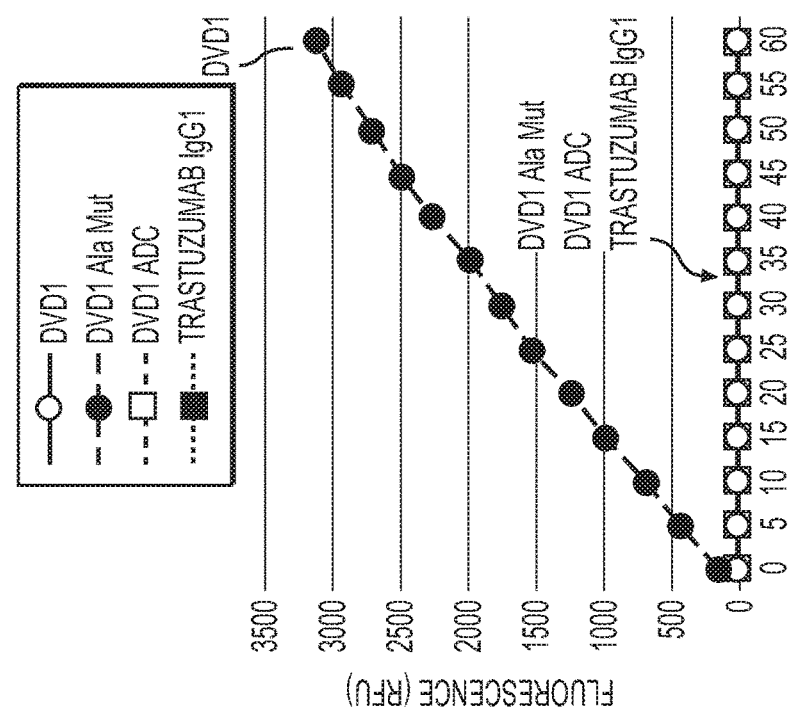
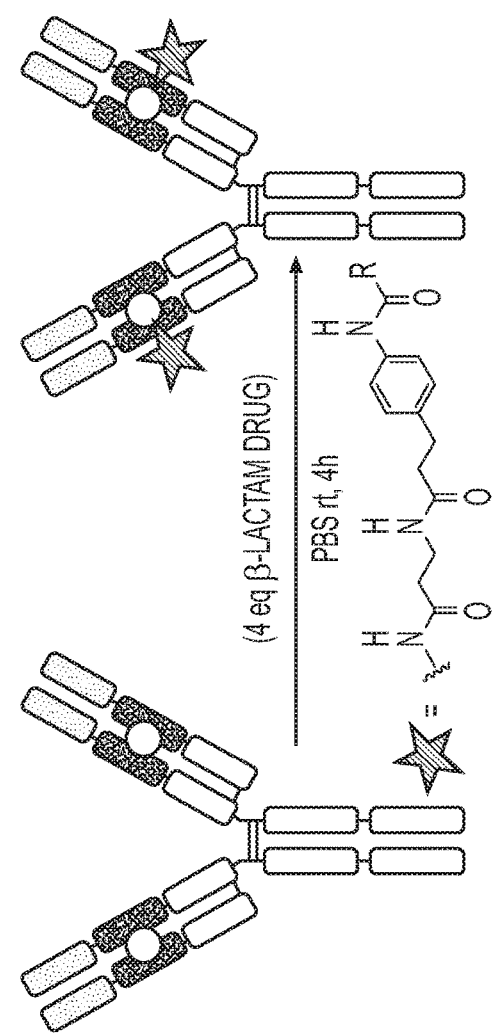
FIG. 37A
FIG. 37B
FIG. 37C

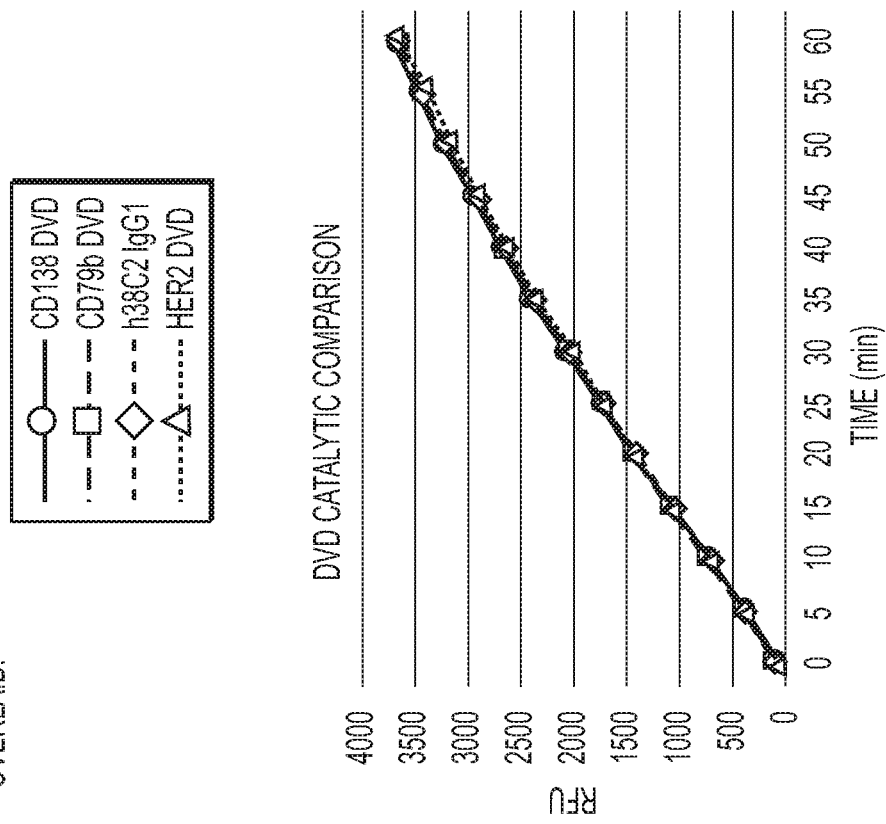
FIG. 45 (CONT. 1)

SEQUENCE LISTING

<160> NUMBER OF SEQ ID NOS: 24

<210> SEQ ID NO 1
<211> LENGTH: 6
<212> TYPE: PRT
<213> ORGANISM: Artificial Sequence

```
<220> FEATURE:
<223> OTHER INFORMATION: Description of Artificial Sequence: Synthetic
      linker peptide

<400> SEQUENCE: 1

Ala Ser Thr Lys Gly Pro
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 2

Thr Val Ala Ala Pro Ser Val Phe Ile Phe Pro Pro
1               5                   10

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      light chain variable region of a humanized 38C2 (h38C2)
      antibody

<400> SEQUENCE: 3

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      heavy chain variable region of a humanized 38C2 (h38C2)
      antibody

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60
```

```
Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Gly Ile Tyr
                 85                  90                  95

Tyr Cys Lys Thr Tyr Phe Tyr Ser Phe Ser Tyr Trp Gly Gln Gly Thr
            100                 105                 110

Leu Val Thr Val Ser Ser
        115

<210> SEQ ID NO 5
<211> LENGTH: 332
<212> TYPE: PRT
<213> ORGANISM: Artificial Sequence
<220> FEATURE:
<223> OTHER INFORMATION: Description of Artificial Sequence: Synthetic
      light chain variable region of an HER2-h38C2-DVD1
      immunoglobulin polypeptide

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Ala Ser Thr Lys Gly
            100                 105                 110

Pro Glu Leu Gln Met Thr Gln Ser Pro Ser Ser Leu Ser Ala Ser Val
        115                 120                 125

Gly Asp Arg Val Thr Ile Thr Cys Arg Ser Ser Gln Ser Leu Leu His
    130                 135                 140

Thr Tyr Gly Ser Pro Tyr Leu Asn Trp Tyr Leu Gln Lys Pro Gly Gln
145                 150                 155                 160

Ser Pro Lys Leu Leu Ile Tyr Lys Val Ser Asn Arg Phe Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Val Tyr Phe Cys Ser Gln
        195                 200                 205

Gly Thr His Leu Pro Tyr Thr Phe Gly Gly Gly Thr Lys Val Glu Ile
    210                 215                 220

Lys Arg Thr Val Ala Ala Pro Ser Val Phe Ile Phe Pro Pro Ser Asp
225                 230                 235                 240

Glu Gln Leu Lys Ser Gly Thr Ala Ser Val Val Cys Leu Leu Asn Asn
                245                 250                 255

Phe Tyr Pro Arg Glu Ala Lys Val Gln Trp Lys Val Asp Asn Ala Leu
            260                 265                 270

Gln Ser Gly Asn Ser Gln Glu Ser Val Thr Glu Gln Asp Ser Lys Asp
        275                 280                 285
```

-continued

```
Ser Thr Tyr Ser Leu Ser Ser Thr Leu Thr Leu Ser Lys Ala Asp Tyr
    290                 295                 300

Glu Lys His Lys Val Tyr Ala Cys Glu Val Thr His Gln Gly Leu Ser
305                 310                 315                 320

Ser Pro Val Thr Lys Ser Phe Asn Arg Gly Glu Cys
            325                 330

<210> SEQ ID NO 6
<211> LENGTH: 574
<212> TYPE: PRT
<213> ORGANISM: Artificial Sequence
<220> FEATURE:
<223> OTHER INFORMATION: Description of Artificial Sequence: Synthetic
      heavy chain variable region of an HER2-h38C2-DVD1
      immunoglobulin polypeptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Asn Tyr Trp Met
145                 150                 155                 160

Ser Trp Val Arg Gln Ser Pro Glu Lys Gly Leu Glu Trp Val Ser Glu
                165                 170                 175

Ile Arg Leu Arg Ser Asp Asn Tyr Ala Thr His Tyr Ala Glu Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Gly Ile Tyr Tyr Cys
    210                 215                 220

Lys Thr Tyr Phe Tyr Ser Phe Ser Tyr Trp Gly Gln Gly Thr Leu Val
225                 230                 235                 240

Thr Val Ser Ser Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
```

-continued

```
                305                 310                 315                 320
Gly Thr Gln Thr Tyr Ile Cys Asn Val Asn His Lys Pro Ser Asn Thr
                325                 330                 335
Lys Val Asp Lys Arg Val Glu Pro Lys Ser Cys Asp Lys Thr His Thr
                340                 345                 350
Cys Pro Pro Cys Pro Ala Pro Glu Leu Leu Gly Gly Pro Ser Val Phe
                355                 360                 365
Leu Phe Pro Pro Lys Pro Lys Asp Thr Leu Met Ile Ser Arg Thr Pro
370                 375                 380
Glu Val Thr Cys Val Val Val Asp Val Ser His Glu Asp Pro Glu Val
385                 390                 395                 400
Lys Phe Asn Trp Tyr Val Asp Gly Val Glu Val His Asn Ala Lys Thr
                405                 410                 415
Lys Pro Arg Glu Glu Gln Tyr Asn Ser Thr Tyr Arg Val Val Ser Val
                420                 425                 430
Leu Thr Val Leu His Gln Asp Trp Leu Asn Gly Lys Glu Tyr Lys Cys
                435                 440                 445
Lys Val Ser Asn Lys Ala Leu Pro Ala Pro Ile Glu Lys Thr Ile Ser
                450                 455                 460
Lys Ala Lys Gly Gln Pro Arg Glu Pro Gln Val Tyr Thr Leu Pro Pro
465                 470                 475                 480
Ser Arg Glu Glu Met Thr Lys Asn Gln Val Ser Leu Thr Cys Leu Val
                485                 490                 495
Lys Gly Phe Tyr Pro Ser Asp Ile Ala Val Glu Trp Glu Ser Asn Gly
                500                 505                 510
Gln Pro Glu Asn Asn Tyr Lys Thr Thr Pro Pro Val Leu Asp Ser Asp
                515                 520                 525
Gly Ser Phe Phe Leu Tyr Ser Lys Leu Thr Val Asp Lys Ser Arg Trp
                530                 535                 540
Gln Gln Gly Asn Val Phe Ser Cys Ser Val Met His Glu Ala Leu His
545                 550                 555                 560
Asn His Tyr Thr Gln Lys Ser Leu Ser Leu Ser Pro Gly Lys
                565                 570
```

<210> SEQ ID NO 7
<211> LENGTH: 338
<212> TYPE: PRT
<213> ORGANISM: Artificial Sequence
<220> FEATURE:
<223> OTHER INFORMATION: Description of Artificial Sequence: Synthetic
      light chain variable region of an HER2-h38C2-DVD2
      immunoglobulin polypeptide

<400> SEQUENCE: 7

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
```

Thr Phe Gly Gln Gly Thr Lys Val Glu Ile Lys Thr Val Ala Ala Pro
            100                 105                 110

Ser Val Phe Ile Phe Pro Pro Glu Leu Gln Met Thr Gln Ser Pro Ser
            115                 120                 125

Ser Leu Ser Ala Ser Val Gly Asp Arg Val Thr Ile Thr Cys Arg Ser
            130                 135                 140

Ser Gln Ser Leu Leu His Thr Tyr Gly Ser Pro Tyr Leu Asn Trp Tyr
145                 150                 155                 160

Leu Gln Lys Pro Gly Gln Ser Pro Lys Leu Leu Ile Tyr Lys Val Ser
                165                 170                 175

Asn Arg Phe Ser Gly Val Pro Ser Arg Phe Ser Gly Ser Gly Ser Gly
                180                 185                 190

Thr Asp Phe Thr Leu Thr Ile Ser Ser Leu Gln Pro Glu Asp Phe Ala
                195                 200                 205

Val Tyr Phe Cys Ser Gln Gly Thr His Leu Pro Tyr Thr Phe Gly Gly
            210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
                275                 280                 285

Glu Gln Asp Ser Lys Asp Ser Thr Tyr Ser Leu Ser Ser Thr Leu Thr
            290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 8
<211> LENGTH: 580
<212> TYPE: PRT
<213> ORGANISM: Artificial Sequence
<220> FEATURE:
<223> OTHER INFORMATION: Description of Artificial Sequence: Synthetic
      heavy chain variable region of an HER2-h38C2-DVD2
      immunoglobulin polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln

```
              100                 105                 110
Gly Thr Leu Val Thr Val Ser Ser Thr Val Ala Ala Pro Ser Val Phe
              115                 120                 125
Ile Phe Pro Pro Glu Val Gln Leu Val Glu Ser Gly Gly Gly Leu Val
              130                 135                 140
Gln Pro Gly Gly Ser Leu Arg Leu Ser Cys Ala Ala Ser Gly Phe Thr
145                 150                 155                 160
Phe Ser Asn Tyr Trp Met Ser Trp Val Arg Gln Ser Pro Glu Lys Gly
              165                 170                 175
Leu Glu Trp Val Ser Glu Ile Arg Leu Arg Ser Asp Asn Tyr Ala Thr
              180                 185                 190
His Tyr Ala Glu Ser Val Lys Gly Arg Phe Thr Ile Ser Arg Asp Asn
              195                 200                 205
Ser Lys Asn Thr Leu Tyr Leu Gln Met Asn Ser Leu Arg Ala Glu Asp
              210                 215                 220
Thr Gly Ile Tyr Tyr Cys Lys Thr Tyr Phe Tyr Ser Phe Ser Tyr Trp
225                 230                 235                 240
Gly Gln Gly Thr Leu Val Thr Val Ser Ser Ala Ser Thr Lys Gly Pro
              245                 250                 255
Ser Val Phe Pro Leu Ala Pro Ser Ser Lys Ser Thr Ser Gly Gly Thr
              260                 265                 270
Ala Ala Leu Gly Cys Leu Val Lys Asp Tyr Phe Pro Glu Pro Val Thr
              275                 280                 285
Val Ser Trp Asn Ser Gly Ala Leu Thr Ser Gly Val His Thr Phe Pro
              290                 295                 300
Ala Val Leu Gln Ser Ser Gly Leu Tyr Ser Leu Ser Ser Val Val Thr
305                 310                 315                 320
Val Pro Ser Ser Ser Leu Gly Thr Gln Thr Tyr Ile Cys Asn Val Asn
              325                 330                 335
His Lys Pro Ser Asn Thr Lys Val Asp Lys Arg Val Glu Pro Lys Ser
              340                 345                 350
Cys Asp Lys Thr His Thr Cys Pro Pro Cys Pro Ala Pro Glu Leu Leu
              355                 360                 365
Gly Gly Pro Ser Val Phe Leu Phe Pro Pro Lys Pro Lys Asp Thr Leu
              370                 375                 380
Met Ile Ser Arg Thr Pro Glu Val Thr Cys Val Val Val Asp Val Ser
385                 390                 395                 400
His Glu Asp Pro Glu Val Lys Phe Asn Trp Tyr Val Asp Gly Val Glu
              405                 410                 415
Val His Asn Ala Lys Thr Lys Pro Arg Glu Glu Gln Tyr Asn Ser Thr
              420                 425                 430
Tyr Arg Val Val Ser Val Leu Thr Val Leu His Gln Asp Trp Leu Asn
              435                 440                 445
Gly Lys Glu Tyr Lys Cys Lys Val Ser Asn Lys Ala Leu Pro Ala Pro
              450                 455                 460
Ile Glu Lys Thr Ile Ser Lys Ala Lys Gly Gln Pro Arg Glu Pro Gln
465                 470                 475                 480
Val Tyr Thr Leu Pro Pro Ser Arg Glu Glu Met Thr Lys Asn Gln Val
              485                 490                 495
Ser Leu Thr Cys Leu Val Lys Gly Phe Tyr Pro Ser Asp Ile Ala Val
              500                 505                 510
Glu Trp Glu Ser Asn Gly Gln Pro Glu Asn Asn Tyr Lys Thr Thr Pro
              515                 520                 525
```

```
Pro Val Leu Asp Ser Asp Gly Ser Phe Phe Leu Tyr Ser Lys Leu Thr
        530                 535                 540
Val Asp Lys Ser Arg Trp Gln Gln Gly Asn Val Phe Ser Cys Ser Val
545                 550                 555                 560
Met His Glu Ala Leu His Asn His Tyr Thr Gln Lys Ser Leu Ser Leu
                565                 570                 575
Ser Pro Gly Lys
        580

<210> SEQ ID NO 9
<211> LENGTH: 337
<212> TYPE: PRT
<213> ORGANISM: Artificial Sequence
<220> FEATURE:
<223> OTHER INFORMATION: Description of Artificial Sequence: Synthetic
      light chain variable region of an IMGN-853 FOLR1-h38C2-DVD1
      immunoglobulin polypeptide

<400> SEQUENCE: 9

Asp Ile Val Leu Thr Gln Ser Pro Leu Ser Leu Ala Val Ser Leu Gly
1               5                   10                  15
Gln Pro Ala Ile Ile Ser Cys Lys Ala Ser Gln Ser Val Ser Phe Ala
            20                  25                  30
Gly Thr Ser Leu Met His Trp Tyr His Gln Lys Pro Gly Gln Gln Pro
        35                  40                  45
Arg Leu Leu Ile Tyr Arg Ala Ser Asn Leu Glu Ala Gly Val Pro Asp
    50                  55                  60
Arg Phe Ser Gly Ser Gly Ser Lys Thr Asp Phe Thr Leu Asn Ile Ser
65                  70                  75                  80
Pro Val Glu Ala Glu Asp Ala Ala Thr Tyr Tyr Cys Gln Gln Ser Arg
                85                  90                  95
Glu Tyr Pro Tyr Thr Phe Gly Gly Thr Lys Leu Glu Ile Lys Arg
            100                 105                 110
Ala Ser Thr Lys Gly Pro Glu Leu Gln Met Thr Gln Ser Pro Ser Ser
        115                 120                 125
Leu Ser Ala Ser Val Gly Asp Arg Val Thr Ile Thr Cys Arg Ser Ser
    130                 135                 140
Gln Ser Leu Leu His Thr Tyr Gly Ser Pro Tyr Leu Asn Trp Tyr Leu
145                 150                 155                 160
Gln Lys Pro Gly Gln Ser Pro Lys Leu Leu Ile Tyr Lys Val Ser Asn
                165                 170                 175
Arg Phe Ser Gly Val Pro Ser Arg Phe Ser Gly Ser Gly Ser Gly Thr
            180                 185                 190
Asp Phe Thr Leu Thr Ile Ser Ser Leu Gln Pro Glu Asp Phe Ala Val
        195                 200                 205
Tyr Phe Cys Ser Gln Gly Thr His Leu Pro Tyr Thr Phe Gly Gly Gly
    210                 215                 220
Thr Lys Val Glu Ile Lys Arg Thr Val Ala Ala Pro Ser Val Phe Ile
225                 230                 235                 240
Phe Pro Pro Ser Asp Glu Gln Leu Lys Ser Gly Thr Ala Ser Val Val
                245                 250                 255
Cys Leu Leu Asn Asn Phe Tyr Pro Arg Glu Ala Lys Val Gln Trp Lys
            260                 265                 270
Val Asp Asn Ala Leu Gln Ser Gly Asn Ser Gln Glu Ser Val Thr Glu
        275                 280                 285
```

```
Gln Asp Ser Lys Asp Ser Thr Tyr Ser Leu Ser Ser Thr Leu Thr Leu
            290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
            325                 330                 335

Cys
```

<210> SEQ ID NO 10
<211> LENGTH: 572
<212> TYPE: PRT
<213> ORGANISM: Artificial Sequence
<220> FEATURE:
<223> OTHER INFORMATION: Description of Artificial Sequence: Synthetic
      heavy chain variable region of an IMGN-853 FOLR1-h38C2-DVD1
      immunoglobulin polypeptide

<400> SEQUENCE: 10

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Ser Asn Tyr Trp Met Ser Trp
145                 150                 155                 160

Val Arg Gln Ser Pro Glu Lys Gly Leu Glu Trp Val Ser Glu Ile Arg
                165                 170                 175

Leu Arg Ser Asp Asn Tyr Ala Thr His Tyr Ala Glu Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Gly Ile Tyr Tyr Cys Lys Thr
    210                 215                 220

Tyr Phe Tyr Ser Phe Ser Tyr Trp Gly Gln Gly Thr Leu Val Thr Val
225                 230                 235                 240

Ser Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300
```

```
Tyr Ser Leu Ser Ser Val Val Thr Val Pro Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
        340                 345                 350

Pro Cys Pro Ala Pro Glu Leu Leu Gly Gly Pro Ser Val Phe Leu Phe
    355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 11
<211> LENGTH: 343
<212> TYPE: PRT
<213> ORGANISM: Artificial Sequence
<220> FEATURE:
<223> OTHER INFORMATION: Description of Artificial Sequence: Synthetic
      light chain variable region of an IMGN-853 FOLR1-h38C2-DVD2
      immunoglobulin polypeptide

<400> SEQUENCE: 11

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80
```

```
Pro Val Glu Ala Glu Asp Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Glu Leu Gln Met
        115                 120                 125

Thr Gln Ser Pro Ser Ser Leu Ser Ala Ser Val Gly Asp Arg Val Thr
    130                 135                 140

Ile Thr Cys Arg Ser Ser Gln Ser Leu Leu His Thr Tyr Gly Ser Pro
145                 150                 155                 160

Tyr Leu Asn Trp Tyr Leu Gln Lys Pro Gly Gln Ser Pro Lys Leu Leu
                165                 170                 175

Ile Tyr Lys Val Ser Asn Arg Phe Ser Gly Val Pro Ser Arg Phe Ser
            180                 185                 190

Gly Ser Gly Ser Gly Thr Asp Phe Thr Leu Thr Ile Ser Ser Leu Gln
        195                 200                 205

Pro Glu Asp Phe Ala Val Tyr Phe Cys Ser Gln Gly Thr His Leu Pro
    210                 215                 220

Tyr Thr Phe Gly Gly Gly Thr Lys Val Glu Ile Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
    290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
                340

<210> SEQ ID NO 12
<211> LENGTH: 578
<212> TYPE: PRT
<213> ORGANISM: Artificial Sequence
<220> FEATURE:
<223> OTHER INFORMATION: Description of Artificial Sequence: Synthetic
      heavy chain variable region of an IMGN-853 FOLR1-h38C2-DVD2
      immunoglobulin polypeptide

<400> SEQUENCE: 12

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
```

-continued

```
                85                  90                  95
Thr Arg Tyr Asp Gly Ser Arg Ala Met Asp Tyr Trp Gln Gly Thr
               100                 105                 110
Thr Val Thr Val Ser Ser Thr Val Ala Ala Pro Ser Val Phe Ile Phe
               115                 120                 125
Pro Pro Glu Val Gln Leu Val Glu Ser Gly Gly Leu Val Gln Pro
               130                 135                 140
Gly Gly Ser Leu Arg Leu Ser Cys Ala Ala Ser Gly Phe Thr Phe Ser
145                 150                 155                 160
Asn Tyr Trp Met Ser Trp Val Arg Gln Ser Pro Glu Lys Gly Leu Glu
                    165                 170                 175
Trp Val Ser Glu Ile Arg Leu Arg Ser Asp Asn Tyr Ala Thr His Tyr
                180                 185                 190
Ala Glu Ser Val Lys Gly Arg Phe Thr Ile Ser Arg Asp Asn Ser Lys
                    195                 200                 205
Asn Thr Leu Tyr Leu Gln Met Asn Ser Leu Arg Ala Glu Asp Thr Gly
                210                 215                 220
Ile Tyr Tyr Cys Lys Thr Tyr Phe Tyr Ser Phe Ser Tyr Trp Gly Gln
225                 230                 235                 240
Gly Thr Leu Val Thr Val Ser Ser Ala Ser Thr Lys Gly Pro Ser Val
                    245                 250                 255
Phe Pro Leu Ala Pro Ser Ser Lys Ser Thr Ser Gly Gly Thr Ala Ala
                260                 265                 270
Leu Gly Cys Leu Val Lys Asp Tyr Phe Pro Glu Pro Val Thr Val Ser
                    275                 280                 285
Trp Asn Ser Gly Ala Leu Thr Ser Gly Val His Thr Phe Pro Ala Val
                290                 295                 300
Leu Gln Ser Ser Gly Leu Tyr Ser Leu Ser Ser Val Val Thr Val Pro
305                 310                 315                 320
Ser Ser Ser Leu Gly Thr Gln Thr Tyr Ile Cys Asn Val Asn His Lys
                    325                 330                 335
Pro Ser Asn Thr Lys Val Asp Lys Arg Val Glu Pro Lys Ser Cys Asp
                340                 345                 350
Lys Thr His Thr Cys Pro Pro Cys Pro Ala Pro Glu Leu Leu Gly Gly
                    355                 360                 365
Pro Ser Val Phe Leu Phe Pro Pro Lys Pro Lys Asp Thr Leu Met Ile
                370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                    405                 410                 415
Asn Ala Lys Thr Lys Pro Arg Glu Glu Gln Tyr Asn Ser Thr Tyr Arg
                420                 425                 430
Val Val Ser Val Leu Thr Val Leu His Gln Asp Trp Leu Asn Gly Lys
                    435                 440                 445
Glu Tyr Lys Cys Lys Val Ser Asn Lys Ala Leu Pro Ala Pro Ile Glu
                450                 455                 460
Lys Thr Ile Ser Lys Ala Lys Gly Gln Pro Arg Glu Pro Gln Val Tyr
465                 470                 475                 480
Thr Leu Pro Pro Ser Arg Glu Glu Met Thr Lys Asn Gln Val Ser Leu
                    485                 490                 495
Thr Cys Leu Val Lys Gly Phe Tyr Pro Ser Asp Ile Ala Val Glu Trp
                500                 505                 510
```

```
Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Lys Leu Thr Val Asp
            530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
            565                 570                 575

Gly Lys

<210> SEQ ID NO 13
<211> LENGTH: 335
<212> TYPE: PRT
<213> ORGANISM: Artificial Sequence
<220> FEATURE:
<223> OTHER INFORMATION: Description of Artificial Sequence: Synthetic
      light chain variable region of a farletuzumab FOLR1-h38C2-DVD1
      immunoglobulin polypeptide

<400> SEQUENCE: 13

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
 50                 55                  60

Gly Ser Gly Ser Gly Thr Asp Tyr Thr Phe Thr Ile Ser Ser Leu Gln
 65                 70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Ala Ser
            100                 105                 110

Thr Lys Gly Pro Glu Leu Gln Met Thr Gln Ser Pro Ser Ser Leu Ser
        115                 120                 125

Ala Ser Val Gly Asp Arg Val Thr Ile Thr Cys Arg Ser Ser Gln Ser
    130                 135                 140

Leu Leu His Thr Tyr Gly Ser Pro Tyr Leu Asn Trp Tyr Leu Gln Lys
145                 150                 155                 160

Pro Gly Gln Ser Pro Lys Leu Leu Ile Tyr Lys Val Ser Asn Arg Phe
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Phe Ala Val Tyr Phe
        195                 200                 205

Cys Ser Gln Gly Thr His Leu Pro Tyr Thr Phe Gly Gly Gly Thr Lys
    210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
```

```
                275                 280                 285
Ser Lys Asp Ser Thr Tyr Ser Leu Ser Ser Thr Leu Thr Leu Ser Lys
        290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 14
<211> LENGTH: 572
<212> TYPE: PRT
<213> ORGANISM: Artificial Sequence
<220> FEATURE:
<223> OTHER INFORMATION: Description of Artificial Sequence: Synthetic
      heavy chain variable region of a farletuzumab FOLR1-h38C2-DVD1
      immunoglobulin polypeptide

<400> SEQUENCE: 14

Glu Val Gln Leu Val Glu Ser Gly Gly Gly Trp Gln Pro Gly Arg Ser
1               5                   10                  15

Leu Arg Leu Ser Cys Ser Ala Ser Gly Phe Thr Phe Ser Gly Tyr Gly
            20                  25                  30

Leu Ser Trp Val Arg Gln Ala Pro Gly Lys Gly Leu Glu Trp Val Ala
        35                  40                  45

Met Ile Ser Ser Gly Gly Ser Tyr Thr Tyr Tyr Ala Asp Ser Val Lys
50                  55                  60

Gly Arg Phe Ala Ile Ser Arg Asp Asn Ala Lys Asn Thr Leu Phe Leu
65                  70                  75                  80

Gln Met Asp Ser Leu Arg Pro Glu Asp Thr Gly Val Tyr Phe Cys Ala
            85                  90                  95

Arg His Gly Asp Asp Pro Ala Trp Phe Ala Tyr Trp Gly Gln Gly Thr
            100                 105                 110

Pro Val Thr Val Ser Ser Ala Ser Thr Lys Gly Pro Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Phe Ser Asn Tyr Trp Met Ser Trp
145                 150                 155                 160

Val Arg Gln Ser Pro Glu Lys Gly Leu Glu Trp Val Ser Glu Ile Arg
                165                 170                 175

Leu Arg Ser Asp Asn Tyr Ala Thr His Tyr Ala Glu Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Gly Ile Tyr Tyr Cys Lys Thr
210                 215                 220

Tyr Phe Tyr Ser Phe Ser Tyr Trp Gly Gln Gly Thr Leu Val Thr Val
225                 230                 235                 240

Ser Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
290                 295                 300
```

Tyr Ser Leu Ser Ser Val Val Thr Val Pro Ser Ser Leu Gly Thr
305                 310                 315                 320

Gln Thr Tyr Ile Cys Asn Val Asn His Lys Pro Ser Asn Thr Lys Val
            325                 330                 335

Asp Lys Arg Val Glu Pro Lys Ser Cys Asp Lys Thr His Thr Cys Pro
        340                 345                 350

Pro Cys Pro Ala Pro Glu Leu Leu Gly Gly Pro Ser Val Phe Leu Phe
    355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
            405                 410                 415

Arg Glu Glu Gln Tyr Asn Ser Thr Tyr Arg Val Val Ser Val Leu Thr
        420                 425                 430

Val Leu His Gln Asp Trp Leu Asn Gly Lys Glu Tyr Lys Cys Lys Val
    435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
            485                 490                 495

Phe Tyr Pro Ser Asp Ile Ala Val Glu Trp Glu Ser Asn Gly Gln Pro
        500                 505                 510

Glu Asn Asn Tyr Lys Thr Thr Pro Pro Val Leu Asp Ser Asp Gly Ser
    515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
            565                 570

<210> SEQ ID NO 15
<211> LENGTH: 341
<212> TYPE: PRT
<213> ORGANISM: Artificial Sequence
<220> FEATURE:
<223> OTHER INFORMATION: Description of Artificial Sequence: Synthetic
      light chain variable region of a farletuzumab FOLR1-h38C2-DVD2
      immunoglobulin polypeptide

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ile Ser Ser Asn
        20                  25                  30

Asn Leu His Trp Tyr Gln Gln Lys Pro Gly Lys Ala Pro Lys Pro Trp
    35                  40                  45

Ile Tyr Gly Thr Ser Asn Leu Ala Ser Gly Val Pro Ser Arg Phe Ser
50                  55                  60

Gly Ser Gly Ser Gly Thr Asp Tyr Thr Phe Thr Ile Ser Ser Leu Gln
65                  70                  75                  80

```
Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Thr Val
            100                 105                 110

Ala Ala Pro Ser Val Phe Ile Phe Pro Pro Glu Leu Gln Met Thr Gln
        115                 120                 125

Ser Pro Ser Ser Leu Ser Ala Ser Val Gly Asp Arg Val Thr Ile Thr
    130                 135                 140

Cys Arg Ser Ser Gln Ser Leu Leu His Thr Tyr Gly Ser Pro Tyr Leu
145                 150                 155                 160

Asn Trp Tyr Leu Gln Lys Pro Gly Gln Ser Pro Lys Leu Leu Ile Tyr
                165                 170                 175

Lys Val Ser Asn Arg Phe Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Val Tyr Phe Cys Ser Gln Gly Thr His Leu Pro Tyr Thr
    210                 215                 220

Phe Gly Gly Gly Thr Lys Val Glu Ile Lys Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340

<210> SEQ ID NO 16
<211> LENGTH: 578
<212> TYPE: PRT
<213> ORGANISM: Artificial Sequence
<220> FEATURE:
<223> OTHER INFORMATION: Description of Artificial Sequence: Synthetic
      heavy chain variable region of a farletuzumab FOLR1-h38C2-DVD2
      immunoglobulin polypeptide

<400> SEQUENCE: 16

Glu Val Gln Leu Val Glu Ser Gly Gly Gly Trp Gln Pro Gly Arg Ser
1               5                   10                  15

Leu Arg Leu Ser Cys Ser Ala Ser Gly Phe Thr Phe Ser Gly Tyr Gly
            20                  25                  30

Leu Ser Trp Val Arg Gln Ala Pro Gly Lys Gly Leu Glu Trp Val Ala
        35                  40                  45

Met Ile Ser Ser Gly Gly Ser Tyr Thr Tyr Tyr Ala Asp Ser Val Lys
    50                  55                  60

Gly Arg Phe Ala Ile Ser Arg Asp Asn Ala Lys Asn Thr Leu Phe Leu
65                  70                  75                  80

Gln Met Asp Ser Leu Arg Pro Glu Asp Thr Gly Val Tyr Phe Cys Ala
```

-continued

```
                     85                  90                  95
Arg His Gly Asp Asp Pro Ala Trp Phe Ala Tyr Trp Gly Gln Gly Thr
                100                 105                 110
Pro Val Thr Val Ser Ser Thr Val Ala Ala Pro Ser Val Phe Ile Phe
            115                 120                 125
Pro Pro Glu Val Gln Leu Val Glu Ser Gly Gly Gly Leu Val Gln Pro
        130                 135                 140
Gly Gly Ser Leu Arg Leu Ser Cys Ala Ala Ser Gly Phe Thr Phe Ser
145                 150                 155                 160
Asn Tyr Trp Met Ser Trp Val Arg Gln Ser Pro Glu Lys Gly Leu Glu
                165                 170                 175
Trp Val Ser Glu Ile Arg Leu Arg Ser Asp Asn Tyr Ala Thr His Tyr
            180                 185                 190
Ala Glu Ser Val Lys Gly Arg Phe Thr Ile Ser Arg Asp Asn Ser Lys
        195                 200                 205
Asn Thr Leu Tyr Leu Gln Met Asn Ser Leu Arg Ala Glu Asp Thr Gly
    210                 215                 220
Ile Tyr Tyr Cys Lys Thr Tyr Phe Tyr Ser Phe Ser Tyr Trp Gly Gln
225                 230                 235                 240
Gly Thr Leu Val Thr Val Ser Ser Ala Ser Thr Lys Gly Pro Ser Val
                245                 250                 255
Phe Pro Leu Ala Pro Ser Ser Lys Ser Thr Ser Gly Gly Thr Ala Ala
            260                 265                 270
Leu Gly Cys Leu Val Lys Asp Tyr Phe Pro Glu Pro Val Thr Val Ser
        275                 280                 285
Trp Asn Ser Gly Ala Leu Thr Ser Gly Val His Thr Phe Pro Ala Val
    290                 295                 300
Leu Gln Ser Ser Gly Leu Tyr Ser Leu Ser Ser Val Val Thr Val Pro
305                 310                 315                 320
Ser Ser Ser Leu Gly Thr Gln Thr Tyr Ile Cys Asn Val Asn His Lys
                325                 330                 335
Pro Ser Asn Thr Lys Val Asp Lys Arg Val Glu Pro Lys Ser Cys Asp
            340                 345                 350
Lys Thr His Thr Cys Pro Pro Cys Pro Ala Pro Glu Leu Leu Gly Gly
        355                 360                 365
Pro Ser Val Phe Leu Phe Pro Pro Lys Pro Lys Asp Thr Leu Met Ile
    370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                405                 410                 415
Asn Ala Lys Thr Lys Pro Arg Glu Glu Gln Tyr Asn Ser Thr Tyr Arg
            420                 425                 430
Val Val Ser Val Leu Thr Val Leu His Gln Asp Trp Leu Asn Gly Lys
        435                 440                 445
Glu Tyr Lys Cys Lys Val Ser Asn Lys Ala Leu Pro Ala Pro Ile Glu
    450                 455                 460
Lys Thr Ile Ser Lys Ala Lys Gly Gln Pro Arg Glu Pro Gln Val Tyr
465                 470                 475                 480
Thr Leu Pro Pro Ser Arg Glu Glu Met Thr Lys Asn Gln Val Ser Leu
                485                 490                 495
Thr Cys Leu Val Lys Gly Phe Tyr Pro Ser Asp Ile Ala Val Glu Trp
            500                 505                 510
```

Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Lys Leu Thr Val Asp
        530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys

<210> SEQ ID NO 17
<211> LENGTH: 332
<212> TYPE: PRT
<213> ORGANISM: Artificial Sequence
<220> FEATURE:
<223> OTHER INFORMATION: Description of Artificial Sequence: Synthetic
      light chain variable region of a CD138-h38C2-DVD1
      immunoglobulin polypeptide

<400> SEQUENCE: 17

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Ala Ser Thr Lys Gly
            100                 105                 110

Pro Glu Leu Gln Met Thr Gln Ser Pro Ser Ser Leu Ser Ala Ser Val
        115                 120                 125

Gly Asp Arg Val Thr Ile Thr Cys Arg Ser Ser Gln Ser Leu Leu His
    130                 135                 140

Thr Tyr Gly Ser Pro Tyr Leu Asn Trp Tyr Leu Gln Lys Pro Gly Gln
145                 150                 155                 160

Ser Pro Lys Leu Leu Ile Tyr Lys Val Ser Asn Arg Phe Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Val Tyr Phe Cys Ser Gln
        195                 200                 205

Gly Thr His Leu Pro Tyr Thr Phe Gly Gly Gly Thr Lys Val Glu Ile
    210                 215                 220

Lys Arg Thr Val Ala Ala Pro Ser Val Phe Ile Phe Pro Pro Ser Asp
225                 230                 235                 240

Glu Gln Leu Lys Ser Gly Thr Ala Ser Val Val Cys Leu Leu Asn Asn
                245                 250                 255

Phe Tyr Pro Arg Glu Ala Lys Val Gln Trp Lys Val Asp Asn Ala Leu
            260                 265                 270

Gln Ser Gly Asn Ser Gln Glu Ser Val Thr Glu Gln Asp Ser Lys Asp

```
                275                 280                 285
Ser Thr Tyr Ser Leu Ser Ser Thr Leu Thr Leu Ser Lys Ala Asp Tyr
        290                 295                 300

Glu Lys His Lys Val Tyr Ala Cys Glu Val Thr His Gln Gly Leu Ser
305                 310                 315                 320

Ser Pro Val Thr Lys Ser Phe Asn Arg Gly Glu Cys
                325                 330

<210> SEQ ID NO 18
<211> LENGTH: 576
<212> TYPE: PRT
<213> ORGANISM: Artificial Sequence
<220> FEATURE:
<223> OTHER INFORMATION: Description of Artificial Sequence: Synthetic
      heavy chain variable region of a CD138-h38C2-DVD1
      immunoglobulin polypeptide

<400> SEQUENCE: 18

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
                20                  25                  30

Trp Ile Glu Trp Val Lys Gln Arg Pro Gly His Gly Leu Glu Trp Ile
            35                  40                  45

Gly Glu Ile Leu Pro Gly Thr Gly Arg Thr Ile Tyr Asn Glu Lys Phe
        50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser Asn Tyr
145                 150                 155                 160

Trp Met Ser Trp Val Arg Gln Ser Pro Glu Lys Gly Leu Glu Trp Val
                165                 170                 175

Ser Glu Ile Arg Leu Arg Ser Asp Asn Tyr Ala Thr His Tyr Ala Glu
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Gly Ile Tyr
    210                 215                 220

Tyr Cys Lys Thr Tyr Phe Tyr Ser Phe Ser Tyr Trp Gly Gln Gly Thr
225                 230                 235                 240

Leu Val Thr Val Ser Ser Ala Ser Thr Lys Gly Pro Ser Val Phe Pro
                245                 250                 255

Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
        275                 280                 285

Ser Gly Ala Leu Thr Ser Gly Val His Thr Phe Pro Ala Val Leu Gln
    290                 295                 300
```

Ser Ser Gly Leu Tyr Ser Leu Ser Ser Val Val Thr Val Pro Ser Ser
305                 310                 315                 320

Ser Leu Gly Thr Gln Thr Tyr Ile Cys Asn Val Asn His Lys Pro Ser
            325                 330                 335

Asn Thr Lys Val Asp Lys Arg Val Glu Pro Lys Ser Cys Asp Lys Thr
        340                 345                 350

His Thr Cys Pro Pro Cys Pro Ala Pro Glu Leu Leu Gly Gly Pro Ser
    355                 360                 365

Val Phe Leu Phe Pro Pro Lys Pro Lys Asp Thr Leu Met Ile Ser Arg
370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
            405                 410                 415

Lys Thr Lys Pro Arg Glu Glu Gln Tyr Asn Ser Thr Tyr Arg Val Val
        420                 425                 430

Ser Val Leu Thr Val Leu His Gln Asp Trp Leu Asn Gly Lys Glu Tyr
    435                 440                 445

Lys Cys Lys Val Ser Asn Lys Ala Leu Pro Ala Pro Ile Glu Lys Thr
450                 455                 460

Ile Ser Lys Ala Lys Gly Gln Pro Arg Glu Pro Gln Val Tyr Thr Leu
465                 470                 475                 480

Pro Pro Ser Arg Glu Glu Met Thr Lys Asn Gln Val Ser Leu Thr Cys
            485                 490                 495

Leu Val Lys Gly Phe Tyr Pro Ser Asp Ile Ala Val Glu Trp Glu Ser
        500                 505                 510

Asn Gly Gln Pro Glu Asn Asn Tyr Lys Thr Thr Pro Pro Val Leu Asp
    515                 520                 525

Ser Asp Gly Ser Phe Phe Leu Tyr Ser Lys Leu Thr Val Asp Lys Ser
530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
            565                 570                 575

<210> SEQ ID NO 19
<211> LENGTH: 338
<212> TYPE: PRT
<213> ORGANISM: Artificial Sequence
<220> FEATURE:
<223> OTHER INFORMATION: Description of Artificial Sequence: Synthetic
      light chain variable region of a CD138-h38C2-DVD2
      immunoglobulin polypeptide

<400> SEQUENCE: 19

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Thr Val Ala Ala Pro
            100                 105                 110

Ser Val Phe Ile Phe Pro Pro Glu Leu Gln Met Thr Gln Ser Pro Ser
            115                 120                 125

Ser Leu Ser Ala Ser Val Gly Asp Arg Val Thr Ile Thr Cys Arg Ser
        130                 135                 140

Ser Gln Ser Leu Leu His Thr Tyr Gly Ser Pro Tyr Leu Asn Trp Tyr
145                 150                 155                 160

Leu Gln Lys Pro Gly Gln Ser Pro Lys Leu Leu Ile Tyr Lys Val Ser
                165                 170                 175

Asn Arg Phe Ser Gly Val Pro Ser Arg Phe Ser Gly Ser Gly Ser Gly
            180                 185                 190

Thr Asp Phe Thr Leu Thr Ile Ser Ser Leu Gln Pro Glu Asp Phe Ala
        195                 200                 205

Val Tyr Phe Cys Ser Gln Gly Thr His Leu Pro Tyr Thr Phe Gly Gly
    210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 20
<211> LENGTH: 582
<212> TYPE: PRT
<213> ORGANISM: Artificial Sequence
<220> FEATURE:
<223> OTHER INFORMATION: Description of Artificial Sequence: Synthetic
      heavy chain variable region of a CD138-h38C2-DVD2
      immunoglobulin polypeptide

<400> SEQUENCE: 20

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

```
Ala Arg Arg Asp Tyr Tyr Gly Asn Phe Tyr Ala Met Asp Tyr Trp
            100                 105                 110

Gly Gln Gly Thr Ser Val Thr Val Ser Ser Thr Val Ala Ala Pro Ser
        115                 120                 125

Val Phe Ile Phe Pro Pro Glu Val Gln Leu Val Glu Ser Gly Gly Gly
130                 135                 140

Leu Val Gln Pro Gly Gly Ser Leu Arg Leu Ser Cys Ala Ala Ser Gly
145                 150                 155                 160

Phe Thr Phe Ser Asn Tyr Trp Met Ser Trp Val Arg Gln Ser Pro Glu
                165                 170                 175

Lys Gly Leu Glu Trp Val Ser Glu Ile Arg Leu Arg Ser Asp Asn Tyr
            180                 185                 190

Ala Thr His Tyr Ala Glu Ser Val Lys Gly Arg Phe Thr Ile Ser Arg
        195                 200                 205

Asp Asn Ser Lys Asn Thr Leu Tyr Leu Gln Met Asn Ser Leu Arg Ala
    210                 215                 220

Glu Asp Thr Gly Ile Tyr Tyr Cys Lys Thr Tyr Phe Tyr Ser Phe Ser
225                 230                 235                 240

Tyr Trp Gly Gln Gly Thr Leu Val Thr Val Ser Ser Ala Ser Thr Lys
                245                 250                 255

Gly Pro Ser Val Phe Pro Leu Ala Pro Ser Ser Lys Ser Thr Ser Gly
            260                 265                 270

Gly Thr Ala Ala Leu Gly Cys Leu Val Lys Asp Tyr Phe Pro Glu Pro
        275                 280                 285

Val Thr Val Ser Trp Asn Ser Gly Ala Leu Thr Ser Gly Val His Thr
    290                 295                 300

Phe Pro Ala Val Leu Gln Ser Ser Gly Leu Tyr Ser Leu Ser Ser Val
305                 310                 315                 320

Val Thr Val Pro Ser Ser Ser Leu Gly Thr Gln Thr Tyr Ile Cys Asn
                325                 330                 335

Val Asn His Lys Pro Ser Asn Thr Lys Val Asp Lys Arg Val Glu Pro
            340                 345                 350

Lys Ser Cys Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Glu Glu Met Thr Lys Asn
                485                 490                 495

Gln Val Ser Leu Thr Cys Leu Val Lys Gly Phe Tyr Pro Ser Asp Ile
            500                 505                 510
```

```
Ala Val Glu Trp Glu Ser Asn Gly Gln Pro Glu Asn Tyr Lys Thr
            515                 520                 525

Thr Pro Pro Val Leu Asp Ser Asp Gly Ser Phe Phe Leu Tyr Ser Lys
    530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580

<210> SEQ ID NO 21
<211> LENGTH: 337
<212> TYPE: PRT
<213> ORGANISM: Artificial Sequence
<220> FEATURE:
<223> OTHER INFORMATION: Description of Artificial Sequence: Synthetic
      light chain variable region of a CD79b-h38C2-DVD1
      immunoglobulin polypeptide

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Ala Ser Thr Lys Gly Pro Glu Leu Gln Met Thr Gln Ser Pro Ser Ser
        115                 120                 125

Leu Ser Ala Ser Val Gly Asp Arg Val Thr Ile Thr Cys Arg Ser Ser
    130                 135                 140

Gln Ser Leu Leu His Thr Tyr Gly Ser Pro Tyr Leu Asn Trp Tyr Leu
145                 150                 155                 160

Gln Lys Pro Gly Gln Ser Pro Lys Leu Leu Ile Tyr Lys Val Ser Asn
                165                 170                 175

Arg Phe Ser Gly Val Pro Ser Arg Phe Ser Gly Ser Gly Ser Gly Thr
            180                 185                 190

Asp Phe Thr Leu Thr Ile Ser Ser Leu Gln Pro Glu Asp Phe Ala Val
        195                 200                 205

Tyr Phe Cys Ser Gln Gly Thr His Leu Pro Tyr Thr Phe Gly Gly Gly
    210                 215                 220

Thr Lys Val Glu Ile Lys Arg Thr Val Ala Ala Pro Ser Val Phe Ile
225                 230                 235                 240

Phe Pro Pro Ser Asp Glu Gln Leu Lys Ser Gly Thr Ala Ser Val Val
                245                 250                 255

Cys Leu Leu Asn Asn Phe Tyr Pro Arg Glu Ala Lys Val Gln Trp Lys
            260                 265                 270

Val Asp Asn Ala Leu Gln Ser Gly Asn Ser Gln Glu Ser Val Thr Glu
```

```
                 275                 280                 285
Gln Asp Ser Lys Asp Ser Thr Tyr Ser Leu Ser Ser Thr Leu Thr Leu
    290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
                325                 330                 335

Cys

<210> SEQ ID NO 22
<211> LENGTH: 571
<212> TYPE: PRT
<213> ORGANISM: Artificial Sequence
<220> FEATURE:
<223> OTHER INFORMATION: Description of Artificial Sequence: Synthetic
      heavy chain variable region of a CD79b-h38C2-DVD1
      immunoglobulin polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Asn Tyr Trp Met Ser Trp Val
145                 150                 155                 160

Arg Gln Ser Pro Glu Lys Gly Leu Glu Trp Val Ser Glu Ile Arg Leu
                165                 170                 175

Arg Ser Asp Asn Tyr Ala Thr His Tyr Ala Glu Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Gly Ile Tyr Tyr Cys Lys Thr Tyr
    210                 215                 220

Phe Tyr Ser Phe Ser Tyr Trp Gly Gln Gly Thr Leu Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285
```

```
Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 23
<211> LENGTH: 343
<212> TYPE: PRT
<213> ORGANISM: Artificial Sequence
<220> FEATURE:
<223> OTHER INFORMATION: Description of Artificial Sequence: Synthetic
      light chain variable region of a CD79b-h38C2-DVD2
      immunoglobulin polypeptide

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
```

```
                65                  70                  75                  80
Ser Leu Gln Pro Glu Asp Phe Ala Thr Tyr Tyr Cys Gln Gln Ser Asn
                    85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Glu Leu Gln Met
            115                 120                 125

Thr Gln Ser Pro Ser Ser Leu Ser Ala Ser Val Gly Asp Arg Val Thr
        130                 135                 140

Ile Thr Cys Arg Ser Ser Gln Ser Leu Leu His Thr Tyr Gly Ser Pro
145                 150                 155                 160

Tyr Leu Asn Trp Tyr Leu Gln Lys Pro Gly Gln Ser Pro Lys Leu Leu
                165                 170                 175

Ile Tyr Lys Val Ser Asn Arg Phe Ser Gly Val Pro Ser Arg Phe Ser
            180                 185                 190

Gly Ser Gly Ser Gly Thr Asp Phe Thr Leu Thr Ile Ser Ser Leu Gln
        195                 200                 205

Pro Glu Asp Phe Ala Val Tyr Phe Cys Ser Gln Gly Thr His Leu Pro
    210                 215                 220

Tyr Thr Phe Gly Gly Gly Thr Lys Val Glu Ile Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
    290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
            340

<210> SEQ ID NO 24
<211> LENGTH: 577
<212> TYPE: PRT
<213> ORGANISM: Artificial Sequence
<220> FEATURE:
<223> OTHER INFORMATION: Description of Artificial Sequence: Synthetic
      heavy chain variable region of a CD79b-h38C2-DVD2
      immunoglobulin polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80
```

-continued

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Thr Val Ala Ala Pro Ser Val Phe Ile Phe Pro
            115                 120                 125

Pro Glu Val Gln Leu Val Glu Ser Gly Gly Leu Val Gln Pro Gly
    130                 135                 140

Gly Ser Leu Arg Leu Ser Cys Ala Ala Ser Gly Phe Thr Phe Ser Asn
145                 150                 155                 160

Tyr Trp Met Ser Trp Val Arg Gln Ser Pro Glu Lys Gly Leu Glu Trp
                165                 170                 175

Val Ser Glu Ile Arg Leu Arg Ser Asp Asn Tyr Ala Thr His Tyr Ala
                180                 185                 190

Glu Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Gly Ile
    210                 215                 220

Tyr Tyr Cys Lys Thr Tyr Phe Tyr Ser Phe Ser Tyr Trp Gly Gln Gly
225                 230                 235                 240

Thr Leu Val Thr Val Ser Ser Ala Ser Thr Lys Gly Pro Ser Val Phe
            245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
            325                 330                 335

Ser Asn Thr Lys Val Asp Lys Arg Val Glu Pro Lys Ser Cys Asp Lys
            340                 345                 350

Thr His Thr Cys Pro Pro Cys Pro Ala Pro Glu Leu Leu Gly Gly Pro
            355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
            405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
            435                 440                 445

Tyr Lys Cys Lys Val Ser Asn Lys Ala Leu Pro Ala Pro Ile Glu Lys
            450                 455                 460

Thr Ile Ser Lys Ala Lys Gly Gln Pro Arg Glu Pro Gln Val Tyr Thr
465                 470                 475                 480

Leu Pro Pro Ser Arg Glu Glu Met Thr Lys Asn Gln Val Ser Leu Thr
                485                 490                 495

```
Cys Leu Val Lys Gly Phe Tyr Pro Ser Asp Ile Ala Val Glu Trp Glu
            500             505             510

Ser Asn Gly Gln Pro Glu Asn Asn Tyr Lys Thr Thr Pro Pro Val Leu
        515             520             525

Asp Ser Asp Gly Ser Phe Phe Leu Tyr Ser Lys Leu Thr Val Asp Lys
        530             535             540

Ser Arg Trp Gln Gln Gly Asn Val Phe Ser Cys Ser Val Met His Glu
545             550             555             560

Ala Leu His Asn His Tyr Thr Gln Lys Ser Leu Ser Leu Ser Pro Gly
                565             570             575

Lys
```

DUAL VARIABLE DOMAIN IMMUNOCONJUGATES AND USES THEREOF

CROSS REFERENCE TO RELATED APPLICATIONS

This application claims priority benefit of the filing date of U.S. Provisional Patent Application Ser. No. 62/220,148, filed on Sep. 17, 2015, the disclosure of which application is herein incorporated by reference in its entirety. This application also claims priority benefit of the filing date of U.S. Provisional Patent Application Ser. No. 62/327,849, filed on Apr. 26, 2016, the disclosure of which application is herein incorporated by reference in its entirety.

GOVERNMENT RIGHTS

This invention was made with U.S. government support under Grant Number CA174844 awarded by the NIH. The U.S. government has certain rights in the invention.

FIELD OF THE INVENTION

The present invention relates to dual variable domain immunoconjugates, as well as methods of making and using the same in the prevention and treatment of cancer, and other diseases.

INCORPORATION OF SEQUENCE LISTING

A sequence listing contained in the file named "P34344WO00.txt" which is 85,476 bytes (measured in MS-Windows®) and created on Sep. 16, 2016 comprises 24 sequences, is filed electronically herewith and incorporated by reference in its entirety.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

In attempts to discover effective cellular targets for cancer therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The use of antibody-drug conjugates (ADC), i.e., immunoconjugates, for the local delivery of cytotoxic or cytostatic agents, i.e., drugs to kill or inhibit tumor cells in the treatment of cancer allows targeted delivery of a drug moiety to tumor cells, and intracellular accumulation therein, where systemic administration of these unconjugated drug agents can result in unacceptable levels of toxicity to normal cells as well as the tumor cells sought to be eliminated. Efforts to improve the therapeutic index, i.e., the maximal efficacy and minimal toxicity of ADCs have focused on the selectivity of polyclonal and monoclonal antibodies (mAbs) as well as drug-linking and drug-releasing properties (Lambert, J. (2005) Curr. Opinion in Pharmacology 5:543-549). Drug moieties used in antibody drug conjugates include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties can affect cytotoxic and cytostatic mechanisms including tubulin binding, DNA binding, or topoisomerase inhibition. Some cytotoxic drugs tend to be inactive or less active when conjugated to large antibodies or protein receptor ligands.

Conventional means of attaching, i.e., linking through covalent bonds, a moiety (e.g., a drug moiety) to an antibody generally leads to a heterogeneous mixture of molecules where the moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods can be inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process can be non-reproducible due to difficulties in controlling the reaction conditions and characterizing reactants and intermediates.

SUMMARY

Dual variable domain (DVD) immunoconjugates and uses thereof are provided. Aspects of the subject immunoconjugates include a DVD immunoglobulin molecule having a first and a second variable domain, and a cargo moiety (e.g., a drug moiety) that is covalently conjugated to the second variable domain via a linker. Methods of making and using the subject immunoconjugates in the prevention and/or treatment of cancer and other diseases are also provided.

Aspects of the invention include an immunoconjugate having the formula Ig-(L-D)$_n$, where: Ig is a dual variable domain immunoglobulin molecule, or an immunoglobulin-fragment (antigen-binding fragment) thereof, where the dual variable domain immunoglobulin molecule comprises a first variable domain that binds to a binding target, and a second variable domain that comprises a reactive residue; L is a linker that is covalently conjugated to the reactive residue of the second variable domain of Ig; D is a drug moiety; and n is selected from an integer from 1 to 12, such as 1, 2, 3, 4, 5, 6, 7, 8, 9, 10, 11, or 12. In an aspect, a reactive residue allows for the stoichiometric attachment of L, and encompasses, but is not limited to, natural and unnatural amino acids containing SH, NH2, OH, SeH, N3, alkyne, alkene, strained alkynes, strained alkenes, C=O and activated C—H as reactive functional groups.

Further aspects of the invention include an immunoconjugate having the formula Ig-(L-D)$_n$, where: Ig is a dual variable domain immunoglobulin molecule, or an antigen-binding fragment thereof, where the dual variable domain immunoglobulin molecule comprises a first variable domain that binds to a binding target, and a second variable domain that comprises a reactive lysine residue; L is a linker that is covalently conjugated to the reactive lysine residue of the second variable domain of Ig; D is a drug moiety; and n is 1 or 2.

BRIEF DESCRIPTION OF THE SEQUENCES

SEQ ID NOs: 1 and 2 are amino acid sequences of peptide linkers.

SEQ ID NO: 3 is an amino acid sequence of a light chain variable region of a humanized 38C2 (h38C2) antibody.

SEQ ID NO: 4 is an amino acid sequence of a heavy chain variable region of a humanized 38C2 (h38C2) antibody.

SEQ ID NO: 5 is an amino acid sequence of a light chain variable region of an HER2-h38C2-DVD1 immunoglobulin.

SEQ ID NO: 6 is an amino acid sequence of a heavy chain variable region of an HER2-h38C2-DVD1 immunoglobulin.

SEQ ID NO: 7 is an amino acid sequence of a light chain variable region of an HER2-h38C2-DVD2 immunoglobulin.

SEQ ID NO: 8 is an amino acid sequence of a heavy chain variable region of an HER2-h38C2-DVD2 immunoglobulin.

SEQ ID NO: 9 is an amino acid sequence of a light chain variable region of an IMGN-853 FOLR1-h38C2-DVD1 immunoglobulin.

SEQ ID NO: 10 is an amino acid sequence of a heavy chain variable region of an IMGN-853 FOLR1-h38C2-DVD1 immunoglobulin.

SEQ ID NO: 11 is an amino acid sequence of a light chain variable region of an IMGN-853 FOLR1-h38C2-DVD2 immunoglobulin.

SEQ ID NO: 12 is an amino acid sequence of a heavy chain variable region of an IMGN-853 FOLR1-h38C2-DVD2 immunoglobulin.

SEQ ID NO: 13 is an amino acid sequence of a light chain variable region of a farletuzumab FOLR1-h38C2-DVD1 immunoglobulin.

SEQ ID NO: 14 is an amino acid sequence of a heavy chain variable region of a farletuzumab FOLR1-h38C2-DVD1 immunoglobulin.

SEQ ID NO: 15 is an amino acid sequence of a light chain variable region of a farletuzumab FOLR1-h38C2-DVD2 immunoglobulin.

SEQ ID NO: 16 is an amino acid sequence of a heavy chain variable region of a farletuzumab FOLR1-h38C2-DVD2 immunoglobulin.

SEQ ID NO: 17 is an amino acid sequence of a light chain variable region of a CD138-h38C2-DVD1 immunoglobulin.

SEQ ID NO: 18 is an amino acid sequence of a heavy chain variable region of a CD138-h38C2-DVD1 immunoglobulin.

SEQ ID NO: 19 is an amino acid sequence of a light chain variable region of a CD138-h38C2-DVD2 immunoglobulin.

SEQ ID NO: 20 is an amino acid sequence of a heavy chain variable region of a CD138-h38C2-DVD2 immunoglobulin.

SEQ ID NO: 21 is an amino acid sequence of a light chain variable region of a CD79b-h38C2-DVD1 immunoglobulin.

SEQ ID NO: 22 is an amino acid sequence of a heavy chain variable region of a CD79b-h38C2-DVD1 immunoglobulin.

SEQ ID NO: 23 is an amino acid sequence of a light chain variable region of a CD79b-h38C2-DVD2 immunoglobulin.

SEQ ID NO: 24 is an amino acid sequence of a heavy chain variable region of a CD79b-h38C2-DVD2 immunoglobulin.

BRIEF DESCRIPTION OF THE DRAWINGS

FIG. 14 depicts various non-limiting examples of drug moieties.

FIG. 20 depicts two graphs providing data from a third cytotoxicity assay demonstrating cell killing by an anti-HER2 dual variable domain immunoconjugate.

FIG. 21 shows non-limiting example structures of DVD1 and DVD2, as well as Coomassie staining to confirm expected size and purity.

FIG. 22 provides a schematic illustration as well as flow cytometry data demonstrating selective binding to HER2 expressing SKBR3 cells and no binding to HER2 negative MDA-MB-468 cells.

FIG. 28 provides graphical data that demonstrates catalytic activity various composition, including DVD1, h38C2, trastuzumab, and DVD1-ADC.

FIG. 35 provides graphical data depicting catalytic activity of additional h38C2-based bispecific compositions.

FIG. 37A provides a schematic illustration of a structure of β-lactam MMAF for ADC preparation.

FIG. 37B provides a schematic illustration of a drug attachment site (star) at the lysine of h38C2 (circle).

FIG. 37C provides graphical data that demonstrates a complete loss of catalytic activity of anti-HER2 DVD1/MMAF, confirming complete conjugation; unconjugated anti-HER2 DVD1 serves as a positive control; alanine mutated anti-HER2 DVD1 (orange) and trastuzumab IgG1 (purple) serve as negative controls.

DETAILED DESCRIPTION

Figure 1:
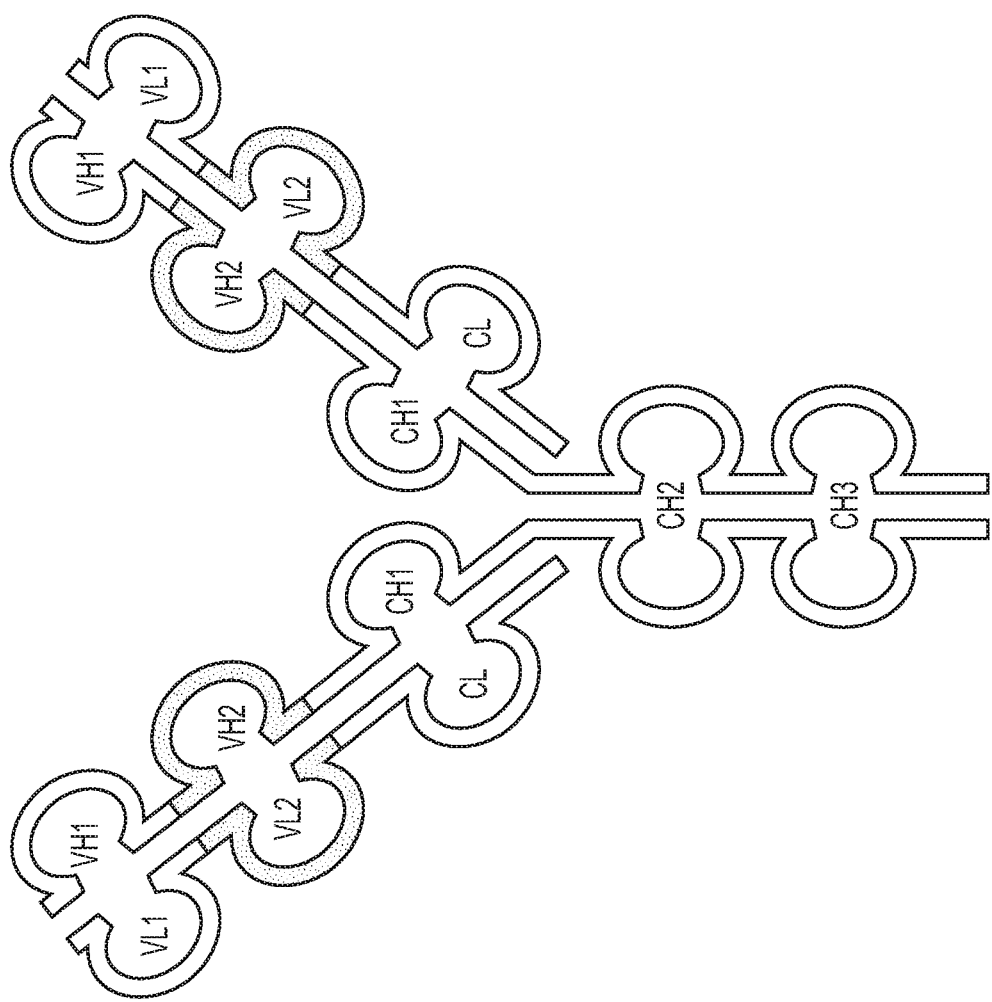
FIG. 1 is a schematic illustration of a dual variable domain immunoglobulin molecule that includes two identical light chains and two identical heavy chains.

Dual variable domain (DVD) immunoconjugates and uses thereof are provided. Aspects of the subject immunoconjugates include a DVD immunoglobulin molecule having a first and a second variable domain, and a drug moiety that is covalently conjugated to the second variable domain via a linker. Methods of making and using the subject immunoconjugates in the prevention and/or treatment of cancer and other diseases are also provided.

Before the present invention is described in greater detail, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

The practice of the present invention can employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "immunoglobulin" or "antibody" as used interchangeably herein refers to a basic 4-chain heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain has an N-terminus and a C-terminus, and also has regularly spaced intrachain disulfide bridges. Each H chain has at the N-terminus a variable domain ($V_H$) followed by three constant domains ($C_H1$, $C_H2$ and $C_H3$). Each L chain has at the N-terminus a variable domain ($V_L$) followed by one constant domain ($C_L$). The $V_L$ is aligned with the $V_H$ and the $C_L$ is aligned with the first constant domain of the heavy chain ($C_H1$). Particular amino acid residues are believed to form an interface between the L chain and H chain variable domains. The pairing of a $V_H$ and $V_L$ together forms a single antigen-binding site.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$, and $\mu$, respectively. The $\gamma$ and $\alpha$ classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an immunoglobulin refers to the N-terminal domains of the H or L chain of the immunoglobulin. The variable domain of the H chain can be referred to as "$V_H$." The variable domain of the light chain can be referred to as "$V_L$." These domains are generally the most variable parts of an immunoglobulin and contain the antigen-binding sites.

The term "variable" refers to the fact that certain segments of the variable domains differ extensively in sequence among immunoglobulins. The V domain mediates antigen binding and defines specificity of a particular immunoglobulin for its particular antigen. However, the variability is not evenly distributed across the 110-amino acid span of most variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native H and L chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of immunoglobulins (see Kabat et al., Sequences of Proteins of Immunological Interest, 5th Ed. Public Health Service, National Institutes of Health, Bethesda, Md. (1991)). The constant domains are not involved directly in binding an immunoglobulin to an antigen, but exhibit various effector functions, such as participation of the immunoglobulin in antibody dependent cellular cytotoxicity (ADCC), antibody-dependent cellular phagocytosis (ADCP), and complement-dependent cytotoxicity (CDC).

An "intact" immunoglobulin is one that comprises an antigen-binding site as well as a $C_L$ and at least H chain constant domains, $C_H1$, $C_H2$ and $C_H3$. The constant domains can be native sequence constant domains (e.g., human native sequence constant domains) or amino acid sequence variants thereof. An intact immunoglobulin can have one or more effector functions.

A "naked immunoglobulin" for the purposes herein is an immunoglobulin that is not conjugated to a drug moiety.

"Immunoglobulin fragments" comprise a portion of an intact immunoglobulin, preferably the antigen binding or variable region of the intact immunoglobulin. Examples of immunoglobulin fragments include, but are not limited to, Fab, Fab', F(ab')$_2$, and Fv fragments; diabodies; linear immunoglobulins (see U.S. Pat. No. 5,641,870, Example 2; Zapata et al., Protein Eng. 8(10): 1057-1062 [1995]); single-chain immunoglobulin molecules; and multispecific immunoglobulins formed from immunoglobulin fragments. In some aspects, the immunoglobulin fragments include all possible alternate fragment formats. In some aspects, the immunoglobulin fragments may be bispecific. In some aspects, the immunoglobulin fragments may be bi-paratopic. In some aspects, the immunoglobulin fragments may be trispecific. In some aspects, the immunoglobulin fragments may be multimeric. In some aspects, an immunoglobulin fragment comprises an antigen binding site of the intact immunoglobulin and thus retains the ability to bind antigen. In some aspects, the immunoglobulin fragment contains single variable domains which have the ability to bind antigen. In some aspects, the immunoglobulin fragments are further modified (not limited to peptide addition, pegylation, hesylation, glycosylation) to modulate activity, properties, pharmacokinetic behavior and in vivo efficacy.

Papain digestion of immunoglobulins produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an immunoglobulin yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the immunoglobulin hinge region. Fab'-SH is the designation herein for Fab' in which the cysteine residue(s) of the constant domains bear a free thiol group. F(ab')$_2$ immunoglobulin fragments originally were produced as pairs of Fab' fragments which have hinge cysteines between them. Other chemical couplings of immunoglobulin fragments are also known.

The Fc fragment comprises the carboxy-terminal portions of both H chains held together by disulfides. The effector functions of immunoglobulins are determined by sequences in the Fc region, which region is also the part recognized by Fc receptors (FcR) found on certain types of cells.

"Fv" is the minimum immunoglobulin fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the immunoglobulin. However, even a single variable domain (or half of an Fv comprising only three CDRs specific for an antigen) has the ability to recognize and bind antigen, although typically at a lower affinity than the entire binding site. When used herein in reference to a DVD immunoglobulin molecule, the term "Fv" refers to a binding fragment that includes both the first and the second variable domains of the heavy chain and the light chain.

"Single-chain Fv" also abbreviated as "sFv" or "scFv" are immunoglobulin fragments that comprise the $V_H$ and $V_L$ immunoglobulin domains connected into a single polypeptide chain. Preferably, the sFv polypeptide further comprises a polypeptide linker between the $V_H$ and $V_L$ domains which enables the sFv to form the desired structure for antigen binding. For a review of sFv, see Plückthun in The Pharmacology of Monoclonal Antibodies, vol. 113, Rosenburg and Moore eds., Springer-Verlag, New York, pp. 269-315 (1994); Borrebaeck 1995, infra. When used herein in reference to a DVD immunoglobulin molecule, the term "scFv" refers to a binding fragment that includes both the first and the second variable domains of the heavy chain and the light chain.

The term "dual variable domain immunoglobulin" or "DVD-Ig" as used herein refers to an immunoglobulin molecule as described above, wherein both the H and L chains include a second variable domain located adjacent to the first variable domain. The L chain of a DVD-Ig therefore includes, from N-terminus to C-terminus, the following domains: $V_L1$-$V_L2$-$C_L$. The H chain of a DVD-Ig therefore includes, from N-terminus to C-terminus, the following domains: $V_H1$-$V_H2$-$C_H1$-$C_H2$-$C_H3$. The pairing of a $V_L1$ and $V_H1$ together forms a first antigen-binding site. The pairing of a $V_L2$ and $V_H2$ together forms a second antigen binding site.

Unless stated otherwise, the term "immunoglobulin" or "antibody" specifically includes native human and non-human IgG1, IgG2, IgG3, IgG4, IgE, IgA1, IgA2, IgD and IgM antibodies, including naturally occurring variants.

The term "native" with reference to a polypeptide (e.g., an antibody or immunoglobulin) is used herein to refer to a polypeptide having a sequence that occurs in nature, regardless of its mode of preparation. The term "non-native" with reference to a polypeptide (e.g., an antibody or immunoglobulin) is used herein to refer to a polypeptide having a sequence that does not occur in nature.

The term "polypeptide" is used herein in the broadest sense and includes peptide sequences. The term "peptide" generally describes linear molecular chains of amino acids containing up to about 30, preferably up to about 60 amino acids covalently linked by peptide bonds.

The term "monoclonal" as used herein refers to an antibody or immunoglobulin molecule (e.g., a DVD Ig molecule) obtained from a population of substantially homogeneous immunoglobulins, i.e., the individual immunoglobulins comprising the population are identical except for possible naturally occurring mutations that can be present in minor amounts. Monoclonal immunoglobulins are highly specific, being directed against a single antigenic site. Furthermore, in contrast to conventional (polyclonal) antibody preparations which typically include different antibodies directed against different determinants (epitopes), each monoclonal immunoglobulin is directed against a single determinant on the antigen. The modifier "monoclonal" indicates the character of the immunoglobulin as being obtained from a substantially homogeneous population of immunoglobulins, and is not to be construed as requiring production of the antibody by any particular method. For example, the monoclonal immunoglobulins in accordance with the present invention can be made by the hybridoma method first described by Köhler and Milstein (1975) Nature 256:495, or can be made by recombinant DNA methods (see, e.g., U.S. Pat. No. 4,816,567).

The monoclonal immunoglobulins herein specifically include "chimeric" immunoglobulins in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., rodent, e.g., murine or rabbit) immunoglobulins are immunoglobulins which contain minimal sequences derived from non-human immunoglobulin. For the most part, humanized immunoglobulins are human immunoglobulins (recipient antibody) in which residues from a hypervariable region of the recipient are replaced by residues from a hypervariable region of a non-human species (donor antibody) such as mouse, rat, hamster, rabbit, chicken, bovine or non-human primate having the desired specificity, affinity, and capacity. In some instances, Fv framework region (FR) residues of the human immunoglobulin are also replaced by corresponding non-human residues. Furthermore, humanized antibodies can comprise residues which are not found in the recipient antibody or in the donor antibody. These modifications are made to further refine antibody performance. In general, the humanized immunoglobulin will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized immunoglobulin optionally also will comprise at least a portion of an immunoglobulin constant region (Fc), typically that of a human immunoglobulin. For further details, see Jones et al. (1986) Nature 321:522-525; Riechmann et al. (1988) Nature 332: 323-329; and Presta (1992) Curr. Op. Struct. Biol. 2:593-596.

The term "human immunoglobulin", as used herein, is intended to include immunoglobulins having variable and constant regions derived from human germline immunoglobulin sequences. The human immunoglobulins of the invention can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human immunoglobulin", as used herein, is not intended to include immunoglobulins in which CDR sequences derived from the germline of another mammalian species, such as a mouse, have been grafted onto human framework sequences.

An "isolated" immunoglobulin herein is one which has been identified and separated and/or recovered from a component of its natural environment in a recombinant host cell. Contaminant components of its natural environment are materials which would interfere with diagnostic or therapeutic uses for the immunoglobulin, and can include enzymes, hormones, and other proteinaceous or nonproteinaceous solutes, as well as undesired byproducts of the production. In some aspects, an isolated immunoglobulin herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or nonreducing conditions using Coomassie blue or, preferably, silver stain. Ordinarily, an isolated immunoglobulin will be prepared by at least one purification step.

The term "specific binding" or "specifically binds to" or is "specific for" refers to the binding of a binding moiety to a binding target, such as the binding of an immunoglobulin to a target antigen, e.g., an epitope on a particular polypeptide, peptide, or other target (e.g. a glycoprotein target), and means binding that is measurably different from a non-specific interaction (e.g., a non-specific interaction can be binding to bovine serum albumin or casein). Specific binding can be measured, for example, by determining binding of a binding moiety, or an immunoglobulin, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_d$ for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an immunoglobulin) and its binding partner (e.g., an antigen). Unless indicated otherwise, as used herein, "binding affinity" refers to intrinsic binding affinity which reflects a 1:1 interaction between members of a binding pair (e.g., immunoglobulin and antigen). The affinity of a molecule X for its partner Y can generally be represented by the dissociation constant ($K_d$). For example, the $K_d$ can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "$K_d$" or "$K_d$ value" refers to a dissociation constant measured by a technique appropriate for the immunoglobulin and target pair, for example using surface plasmon resonance assays, for example, using a Biacore X100 or a Biacore T200 (GE Healthcare, Piscataway, N.J.) at 25° C. with immobilized antigen CMS chips.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin The term "epitope" includes any molecular determinant capable of specific binding to an immunoglobulin. In certain aspects, epitope determinants include chemically active surface groupings of molecules such as amino acids, sugar side chains, phosphoryl, or sulfonyl, and, in certain aspects, can have specific three dimensional structural characteristics, and/or specific charge characteristics. An epitope is a region of an antigen that is bound by an immunoglobulin. A "binding region" is a region on a binding target bound by a binding molecule.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an immunoglobulin or trigger a cellular immune response. An immunogen refers to an antigen, which can elicit an immune response in an organism, particularly an animal, more particularly a mammal including a human. The term antigen includes regions known as antigenic determinants or epitopes, as defined above.

An "antigen-binding site" or "antigen-binding region" of an immunoglobulin of the present invention typically contains six complementarity determining regions (CDRs) within each variable domain, and which contribute in varying degrees to the affinity of the binding site for antigen. In each variable domain there are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs can be sufficient for binding to some binding targets. Thus, in some instances, the CDRs of a $V_H$ or a $V_L$ domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the immunoglobulins according to the current invention. In one aspect, Chinese hamster ovary (CHO) cells are used as host cells. In some aspects, E. coli are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to a peptide or polypeptide sequence, i.e., the h38C2 antibody polypeptide sequences identified herein, is defined as the percentage of amino acid residues in a candidate sequence that are identical with the amino acid residues in the specific peptide or polypeptide sequence after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Treating" or "treatment" refers to both therapeutic treatment and prophylactic or preventative measures, wherein the object is to prevent or slow down (lessen) a targeted pathologic condition or disorder. Those in need of treatment include those already with the disorder, as well as those prone to have the disorder, or those in whom the disorder is to be prevented. For example, a subject or mammal is successfully "treated" for cancer, if, after receiving a therapeutic amount of a subject immunoconjugate according to the methods of the present invention, the subject shows observable and/or measurable reduction in or absence of one or more of the following: reduction in the number of cancer cells or absence of the cancer cells; reduction in the tumor size; inhibition (i.e., slowing to some extent and preferably stopping) of cancer cell infiltration into peripheral organs, including the spread of cancer into soft tissue and bone; inhibition (i.e., slowing to some extent and preferably stopping) of tumor metastasis; inhibition, to some extent, of tumor growth; and/or relief to some extent of one or more of the symptoms associated with the specific cancer; reduced morbidity and/or mortality, and improvement in quality of life issues.

Dual Variable Domain Immunoglobulins

Aspects of the invention include dual variable domain (DVD) immunoglobulin molecules with a first variable domain that binds to a target antigen, and a second variable domain that includes uniquely reactive residues that provide a site for covalent attachment of a linker molecule. A subject DVD immunoglobulin molecule includes two identical light chains, as well as two identical heavy chains. Each light chain and each heavy chain includes an N-terminus and a C-terminus. Each light chain includes a first and a second variable domain, designated as $V_L1$ and $V_L2$, as well as a constant domain, designated as $C_L$. In some aspects, a light chain comprises a kappa light chain. In some aspects, a light chain comprises a lambda light chain.

Aspects of the invention include dual variable domain (DVD) immunoglobulin molecules with a first variable domain that binds to a target antigen, and a second variable domain that includes a single, uniquely reactive lysine residue that provides a site for covalent attachment of a linker molecule. A subject DVD immunoglobulin molecule includes two identical light chains, as well as two identical heavy chains. Each light chain and each heavy chain includes an N-terminus and a C-terminus. Each light chain includes a first and a second variable domain, designated as $V_L1$ and $V_L2$, as well as a constant domain, designated as $C_L$. In some aspects, a light chain comprises a kappa light chain. In some aspects, a light chain comprises a lambda light chain.

In some aspects, each heavy chain includes a first and a second variable domain, designated as $V_H1$ and $V_H2$, as well as a constant domain designated as $C_H1$, followed by heavy chain Fc region domains. In some aspects, Fc region domains on a heavy chain can include Fc region domains that are specific to a particular immunoglobulin type or subtype, including but not limited to Fc regions from an IgG (such as an IgG1, IgG2, IgG3 or IgG4), IgA (such as an IgA1 or IgA2), IgM, IgE or IgD antibody. For example, in some aspects, an immunoglobulin belongs to the IgG class, and the heavy chain comprises a γ heavy chain. In some aspects, an immunoglobulin belongs to the IgG1 class, and the heavy chain comprises a γ1 heavy chain. In some aspects, an immunoglobulin belongs to the IgG2 class, and the heavy chain comprises a γ2 heavy chain. In some aspects, an immunoglobulin belongs to the IgG3 class, and the heavy chain comprises a γ3 heavy chain. In some aspects, an immunoglobulin belongs to the IgG4 class, and the heavy chain comprises a γ4 heavy chain.

In some aspects, an immunoglobulin belongs to the IgA class, and a heavy chain comprises an α heavy chain. In some aspects, an immunoglobulin belongs to the IgA1 class, and a heavy chain comprises a α1 heavy chain. In some aspects, an immunoglobulin belongs to the IgA2 class, and a heavy chain comprises a α2 heavy chain.

In some aspects, an immunoglobulin belongs to the IgD class, and a heavy chain comprises a δ heavy chain. In some aspects, an immunoglobulin belongs to the IgE class, and a heavy chain comprises an ε heavy chain. In some aspects, an immunoglobulin belongs to the IgM class, and a heavy chain comprises a μ heavy chain.

In some aspects, an immunoglobulin molecule can contain a native polypeptide sequence that occurs in nature.

The organization of the variable and constant domains along the light chain generally proceeds from the N-terminus to the C-terminus as $V_L1$-$V_L2$-$C_L$. However, in certain aspects, the organization of the variable domains on the light chain can be reversed, such that the organization from N- to C-terminus is $V_L2$-$V_L1$-$C_L$. This same organization applies to binding fragments of the subject DVD immunoglobulins, wherein the organization from N- to C-terminus can be $V_L1$-$V_L2$ or $V_L2$-$V_L1$. Similarly, the organization of the variable and constant domains along the heavy chain generally proceeds from the N-terminus to the C-terminus as $V_H1$-$V_H2$-$C_H1$-Fc, but can be modified to mirror the organization of the domains on a light chain so that the appropriate domains on a light chain are paired with the appropriate domains on a heavy chain when the immunoglobulin molecule, or binding fragment thereof, is assembled.

In certain aspects, the organization of the variable and constant domains along a light and heavy chain can be organized such that the sequence of the domains along a light chain proceeds from N- to C-terminus as $V_L1$-$V_L2$-$C_H1$, and the organization of domains along a heavy chain proceeds from N- to C-terminus as $V_H1$-$V_H2$-$C_L$-Fc. This particular organization is referred to as a CrossMAb organization, and is described in detail in Klein et al., mAbs 4, 653-663 (2012), the disclosure of which is incorporated by reference herein in its entirety. In certain aspects, a CrossMAb organization can be used to generate bispecific DVD immunoglobulins, which are described further below.

In some aspects, a first and second variable domain are linked along their light chain or heavy chain by a peptide linker sequence. A peptide linker sequence can be a single amino acid or a polypeptide sequence. In some aspects, a peptide linker sequence is ASTKGP (SEQ ID NO: 1) or TVAAPSVFIFPP (SEQ ID NO: 2). Additional peptide linker sequences that can be used to link a first and second variable domain of the subject DVD immunoglobulins are provided in U.S. Pat. No. 7,612,181, the disclosure of which is herein incorporated by reference in its entirety.

As depicted in FIG. 1, assembly of two light chains and two heavy chains results in the formation of a DVD immunoglobulin molecule, with various inter-chain and intra-chain disulfide bonds stabilizing the interactions of the light and heavy chains.

Aspects of the subject DVD immunoglobulin molecules include a first variable domain with antigen binding functionality. $V_L1$ and $V_H1$ sequences of the subject DVD immunoglobulin molecules are selected to specifically bind to a target, such as, e.g., an antigen on a tumor cell. Immunoglobulins can exert antitumor effects by inducing apoptosis, redirected cytotoxicity, interfering with ligand-receptor interactions, or preventing the expression of proteins that are critical to a neoplastic phenotype. In addition, immunoglobulins can target components of the tumor microenvironment, perturbing vital structures such as the formation of tumor-associated vasculature. Immunoglobulins can also target receptors whose ligands are growth factors, such as the epidermal growth factor receptor, thus inhibiting binding of natural ligands that stimulate cell to targeted tumor cells. Alternatively, immunoglobulins can induce ADCC, ADCP or CDC.

One of skill in the art will realize that tumor-associated antigens are known for virtually any type of cancer. Specific tumor-associated binding targets that can be targeted by the first variable domain of a subject DVD immunoglobulin molecule include, but are not limited to, HER2 (ERBB2), FOLR1, FOLR2, CD138, CD19, CD79A, CD79B, ROR1, ROR2, FCRM, CS1, GPA33, MSLN, CD52, CD20, CD3, CD4, CD8, CD20, CD21, CD22, CD23, CD30, CD33, CD38, CD44, CD56, CD70, BCMA, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR (ERBB1), HER3 (ERBB3), HER4 (ERBB4), ENO1, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NR0B1, NR0B2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, EGF, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB21P, DES, DNCL1, ELAC2, ENO2, ENO3, FASN, FLJ12584, F1125530, GAGEB1, GAGEC1, GGT1, GSTP1, HIP1, HUMCYT2A, II29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAIL COL4A3, IL8, LAMA5, NRP1, NRP2, STAB1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (NGF), NGFR, NME1 (NM23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), FGF1, FLRT1 (fibronectin), GABRP (GABAa), GNAS1, ID2, ITGA6 (a6 integrin), ITGB4 (b 4 integrin), KLFS (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94).

The amino acid sequences of a first variable domain region, which provides antigen binding functionality, can include chimeric, humanized, or human amino acid sequences. Any suitable combination of such sequences can be incorporated into a first variable domain of a subject DVD immunoglobulin molecule.

Antigen-binding variable region sequences can be selected from various monoclonal antibodies capable of binding specific targets and well known in the art. These include, but are not limited to anti-TNF antibody (U.S. Pat. No. 6,258,562), anti-IL-12 and or anti-IL-12p40 antibody (U.S. Pat. No. 6,914,128); anti-IL-18 antibody (US 2005/0147610 A1), anti-05, anti-CBL, anti-CD147, anti-gp120, anti-VLA4, anti-CD11a, anti-CD18, anti-VEGF, anti-CD40L, anti-Id, anti-ICAM-1, anti-CXCL13, anti-CD2, anti-EGFR, anti-TGF-beta 2, anti-E-selectin, anti-Fact VII, anti-Her2/neu, anti-F gp, anti-CD11/18, anti-CD14, anti-ICAM-3, anti-CD80, anti-CD4, anti-CD3, anti-CD23, anti-beta2-integrin, anti-alpha4beta7, anti-CD52, anti-HLA DR, anti-CD22, anti-CD20, anti-MIF, anti-CD64 (FcR), anti-TCR alpha beta, anti-CD2, anti-Hep B, anti-CA 125, anti-EpCAM, anti-gp120, anti-CMV, anti-IgE, anti-CD25, anti-CD33, anti-HLA, anti-VNRintegrin, anti-IL-1alpha, anti-IL-1beta, anti-IL-1 receptor, anti-IL-2 receptor, anti-IL-4, anti-IL4 receptor, anti-IL5, anti-IL-5 receptor, anti-IL-6, anti-IL-8, anti-IL-9, anti-IL-13, anti-IL-13 receptor, anti-IL-17, and anti-IL-23 (see Presta LG. 2005 Selection, design, and engineering of therapeutic antibodies J Allergy Clin Immunol. 116:731-6 and Clark, M., "Antibodies for Therapeutic Applications," Department of Pathology, Cambridge University, UK, 15 Oct. 2000, published online at M. Clark's home page at the website for the Department of Pathology, Cambridge University).

Antigen-binding variable region sequences can also be selected from various therapeutic antibodies approved for use, in clinical trials, or in development for clinical use. Such therapeutic antibodies include, but are not limited to, RITUXAN®, IDEC/Genentech/Roche) (see for example U.S. Pat. No. 5,736,137), a chimeric anti-CD20 antibody approved to treat Non-Hodgkin's lymphoma; HUMAX-CD20®, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"), trastuzumab (HERCEPTIN®, Genentech) (see for example U.S. Pat. No. 5,677,171), a humanized anti-Her2/neu antibody approved to treat breast cancer; pertuzumab (rhuMab-2C4, OMNITARG®), currently being developed by Genentech; an anti-Her2 antibody described in U.S. Pat. No. 4,753,894; cetuximab (ERBITUX®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HUMAX-EGFR™ (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4): 315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2): 228-35; Modjtahedi et al, 2003, Int J Cancer, 105(2):273-80); TheraCIM hR3 (YM Biosciences, Canada and Centro de Immunologia Molecular, Cuba (U.S. Pat. Nos. 5,891,996; 6,506,883; Mateo et al, 1997, Immunotechnology, 3(1):71-81); mAb-806 (Ludwig Institute for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Scancell) (PCT WO 01/88138); alemtuzumab (CAMPATH®, Millennium), a humanized monoclonal antibody currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (ZEVALIN®), an anti-CD20 antibody developed by IDEC/ Schering AG, gemtuzumab ozogamicin (MYLOTARG®), an anti-CD33 (p67 protein) antibody developed by Celltech/ Wyeth, alefacept (AMEVIVE®), an anti-LFA-3 Fc fusion developed by Biogen), abciximab (REOPRO®), developed by Centocor/Lilly, basiliximab (SIMULECT®), developed by Novartis, palivizumab (SYNAGIS®), developed by Medimmune, infliximab (REMICADE®), an anti-TNFalpha antibody developed by Centocor, adalimumab (HU-MIRA®), an anti-TNFalpha antibody developed by Abbott, HUMICADE®, an anti-TNFalpha antibody developed by Celltech, etanercept (ENBREL®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, ANTEGREN® (natalizumab), an anti-alpha-4-beta-1 (VLA4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-02 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LYMPHOSTAT-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., AVASTIN® bevacizumab, rhuMAb-VEGF, an anti-VEGF antibody being developed by Genentech, an anti-HER receptor family antibody being developed by Genentech, Anti-Tissue Factor (ATF), an anti-Tissue Factor antibody being developed by Genentech, XOLAIR® (Omalizumab), an anti-IgE antibody being developed by Genentech, RAPTIVA® (Efalizumab), an anti-CD11a antibody being developed by Genentech and Xoma, MLN-02 Antibody (formerly LDP-02), being developed by Genentech and Millennium Pharmaceuticals, HUMAX CD4®, an anti-CD4 antibody being developed by Genmab, HUMAX™-IL15, an anti-IL15 antibody being developed by Genmab and Amgen, HUMAX™-Inflam, being developed by Genmab and Medarex, HUMAX™-Cancer, an anti-Heparanase I antibody being developed by Genmab and Medarex and Oxford GlycoSciences, HUMAX™-Lymphoma, being developed by Genmab and Amgen, HUMAX™-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-CIDE® (labetuzumab), an anti-carcinoembryonic antigen (CEA) antibody being developed by Immunomedics, LYMPHOCIDE® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, OSIDEM® (IDM-1), and anti-Her2 antibody being developed by Medarex and Immuno-Designed Molecules, HUMAX®-CD4, an anti-CD4 antibody being developed by Medarex and Genmab, HuMax-IL15, an anti-IL15 antibody being developed by Medarex and Genmab, CNTO 148, an anti-TNFa antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, NUVION® (visilizumab), an anti-CD3 antibody being developed by Protein Design Labs, HUZAF®, an anti-gamma interferon antibody being developed by Protein Design Labs, Anti-a 5β1 Integrin, being developed by Protein Design Labs, anti-IL-12, being developed by Protein Design Labs, ING-1, an anti-Ep-CAM antibody being developed by Xoma, XOLAIR® (Omalizumab) a humanized anti-IgE antibody developed by Genentech and Novartis, and MLN01, an anti-Beta2 integrin antibody being developed by Xoma. All of the above-cited references in this paragraph are expressly incorporated herein by reference.

Aspects of a subject DVD immunoglobulin molecule include a second variable domain from a 38C2 antibody, which includes a reactive lysine residue. A 38C2 antibody is described, for example, in U.S. Pat. No. 8,252,902, the disclosure of which is herein incorporated by reference in its entirety. Briefly, a heavy chain variable region of the 38C2 antibody includes a single, uniquely reactive lysine residue that can react with a linker, thereby providing an attachment point for conjugation with a drug moiety. As such, immunoglobulin molecules that include a variable domain of the 38C2 antibody contain two such attachment points (one on each heavy chain) that can be used for conjugation with a drug moiety. Once a reactive lysine residue has been conjugated to a linker, the binding functionality of the 38C2 variable domain is lost, meaning that the variable domain no longer binds to a target. As such, while not being limited by any particular theory, a variable domain of 38C2 antibody that is used in the subject DVD immunoglobulin molecules provides an attachment point for conjugation, but does not provide antigen binding functionality.

An amino acid sequence of a light chain variable domain ($V_L$) of a humanized 38C2 antibody is provided in SEQ ID NO: 3. An amino acid sequence of a heavy chain variable domain ($V_H$) of a humanized 38C2 antibody is provided in SEQ ID NO: 4.

In some aspects, a subject DVD immunoglobulin molecule includes a light chain variable domain sequence of a humanized 38C2 antibody (SEQ ID NO: 3) as a $V_L$2 domain sequence. In some aspects, a subject DVD immunoglobulin molecule includes a $V_L2$ domain sequence that is substantially similar to SEQ ID NO: 3, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 3.

In some aspects, a subject DVD immunoglobulin molecule includes a heavy chain variable domain sequence of a humanized 38C2 antibody (SEQ ID NO: 4) as a $V_H2$ domain sequence. In some aspects, a subject DVD immunoglobulin molecule includes a $V_H2$ domain sequence that is substantially similar to SEQ ID NO: 4, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 4, and includes a reactive lysine residue.

A subject DVD immunoglobulin molecule can encompass chimeric, humanized and human immunoglobulin sequences, and in some aspects, can contain any mixture thereof. For example, in some aspects, a DVD immunoglobulin molecule can include a chimeric first variable domain, and can include a human second variable domain. In some aspects, a DVD immunoglobulin molecule can include a humanized first variable domain, and can contain a human second variable domain. Any suitable combination of chimeric, humanized and human immunoglobulin sequences can be utilized in the subject DVD immunoglobulin molecules.

In some aspects, a DVD immunoglobulin of the invention can be modified with respect to effector function, e.g., so as to enhance ADCC, ADCP or CDC of the immunoglobulin. This can be achieved by introducing one or more amino acid substitutions in an Fc region of an immunoglobulin. Alternatively or additionally, cysteine residue(s) can be introduced in the Fc region, thereby allowing inter-chain disulfide bond formation in this region. An immunoglobulin thus generated can have improved internalization capability and/or increased ADCC, ADCP or CDC. See Caron et al., *J. Exp Med.* 176:1191-1195 (1992) and Shopes, B. *J. Immunol.* 148:2918-2922 (1992). To increase a serum half-life of an immunoglobulin, a salvage receptor binding epitope can be incorporated into an immunoglobulin (especially an immunoglobulin fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Figure 2:
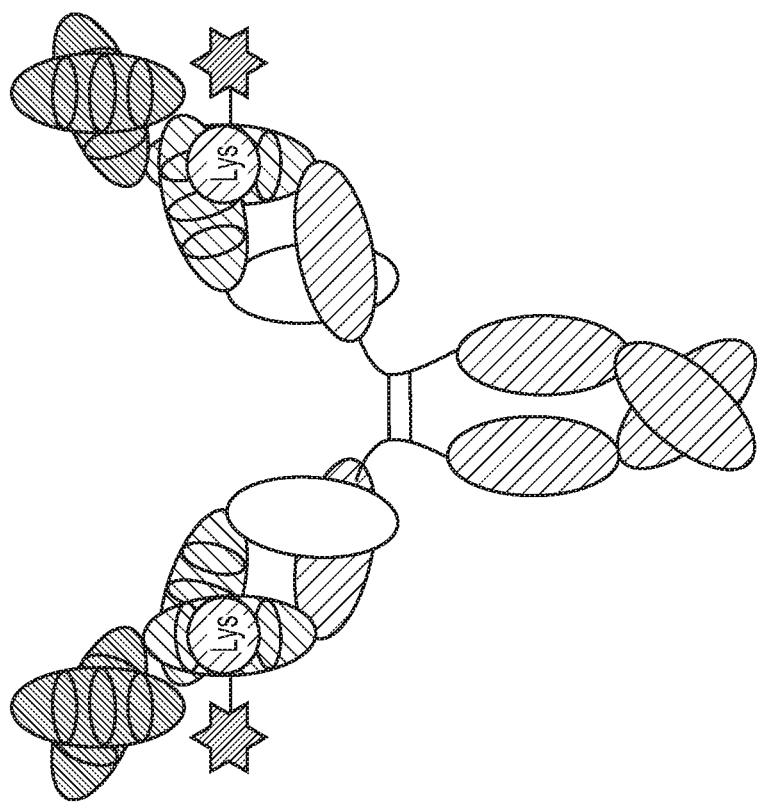
FIG. 2 is a schematic illustration of a dual variable domain immunoconjugate that has a drug moiety attached to a reactive lysine residue on each heavy chain.

As depicted in FIG. 2, a DVD immunoglobulin molecule in accordance with aspects of the invention includes a first variable domain that provides antigen binding functionality, and a second variable domain from a 38C2 antibody, which includes a single, uniquely reactive lysine residue that can be conjugated to a linker.

Figure 3:
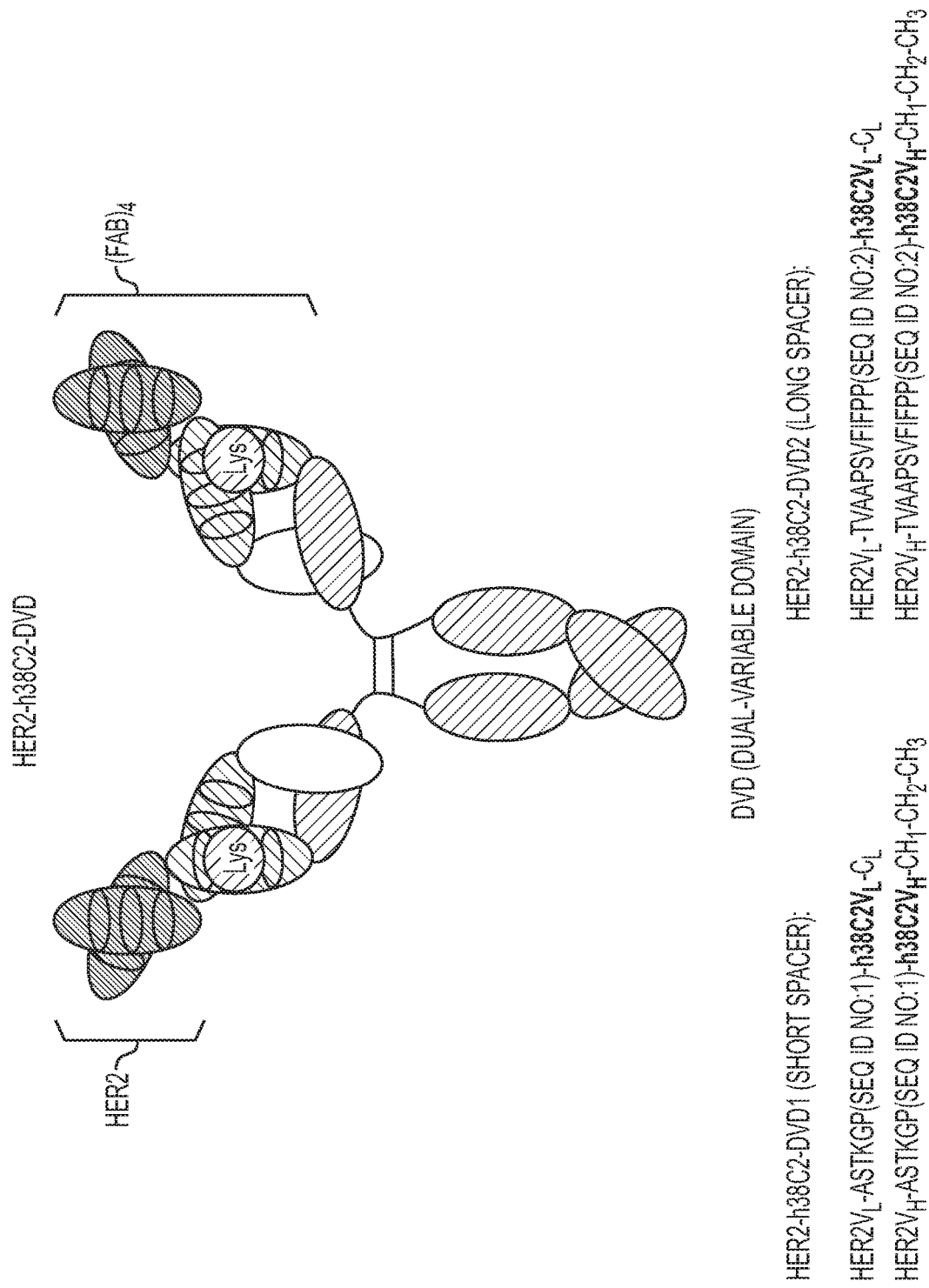
FIG. 3 is a schematic illustration of a HER2-h38C2-DVD1 and HER2-h38C2-DVD2 immunoconjugate.

In one specific aspect, a DVD immunoglobulin includes a first variable domain that binds to HER2, and includes a humanized 38C2 antibody variable domain as a second variable domain. The variable domains are connected on each light and heavy chain with a peptide linker sequence ASTKGP (SEQ ID NO: 1). This particular aspect is referred to as "HER2-h38C2-DVD1" and is depicted in FIG. 3. A light chain amino acid sequence of this aspect is provided in SEQ ID NO: 5. A heavy chain amino acid sequence of this aspect is provided in SEQ ID NO: 6. In some aspects, a subject HER2-h38C2-DVD1 immunoglobulin molecule includes a light chain amino acid sequence that is substantially similar to SEQ ID NO: 5, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 5. In some aspects, a subject HER2-h38C2-DVD1 immunoglobulin molecule includes a heavy chain amino acid sequence that is substantially similar to SEQ ID NO: 6, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 6, and includes a reactive lysine residue.

In another specific aspect, a DVD immunoglobulin includes a first variable domain that binds to HER2, and includes a humanized 38C2 antibody variable domain as a second variable domain. The variable domains are connected on each light and heavy chain with a peptide linker sequence TVAAPSVFIFPP (SEQ ID NO: 2). This particular aspect is referred to as "HER2-h38C2-DVD2" and is depicted in FIG. 3. A light chain amino acid sequence of this aspect is provided in SEQ ID NO: 7. A heavy chain amino acid sequence of this aspect is provided in SEQ ID NO: 8. In some aspects, a subject HER2-h38C2-DVD2 immunoglobulin molecule includes a light chain amino acid sequence that is substantially similar to SEQ ID NO: 7, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 7. In some aspects, a subject HER2-h38C2-DVD2 immunoglobulin molecule includes a heavy chain amino acid sequence that is substantially similar to SEQ ID NO: 8, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 8, and includes a reactive lysine residue.

Figure 4:
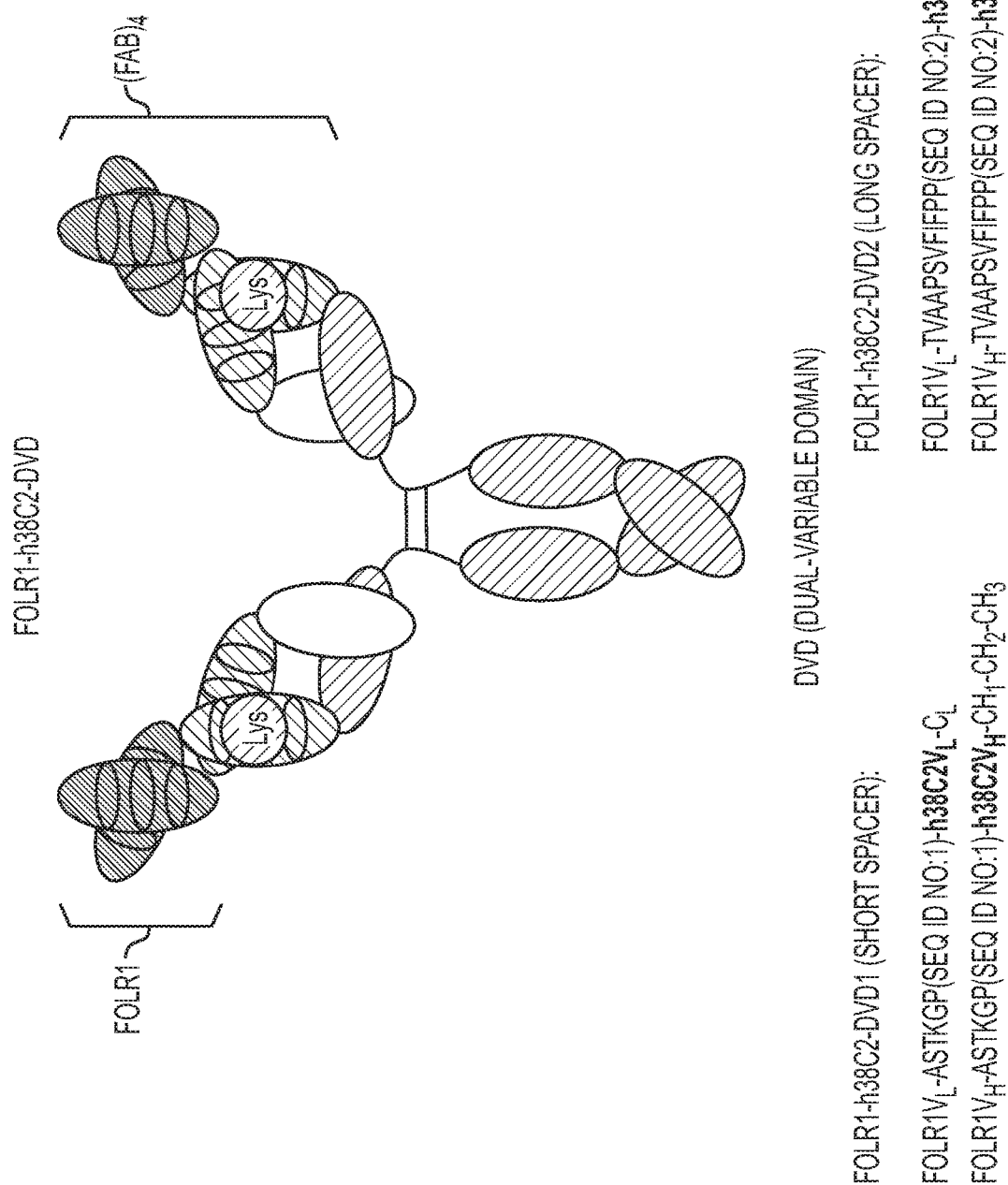
FIG. 4 is a schematic illustration of an FOLR1-h38C2-DVD1 and FOLR1-h38C2-DVD2 immunoconjugate.

In one specific aspect, a DVD immunoglobulin includes a first variable domain from an IMGN-853 anti-FOLR1 antibody (Immunogen, Waltham Mass.), which binds to FOLR1, and includes a humanized 38C2 antibody variable domain as a second variable domain. The variable domains are connected on each light and heavy chain with a peptide linker sequence ASTKGP (SEQ ID NO: 1). This particular aspect is referred to as "IMGN-853 FOLR1-h38C2-DVD1" and is schematically depicted in FIG. 4. A light chain amino acid sequence of this aspect is provided in SEQ ID NO: 9. A heavy chain amino acid sequence of this aspect is provided in SEQ ID NO: 10. In some aspects, a subject IMGN-853 FOLR1-h38C2-DVD1 immunoglobulin molecule includes a light chain amino acid sequence that is substantially similar to SEQ ID NO: 9, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 9. In some aspects, a subject IMGN-853 FOLR1-h38C2-DVD1 immunoglobulin molecule includes a heavy chain amino acid sequence that is substantially similar to SEQ ID NO: 10, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 10, and includes a reactive lysine residue.

In another specific aspect, a DVD immunoglobulin includes a first variable domain from an IMGN-853 anti-FOLR1 antibody (Immunogen, Waltham Mass.), which binds to FOLR1, and includes a humanized 38C2 antibody variable domain as a second variable domain. The variable domains are connected on each light and heavy chain with a peptide linker sequence TVAAPSVFIFPP (SEQ ID NO: 2). This particular aspect is referred to as "IMGN-853 FOLR1-h38C2-DVD2" and is schematically depicted in FIG. 4. A light chain amino acid sequence of this aspect is provided in SEQ ID NO: 11. A heavy chain amino acid sequence of this aspect is provided in SEQ ID NO: 12. In some aspects, a subject IMGN-853 FOLR1-h38C2-DVD2 immunoglobulin molecule includes a light chain amino acid sequence that is substantially similar to SEQ ID NO: 11, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 11. In some aspects, a subject IMGN-853 FOLR1-h38C2-DVD2 immunoglobulin molecule includes a heavy chain amino acid sequence that is substantially similar to SEQ ID NO: 12, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 12, and includes a reactive lysine residue.

In one specific aspect, a DVD immunoglobulin includes a first variable domain from a farletuzumab antibody (Morphotek, Inc., Exton Pa.), which binds to FOLR1, and includes a humanized 38C2 antibody variable domain as a second variable domain. The variable domains are connected on each light and heavy chain with a peptide linker sequence ASTKGP (SEQ ID NO: 1). This particular aspect is referred to as "farletuzumab FOLR1-h38C2-DVD1" and is schematically depicted in FIG. 4. A light chain amino acid sequence of this aspect is provided in SEQ ID NO: 13. A heavy chain amino acid sequence of this aspect is provided in SEQ ID NO: 14. In some aspects, a subject farletuzumab FOLR1-h38C2-DVD1 immunoglobulin molecule includes a light chain amino acid sequence that is substantially similar to SEQ ID NO: 13, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 13. In some aspects, a subject farletuzumab FOLR1-h38C2-DVD1 immunoglobulin molecule includes a heavy chain amino acid sequence that is substantially similar to SEQ ID NO: 14, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 14, and includes a reactive lysine residue.

In another specific aspect, a DVD immunoglobulin includes a first variable domain from a farletuzumab antibody (Morphotek, Inc., Exton Pa.), and includes a humanized 38C2 antibody variable domain as a second variable domain. The variable domains are connected on each light and heavy chain with a peptide linker sequence TVAAPSVFIFPP (SEQ ID NO: 2). This particular aspect is referred to as "farletuzumab FOLR1-h38C2-DVD2" and is schematically depicted in FIG. 4. A light chain amino acid sequence of this aspect is provided in SEQ ID NO: 15. A heavy chain amino acid sequence of this aspect is provided in SEQ ID NO: 16. In some aspects, a subject farletuzumab FOLR1-h38C2-DVD2 immunoglobulin molecule includes a light chain amino acid sequence that is substantially similar to SEQ ID NO: 15, for example, has at least about 80% amino acid sequence identity, alternatively has at least about 81%, 82%, 83%, 84%, 85%, 86%, 8'7%, 88%, 89%, 90%, 91%, 92%, 93%, 94%, 95%, 96%, 97%, 98%, or 99% amino acid sequence identity to SEQ ID NO: 15. In some aspects, a subject farletuzumab FOLR1-h38C2-DVD2 immunoglobulin molecule includes a heavy chain amino acid sequence that is substantially similar to SEQ ID NO: 16, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 16, and includes a reactive lysine residue.

Figure 5:
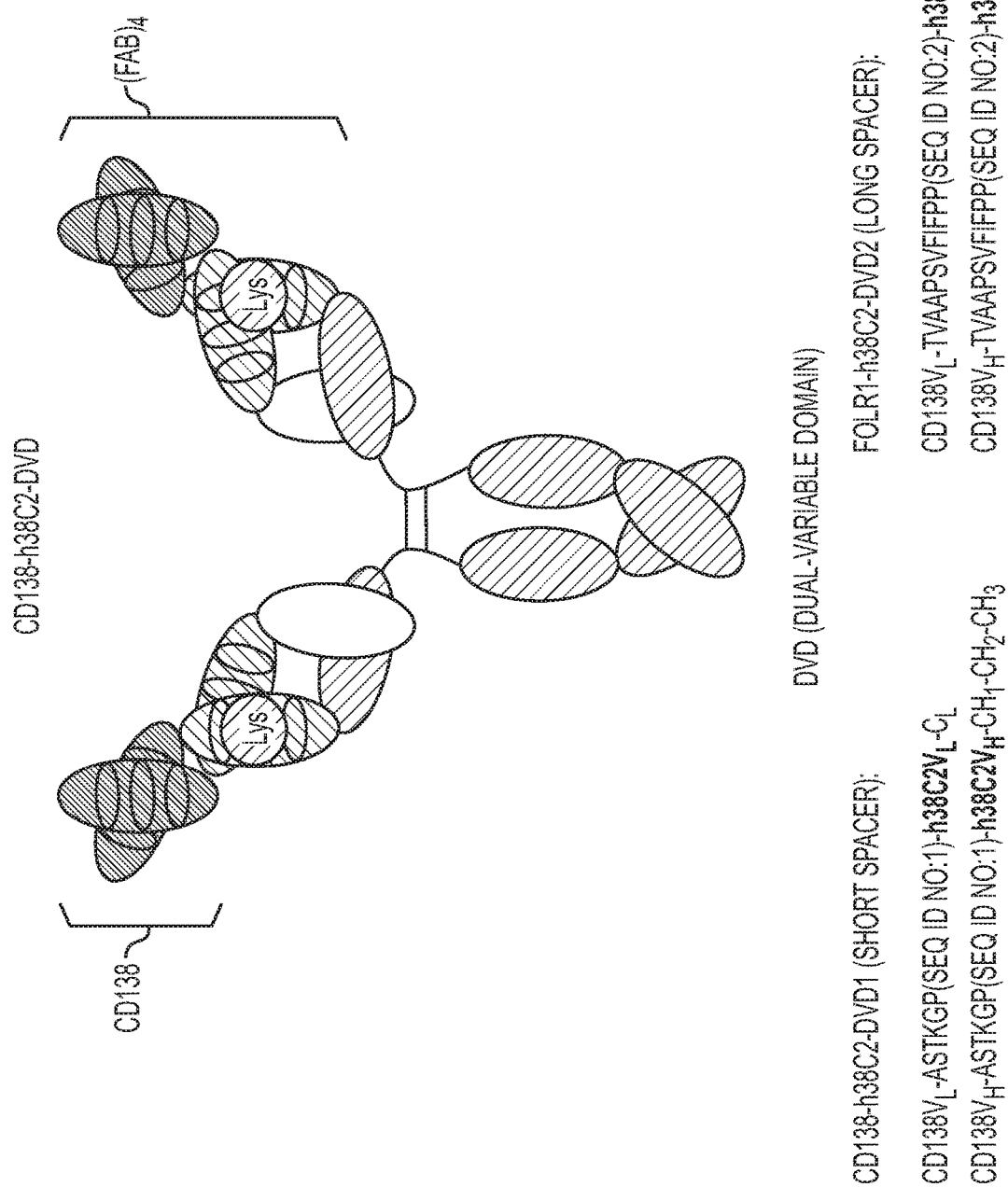
FIG. 5 is a schematic illustration of a CD138-h38C2-DVD1 and CD138-h38C2-DVD2 immunoconjugate.

In one specific aspect, a DVD immunoglobulin includes a first variable domain that binds to CD138, and includes a humanized 38C2 antibody variable domain as the second variable domain. The variable domains are connected on each light and heavy chain with a peptide linker sequence ASTKGP (SEQ ID NO: 1). This particular aspect is referred to as "CD138-h38C2-DVD1" and is depicted in FIG. 5. A light chain amino acid sequence of this aspect is provided in SEQ ID NO: 17. A heavy chain amino acid sequence of this aspect is provided in SEQ ID NO: 18. In some aspects, a subject CD138-h38C2-DVD1 immunoglobulin molecule includes a light chain amino acid sequence that is substantially similar to SEQ ID NO: 17, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 17. In some aspects, a subject CD138-h38C2-DVD1 immunoglobulin molecule includes a heavy chain amino acid sequence that is substantially similar to SEQ ID NO: 18, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 18, and includes a reactive lysine residue.

In another specific aspect, a DVD immunoglobulin includes a first variable domain that binds to CD138, and includes a humanized 38C2 antibody variable domain as a second variable domain. The variable domains are connected on each light and heavy chain with a peptide linker sequence TVAAPSVFIFPP (SEQ ID NO: 2). This particular aspect is referred to as "CD138-h38C2-DVD2" and is depicted in FIG. 5. A light chain amino acid sequence of this aspect is provided in SEQ ID NO: 19. A heavy chain amino acid sequence of this aspect is provided in SEQ ID NO: 20. In some aspects, a subject CD138-h38C2-DVD2 immunoglobulin molecule includes a light chain amino acid sequence that is substantially similar to SEQ ID NO: 19, for example, has at least about 80% amino acid sequence identity, alternatively has at least about 81%, 82%, 83%, 84%, 85%, 86%, 8'7%, 88%, 89%, 90%, 91%, 92%, 93%, 94%, 95%, 96%, 97%, 98%, or 99% amino acid sequence identity to SEQ ID NO: 19. In some aspects, a subject CD138-h38C2-DVD2 immunoglobulin molecule includes a heavy chain amino acid sequence that is substantially similar to SEQ ID NO: 20, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 20, and includes a reactive lysine residue.

In one specific aspect, a DVD immunoglobulin includes a first variable domain that binds to CD79b, and includes a humanized 38C2 antibody variable domain as the second variable domain. The variable domains are connected on each light and heavy chain with a peptide linker sequence ASTKGP (SEQ ID NO: 1). This particular aspect is referred to as "CD79b-h38C2-DVD1." A light chain amino acid sequence of this aspect is provided in SEQ ID NO: 21. A heavy chain amino acid sequence of this aspect is provided in SEQ ID NO: 22. In some aspects, a subject CD79b-h38C2-DVD1 immunoglobulin molecule includes a light chain amino acid sequence that is substantially similar to SEQ ID NO: 21, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 21. In some aspects, a subject CD79b-h38C2-DVD1 immunoglobulin molecule includes a heavy chain amino acid sequence that is substantially similar to SEQ ID NO: 22, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 22, and includes a reactive lysine residue.

In another specific aspect, a DVD immunoglobulin includes a first variable domain that binds to CD79b, and includes a humanized 38C2 antibody variable domain as a second variable domain. The variable domains are connected on each light and heavy chain with a peptide linker sequence TVAAPSVFIFPP (SEQ ID NO: 2). This particular aspect is referred to as "CD79b-h38C2-DVD2." A light chain amino acid sequence of this aspect is provided in SEQ ID NO: 23. A heavy chain amino acid sequence of this aspect is provided in SEQ ID NO: 24. In some aspects, a subject CD79b-h38C2-DVD2 immunoglobulin molecule includes a light chain amino acid sequence that is substantially similar to SEQ ID NO: 23, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 23. In some aspects, a subject CD79b-h38C2-DVD2 immunoglobulin molecule includes a heavy chain amino acid sequence that is substantially similar to SEQ ID NO: 24, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO: 24, and includes a reactive lysine residue.

Figure 6:
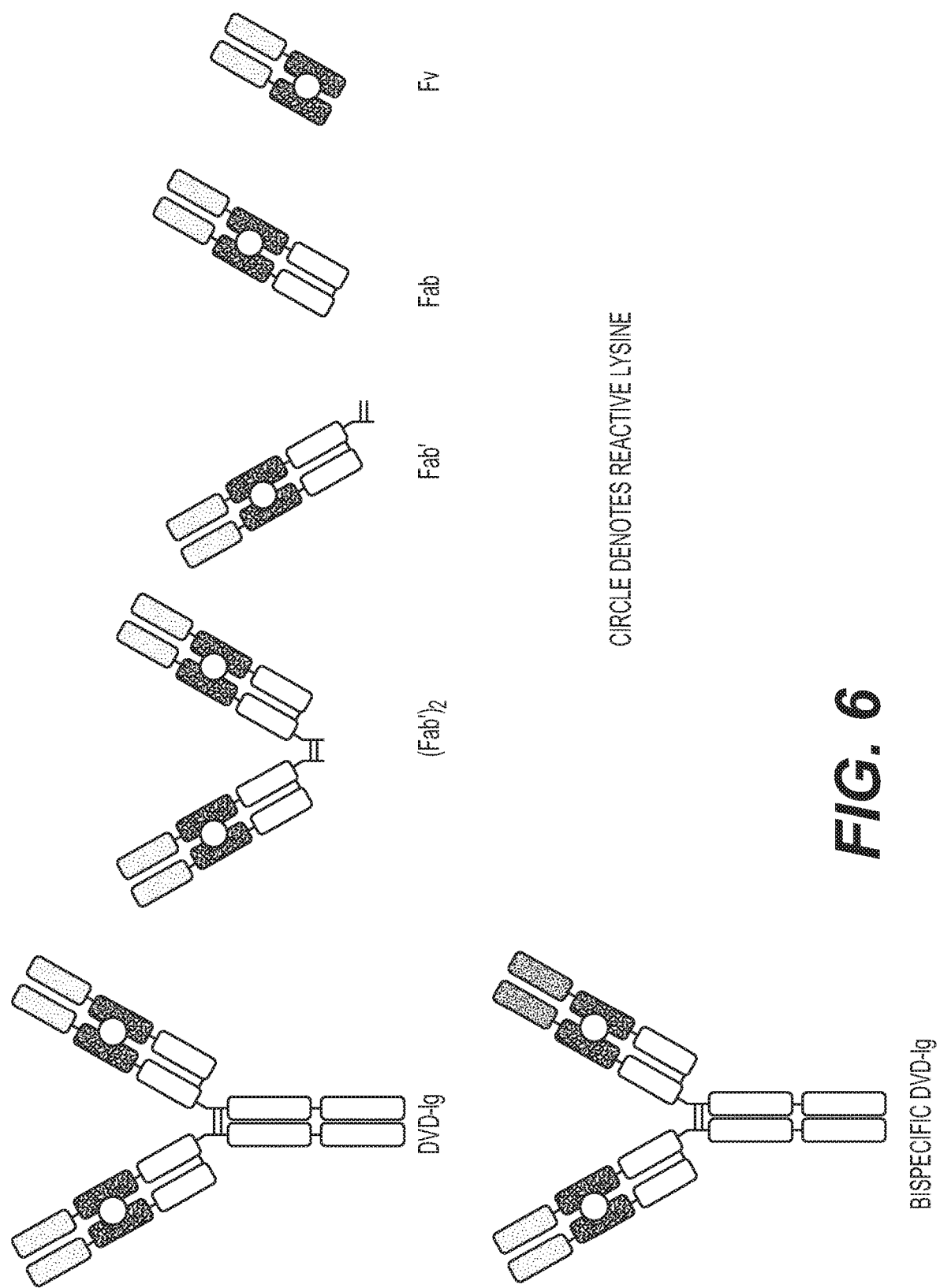
FIG. 6 is a schematic illustration of a dual variable domain immunoconjugate, various binding fragments thereof, and a bispecific dual variable domain immunoconjugate.

In certain aspects, a subject DVD immunoglobulin molecule is bispecific, in that one arm of the immunoglobulin includes a first variable domain with binding specificity for a first binding target, and the second arm includes a first variable domain with binding specificity for a second binding target. Such aspects provide the ability to bind to two different targets, thereby providing additional functionality. An illustrative bispecific DVD immunoglobulin molecule is depicted in FIG. 6.

In certain aspects, a subject DVD immunoglobulin molecule is bi-paratopic, in that one arm of the immunoglobulin includes a first variable domain with binding specificity for a first binding target, and the second arm includes a first variable domain with binding specificity for the same binding target, but a different binding epitope. Such aspects provide the ability to bind to the same target covering two different, but potentially somewhat overlapping binding epitopes, thereby providing target crosslinking functionality, triggering lysosomal trafficking after internalization.

In certain aspects, an immunoglobulin molecule is an intact immunoglobulin molecule that includes a first and second variable region, as described above, and also includes a $C_L$ domain on the light chain, as well as heavy chain constant domains $C_H1$, $C_H2$, and $C_H3$. A constant domain can comprise a native or non-native sequence, or an amino acid sequence variant thereof. In certain aspects, an immunoglobulin molecule can be an immunoglobulin fragment. Examples of immunoglobulin fragments include, but are not limited to, (Fab')$_2$, Fab', Fab, and Fv fragments, non-limiting examples of which are depicted in FIG. 6.

Production of DVD Immunoglobulins

DVD immunoglobulins of the present invention can be produced by any of a number of techniques known in the art. For example, expression from host cells, wherein expression vector(s) encoding the DVD heavy and/or DVD light chains is transfected into a host cell by standard techniques. Various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the DVD immunoglobulins of the invention in either prokaryotic or eukaryotic host cells, expression of DVD immunoglobulins in eukaryotic cells is preferable, and most preferable in mammalian host cells, because such eukaryotic cells (and in particular mammalian cells) are more likely than prokaryotic cells to assemble and secrete a properly folded and immunologically active DVD immunoglobulin.

Preferred mammalian host cells for expressing the recombinant immunoglobulins of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), Human Embryonic Kidney (HEK) cells, NS0 myeloma cells, COS cells and SP2 cells. When recombinant expression vectors encoding DVD immunoglobulins are introduced into mammalian host cells, the DVD immunoglobulins are produced by culturing the host cells for a period of time sufficient to allow for expression of the DVD immunoglobulins in the host cells or, more preferably, secretion of the DVD immunoglobulins into the culture medium in which the host cells are grown. DVD immunoglobulins can be recovered from the culture medium using standard protein purification methods.

In a preferred system for recombinant expression of DVD immunoglobulins of the invention, a recombinant expression vector encoding both the DVD heavy chain and the DVD light chain is introduced into dhfr-CHO cells by calcium phosphate-mediated transfection. Within the recombinant expression vector, the DVD heavy and light chain genes are each operatively linked to CMV enhancer/AdMLP promoter regulatory elements to drive high levels of transcription of the genes. A recombinant expression vector also carries a DHFR gene, which allows for selection of CHO cells that have been transfected with the vector using methotrexate selection/amplification. Selected transformant host cells are cultured to allow for expression of the DVD heavy and light chains and intact DVD immunoglobulin is recovered from the culture medium. Standard molecular biology and tissue culture techniques are used to prepare the recombinant expression vector, transfect the host cells, select for transformants, culture the host cells and recover the DVD immunoglobulin from the culture medium. In addition, aspects of the invention include a method of synthesizing a DVD immunoglobulin of the invention by culturing a host cell of the invention in a suitable culture medium until a DVD immunoglobulin of the invention is synthesized. A method can further comprise isolating the DVD immunoglobulin from the culture medium to yield an isolated immunoglobulin.

A feature of the subject DVD immunoglobulins is that they can be produced and purified in ways that are similar to conventional antibodies. Production of DVD immunoglobulins can result in a homogeneous, single major product with desired activity, without any sequence modification of the constant region or chemical modifications of any kind.

Linkers

Aspects of a subject immunoconjugate include linkers, which can comprise one or more linker components. Linkers in accordance with aspects of the invention serve to attach a cargo moiety (e.g., a drug moiety) to a DVD-Ig, and can employ any suitable chemistry. Various types of linker functionality can be included in the subject immunoconjugates, including but not limited to cleavable linkers, and non-cleavable linkers, as well as reversible linkers and irreversible linkers.

Figure 7:
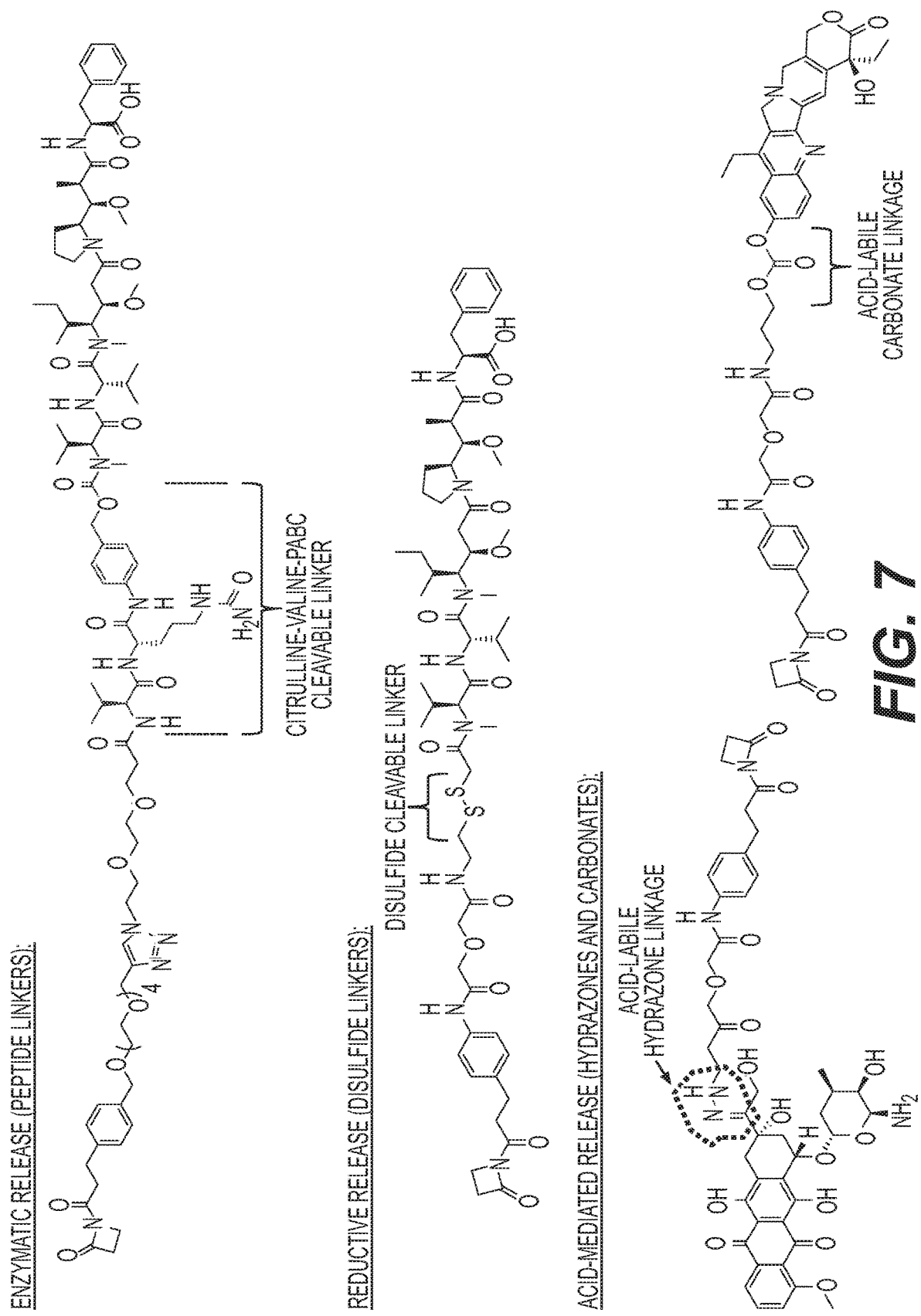
FIG. 7 depicts various non-limiting examples of cleavable linkers.

Cleavable linkers are those that rely on processes inside a target cell to liberate a drug moiety, such as reduction in the cytoplasm, exposure to acidic conditions in a lysosome or endosome, or cleavage by specific enzymes (e.g. proteases) within the cell. As such, cleavable linkers allow an attached drug moiety to be released in its original form after an immunoconjugate has been internalized and processed inside a target cell. Cleavable linkers include, but are not limited to, those whose bonds can be cleaved by enzymes (e.g., peptide linkers); reducing conditions (e.g., disulfide linkers); or acidic conditions (e.g., hydrazones and carbonates). Non-limiting examples of cleavable linkers are provided in FIG. 7.

Figure 8:
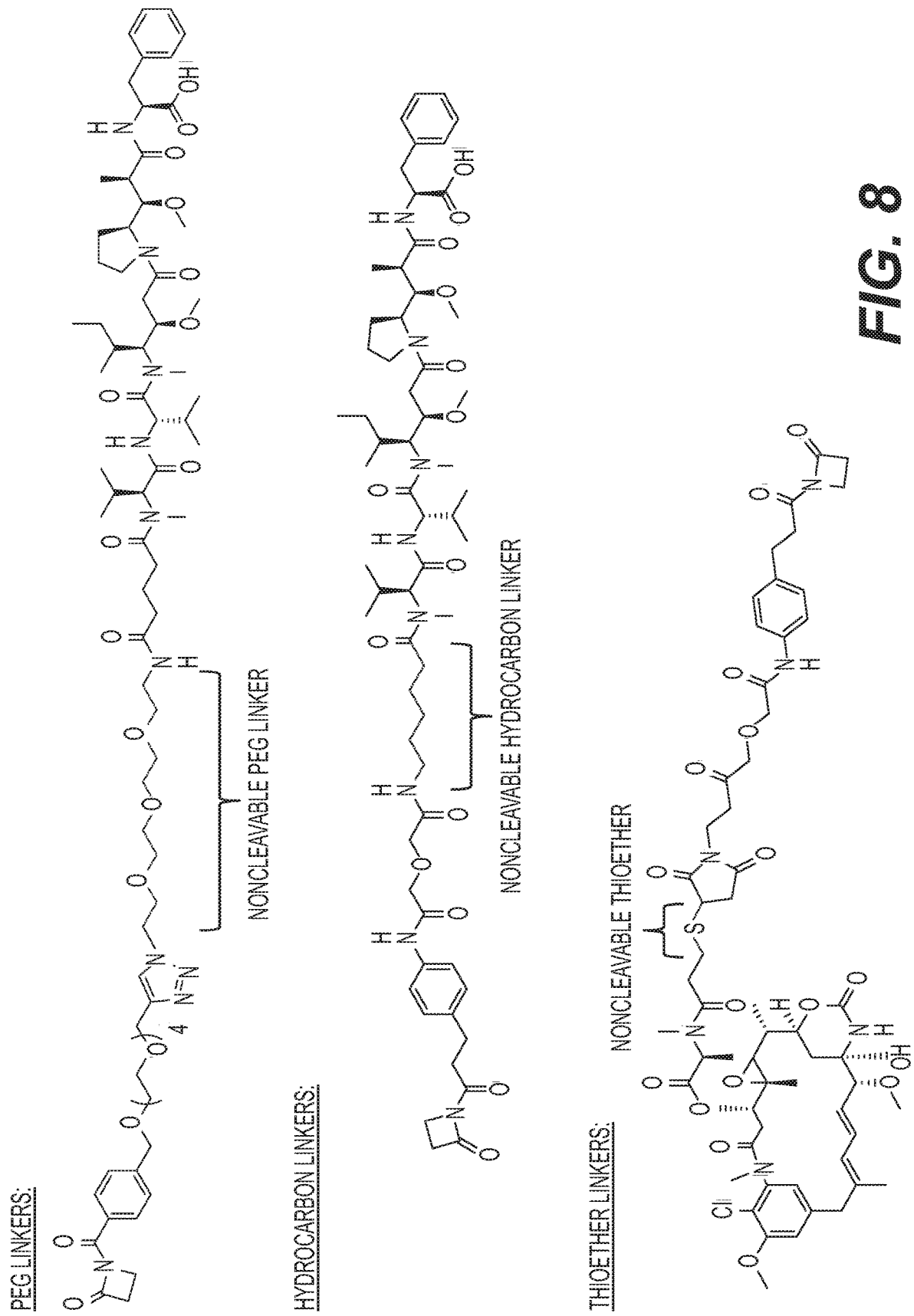
FIG. 8 depicts various non-limiting examples of non-cleavable linkers.

Non-cleavable linkers utilize catabolic degradation of an immunoconjugate for the release of the drug moiety. A released drug moiety generally retains the linker as well as the amino acid residue of the immunoglobulin to which the linker was conjugated. Non-cleavable linkers include, but are not limited to, PEG linkers, hydrocarbon linkers, and thioether linkers. Non-limiting examples of non-cleavable linkers are provided in FIG. 8.

Figure 9:
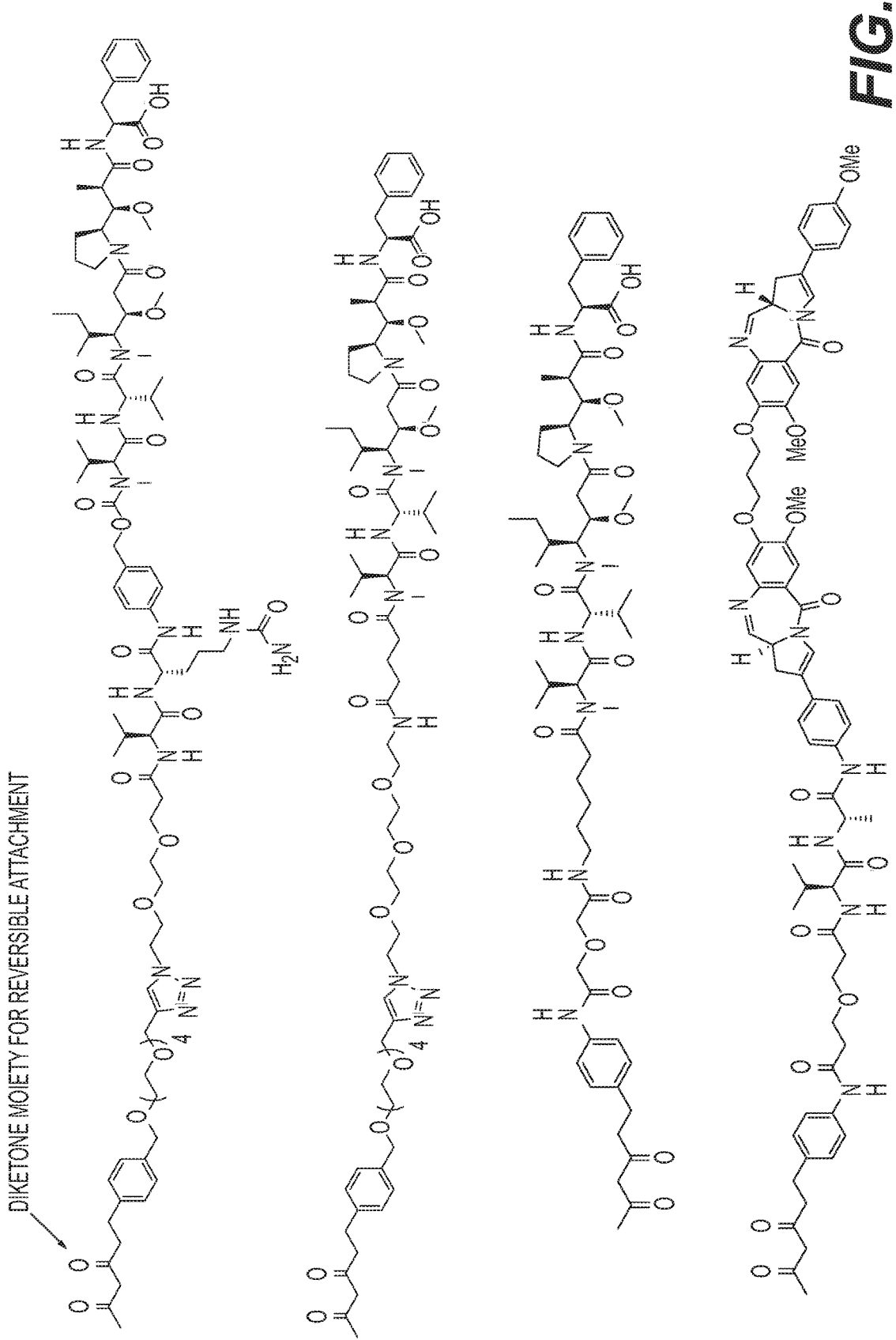
FIG. 9 depicts various non-limiting examples of reversible linkers.
Figure 10:
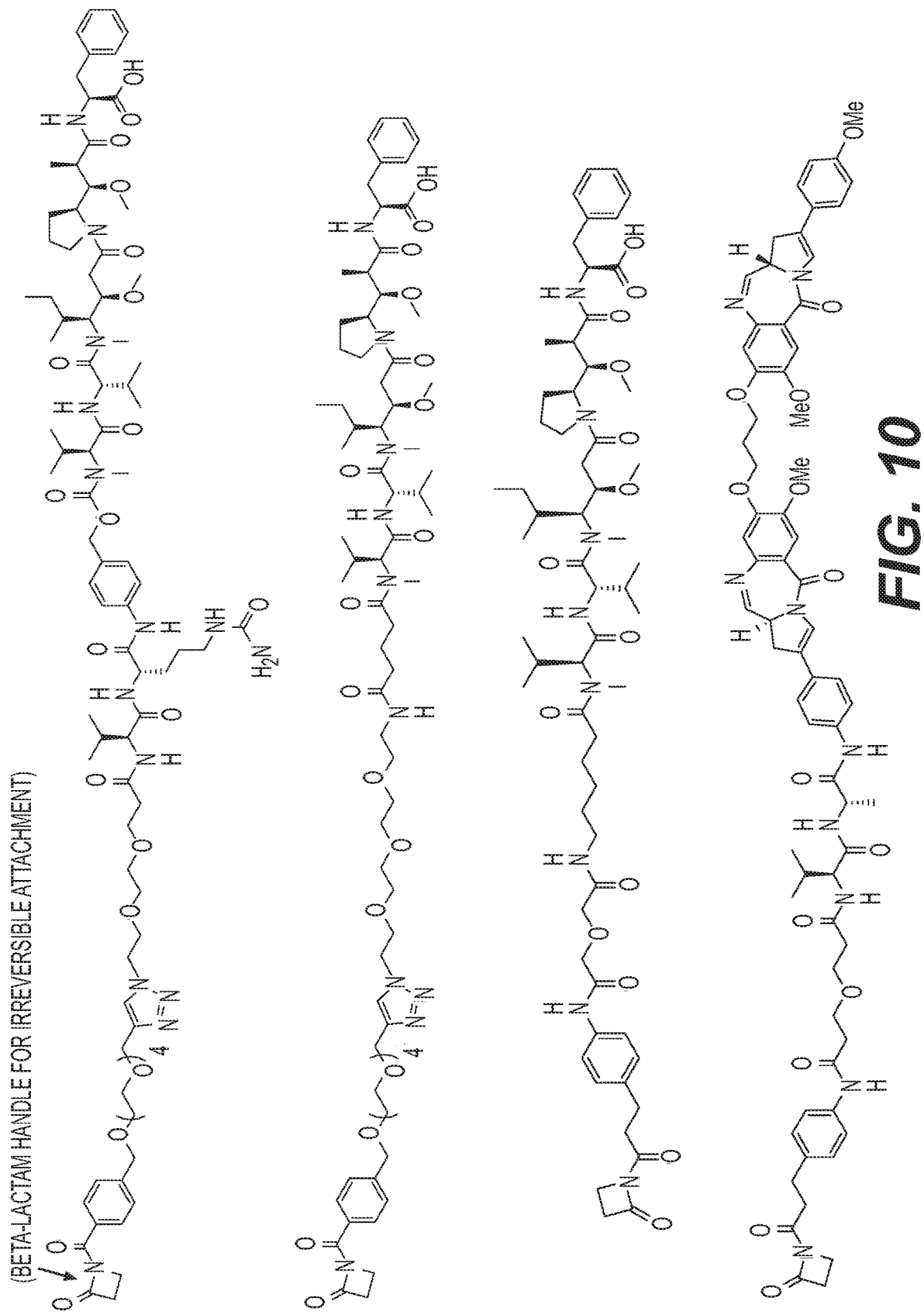
FIG. 10 depicts various non-limiting examples of irreversible linkers.
Figure 13:
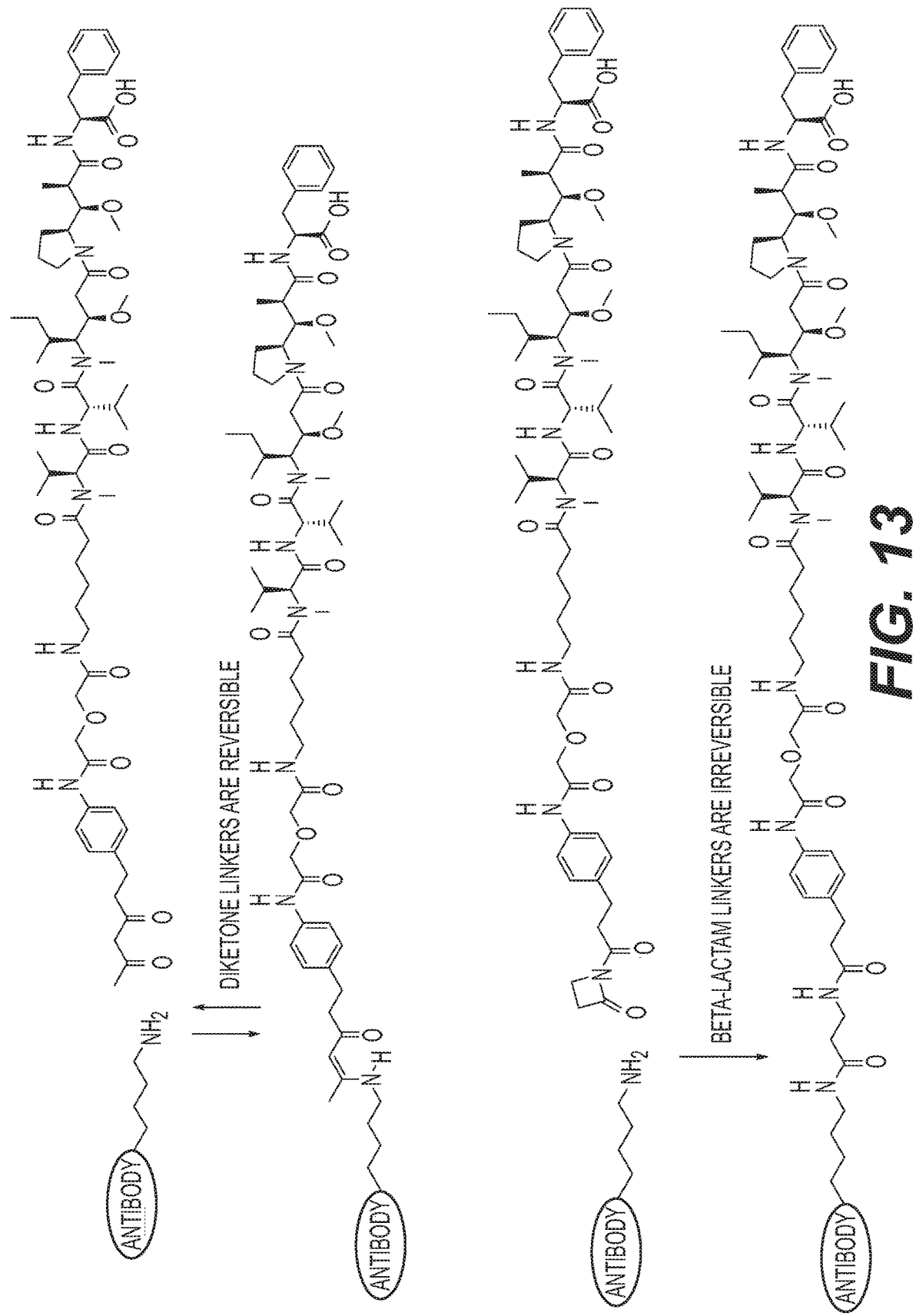
FIG. 13 depicts various non-limiting examples of linker reactions with an immunoglobulin using reversible and irreversible linkers.

Aspects of a subject immunoconjugate can also include reversible and irreversible linkers. Reversible linkers utilize chemical bonds that can readily be broken, or reversed, using suitable reagents. As such, after the formation of a reversible linker, the linker can be broken in a desired position by treatment with a reagent, thereby releasing the immunoglobulin molecule from the linker. Non-limiting examples of reversible linkers are provided in FIG. 9, and include, for example, diketone moieties. Irreversible linkers utilize chemical bonds that cannot readily be broken or reversed after their formation. As such, after the formation of an irreversible linker, an immunoglobulin molecule cannot readily be released. Non-limiting examples of irreversible linkers are provided in FIG. 10, and include, for example, β-lactam moieties. Example linker reactions in which an immunoglobulin is conjugated to a reversible or irreversible linker are depicted in FIG. 13.

In addition to β-lactam and diketone moieties, in some aspects, other moieties, such as, e.g., vinyl diketones and pro-vinyl diketones can be used for conjugation. In some aspects, electrophilic moieties (handles) can be used, either alone or in combination, with such moieties. Electrophilic moieties can be used for site-specific conjugation with the single, uniquely reactive lysine of an h38C2 variable domain, and can also be used for non-specific conjugation after an h38C2 lysine has been conjugated to a drug moiety. Non-limiting examples of other moieties include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), and those resulting from conjugation with linker reagents: N-Succinimidyl 4-(2-pyridylthio) pentanoate forming linker moiety 4-mercaptopentanoic acid ("SPP"), N-succinimidyl 4-(N-maleimidomethyl) cyclohexane-1 carboxylate forming linker moiety 4-((2,5-dioxopyrrolidin-1-yl)methyl)cyclohexanecarboxylic acid ("SMCC", also referred to herein as "MCC"), 2,5-dioxopyrrolidin-1-yl 4-(pyridin-2-yldisulfanyl) butanoate forming linker moiety 4-mercaptobutanoic acid ("SPDB"), N-Succinimidyl (4-iodo-acetyl) aminobenzoate ("STAB"), ethyleneoxy —$CH_2CH_2O$— as one or more repeating units ("EO" or "PEO"). Further information is provided in Sinha et al., Nat. Protoc. 2, 449-456 (2007), the disclosure of which is incorporated by reference herein in its entirety.

In some aspects, a linker component can comprise an amino acid unit. In one such aspect, an amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. Non-limiting examples of amino acid units include, but are not limited to, a dipeptide, a tripeptide, a tetrapeptide, and a pentapeptide. Non-limiting examples of dipeptides include: valine-citrulline (vc or val-cit), alanine-phenylalanine (af or ala-phe); phenylalanine-lysine (fk or phe-lys); or N-methyl-valine-citrulline (Me-val-cit). Non-limiting examples of tripeptides include: glycine-valine-citrulline (gly-val-cit) and glycine-glycine-glycine (gly-gly-gly). An amino acid unit can comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some aspects, a linker L can be a branched or dendritic type linker for covalent attachment of more than one drug moiety through a branching, multifunctional linker moiety to an immunoglobulin (Sun et al (2002) Bioorganic & Medicinal Chemistry Letters 12:2213-2215; Sun et al (2003) Bioorganic & Medicinal Chemistry 11:1761-1768). Non-limiting examples of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499). Branched linkers can increase the molar ratio of drug to immunoglobulin, i.e., loading, which is related to the potency of the ADC. Thus, for example, where an immunoglobulin bears only one reactive amino acid residue for conjugation, a multitude of drug moieties can be attached through a branched linker.

Linker components, including stretcher, spacer, and amino acid units, can be synthesized by methods known in the art, such as those described in US Patent Publication No. 2005/0238649 A1, which is herein incorporated by reference in its entirety.

Cargo Moieties

Aspects of the invention include immunoglobulin molecules that are conjugated to one or more cargo moieties via a linker, as described above. Cargo moieties broadly include, but are not limited to, biologically active moieties, such as drug moieties and expression modifying moieties, as well as non-biologically active moieties, such as detectable moieties (e.g., detectable labels). Each of these moieties is further described herein.

Non-limiting examples of drug moieties include cytotoxic and cytostatic agents that are capable of killing a target cell, or arresting the growth of a target cell. In some aspects, drug moieties include toxins, chemotherapeutic agents, antibiotics, radioactive isotopes, chelated radioactive isotopes, and nucleolytic enzymes.

In some aspects, a drug moiety is selected from the group consisting of auristatin; dolostatin; cemadotin; MMAF; MMAE; maytansinoids (including, but not limited to DM1, DM3 and DM4); pyrrolobenzodiazepines (PBDs, including, but not limited to monomeric and dimeric PBDs); enediynes (including but not limited to calicheamicins and tiancimycins); camptothecins (including but not limited to SN-38); and doxorubicin (including but not limited to MMDX or bioactivation products thereof, such as, e.g., PNU-159682).

In certain aspects, a drug moiety of the immunoconjugates of the present invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, a proteasome inhibitor, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

Further, a subject immunoglobulin (or binding fragment thereof) can be conjugated to a drug moiety that modifies a given biological response. Drug moieties are not to be construed as limited to classical chemical therapeutic agents. For example, a drug moiety can be a protein, peptide, or polypeptide possessing a desired biological activity. Such proteins can include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or a biological response modifier such as, for example, a lymphokine.

In some aspects, a drug moiety can be a cytotoxin, a drug (e.g., an immunosuppressant) or a radiotoxin. Examples of cytotoxins include but are not limited to, taxanes, DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety, taxon, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Drug moieties can also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). See, e.g., US Patent Publication No. 20090304721, which is incorporated herein by reference in its entirety.

Other non-limiting examples of cytotoxins that can be conjugated to the antibodies, antibody fragments (antigen binding fragments) or functional equivalents of the invention include duocarmycins, calicheamicins, maytansines and auristatins, and derivatives thereof.

Immunoglobulins, or binding fragments thereof, of the present invention can also be conjugated to a radioactive isotope or a chelated radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, lutetium-177, bismuth-213 and astatine-211. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain aspects, the macrocyclic chelator is 1,4,7,10-tetraazacyclododecane-N,N',N'',N'''-tetraacetic acid (DOTA) which can be attached to an immunoglobulin via a linker molecule.

In some aspects, a drug moiety includes a single drug unit, as described above. In other aspects, a drug moiety includes a plurality of identical drug units, such as 2, 3, 4, 5, 6, 7, 8, 9, or 10 drug units on the same drug moiety. In certain aspects, a drug moiety includes two different drug units on the same drug moiety. For example, in some aspects, a single drug moiety can include both an MMAF drug unit and a PBD monomer drug unit. Furthermore, in certain aspects, a subject immunoconjugate can include a first drug moiety conjugated to a first arm of the immunoconjugate, and a second drug moiety conjugated to the second arm of the immunoconjugate. As such, any of a variety of combinations of drug moieties can be conjugated to a subject DVD-Ig via a linker. Non-limiting examples of drug moieties are depicted in FIG. 14.

Expression modifying moieties include, but are not limited to, non-protein-coding RNA ("npcRNA"). In an aspect, an npcRNA includes, but is not limited to, a microRNA (miRNA), a miRNA precursor, a small interfering RNA (siRNA), a small RNA and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA). In one aspect, an siRNA comprises a length that ranges from about 20 to about 25 base pairs, such as from about 20 to about 24 base pairs, such as from about 21 to about 25 base pairs, or from about 22 to about 24 base pairs. In an aspect, a small RNA comprises a length that ranges from about 22 to about 26 base pairs, such as from about 22 to about 25 base pairs, such as from about 23 to about 26 base pairs, or from about 24 to about 25 base pairs.

A general description and review of siRNA technology can be found in: Resnier et al., "A review of the current status of siRNA nanomedicines in the treatment of cancer", Biomaterials 34 (2013) 6429-43, which is herein incorporated by reference in its entirety.

A general description and review of siRNA technology can also be found in: Song et al., "Antibody mediated in vivo delivery of small interfering RNAs via cell-surface receptors", Nature Biotechnology 23, 709-717 (2005), which is herein incorporated by reference in its entirety.

Detectable moieties include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Immunoconjugates

An aspect of the invention includes immunoconjugates, wherein a subject DVD-Ig is conjugated to one or more drug moieties via a linker. In some aspects, a subject immunoconjugate is generally described by the formula Ig-(L-D)$_n$, wherein Ig is a dual variable domain immunoglobulin molecule, L is a linker, D is a drug moiety, and n is an integer selected from 1 to 12, such as 2, 3, 4, 5, 6, 7, 8, 9, 10 or 11. In one aspect, n is 1 or 2.

Figure 15:
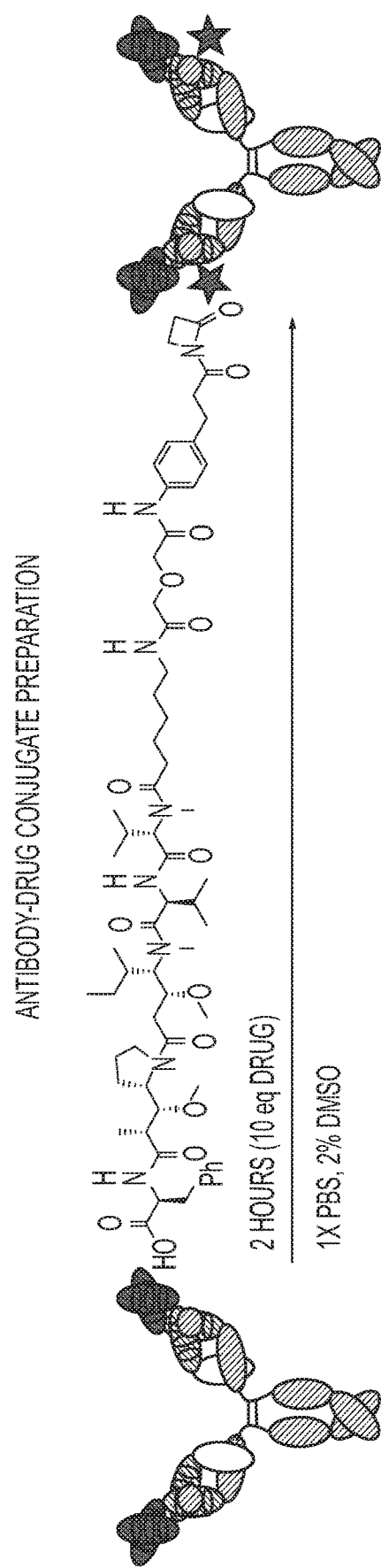
FIG. 15 is a schematic illustration of an immunoglobulin conjugation reaction, wherein conjugation takes place at the reactive lysine residues in the second variable domain (h38C2 variable domain).
Figure 16:
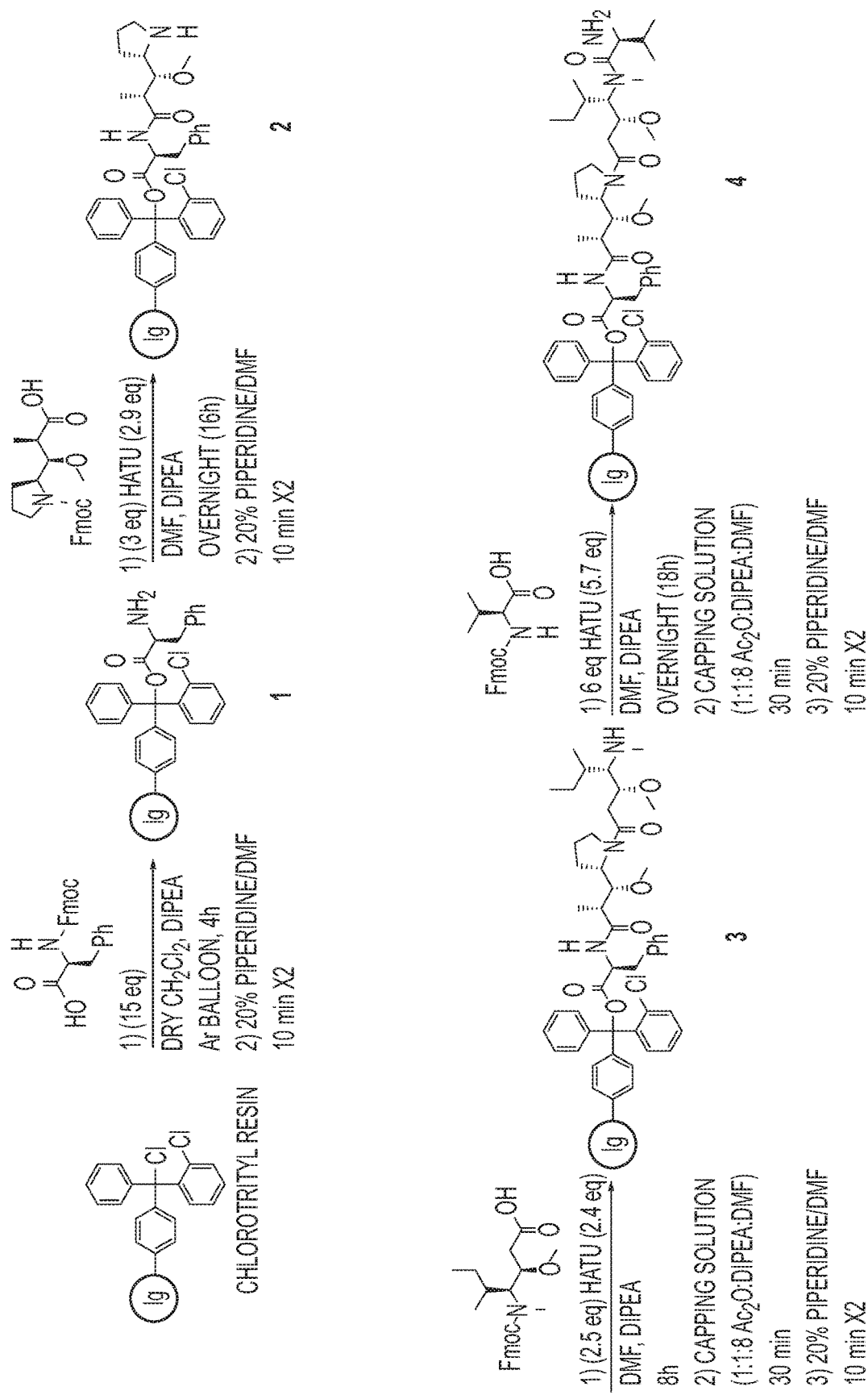
FIG. 16 depicts a non-limiting example of a solid phase synthesis reaction that can be used to produce a β-lactam-hydrocarbon linker-MMAF composition for use in conjugation to an immunoglobulin molecule.
Figure 16:
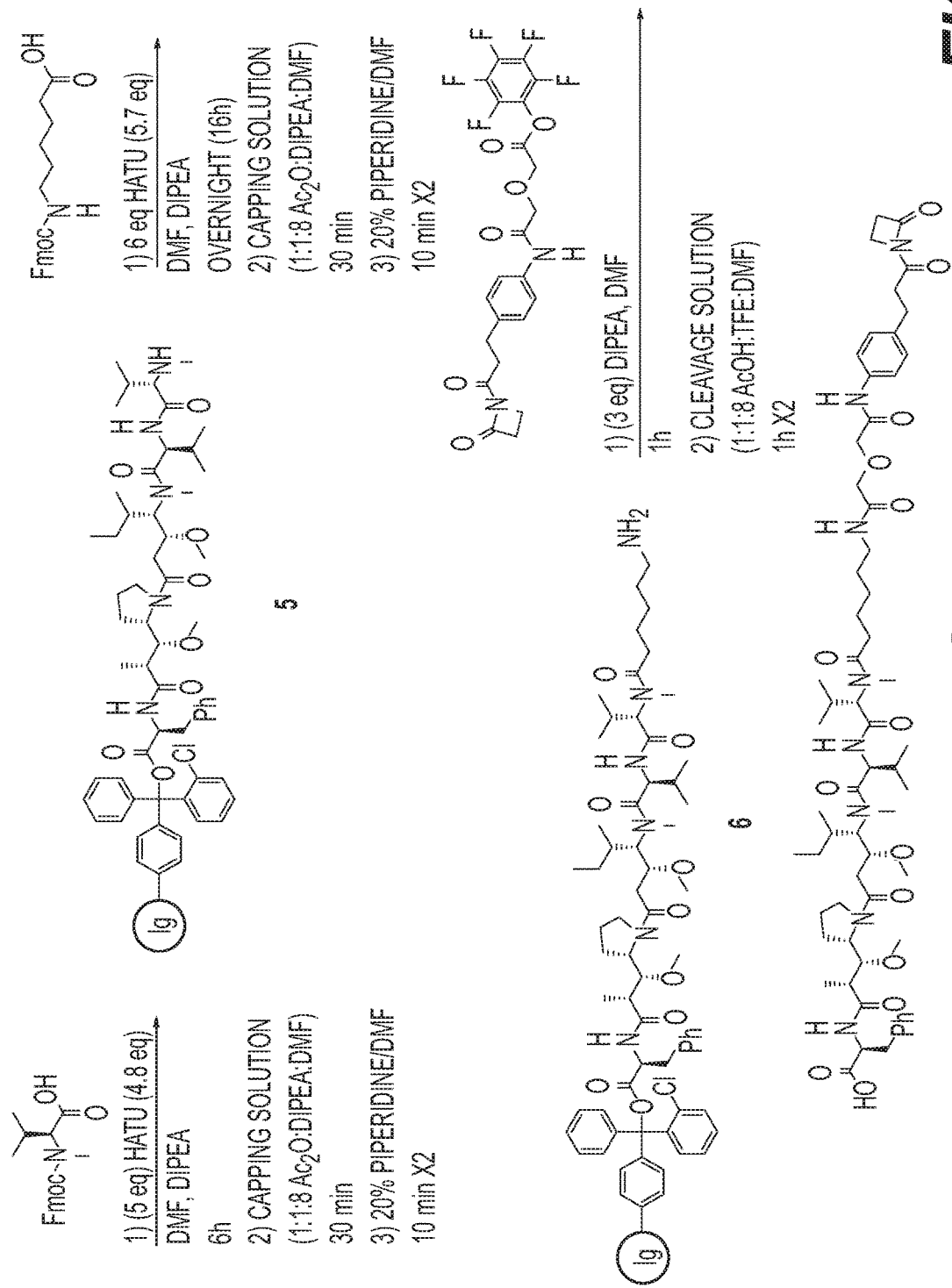

In certain aspects, a second variable domain of Ig includes a reactive lysine residue, and an immunoconjugate is created using a controlled conjugation reaction wherein a linker/drug moiety composition is conjugated to the reactive lysine residue on each heavy chain of a naked Ig. Conditions for this reaction are described, for example, in U.S. Pat. No. 8,252,902, which is herein incorporated by reference in its entirety. Briefly, the reaction can be carried out at room temperature in a solution of 1×PBS, 2% DMSO by reacting the Ig with a linker/drug moiety composition, thereby resulting in the attachment of one linker/drug moiety to each of the reactive lysine residues on the Ig. The result is an immunoconjugate having two drug moieties attached via linkers to the reactive lysine residues on each heavy chain of the Ig. A schematic representation of an example reaction is provided in FIG. 15.

In certain aspects, additional drug moieties can be conjugated to an Ig molecule using uncontrolled conjugation techniques. For example, in certain aspects, amino acid residues other than the single, uniquely reactive lysine residue of the 38C2 variable domain can be used as attachment points for conjugation of a drug moiety via a linker. The result of such uncontrolled conjugation is an immunoconjugate having one or more drug moieties attached to the other amino acid residues on the immunoglobulin molecule. Such additional conjugation can be accomplished by reacting a linker/drug moiety composition with, e.g., lysine residues on the immunoglobulin molecule other than the single, uniquely reactive lysine in the second variable domain, or standard or engineered cysteine residues on the immunoglobulin molecule, or one or more engineered selenocysteine residues on the immunoglobulin molecule. The result of such uncontrolled conjugation is an immunoconjugate with an average number of drug moieties that ranges from about 1 to about 20 drug moieties per antibody, depending on the number of amino acid residues that are available to react with the linker/drug moiety composition. In certain aspects, the average number of drug moieties per immunoglobulin molecule achieved using an uncontrolled conjugation approach is about 1 to about 8, such as 2, 3, 4, 5, 6, or 7 drug moieties per immunoglobulin.

In one aspect, an immunoconjugate includes a HER2-h38C2-DVD1 immunoglobulin molecule with an MMAF drug moiety conjugated to each of the reactive lysine residues via an irreversible linker. In one aspect, an immunoconjugate includes a HER2-h38C2-DVD2 immunoglobulin molecule with an MMAF drug moiety conjugated to each of the reactive lysine residues via an irreversible linker.

In one aspect, an immunoconjugate includes an IMGN-853 FOLR1-h38C2-DVD1 immunoglobulin molecule with an MMAF drug moiety conjugated to each of the reactive lysine residues via an irreversible linker. In one aspect, an immunoconjugate includes an IMGN-853 FOLR1-h38C2-DVD2 immunoglobulin molecule with an MMAF drug moiety conjugated to each of the reactive lysine residues via an irreversible linker.

In one aspect, an immunoconjugate includes a farletuzumab FOLR1-h38C2-DVD1 immunoglobulin molecule with an MMAF drug moiety conjugated to each of the reactive lysine residues via an irreversible linker. In one aspect, an immunoconjugate includes a farletuzumab FOLR1-h38C2-DVD2 immunoglobulin molecule with an MMAF drug moiety conjugated to each of the reactive lysine residues via an irreversible linker.

In one aspect, an immunoconjugate includes a CD138-h38C2-DVD1 immunoglobulin molecule with an MMAF drug moiety conjugated to each of the reactive lysine residues via an irreversible linker. In one aspect, an immunoconjugate includes a CD138-h38C2-DVD2 immunoglobulin molecule with an MMAF drug moiety conjugated to each of the reactive lysine residues via an irreversible linker.

Applications of Immunoconjugates

Immunoconjugates can have widespread preventative, therapeutic and diagnostic applications and methods of use, including but not limited to, the treatment of various cancers and other diseases by targeting and killing cells that express a particular tumor antigen. Immunoconjugates can broadly be used for the treatment of any of a variety of cancers. It is anticipated that any type of tumor and any type of tumor-associated antigen can be targeted by the subject immunoconjugates. Examples of cancer types include, without limitation, hematologic cancers, carcinomas, sarcomas, melanoma, and central nervous system cancers.

Non-limiting examples of hematologic cancers that can be treated with the subject immunoconjugates include leukemia, acute myeloid leukemia, acute lymphoblastic leukemia, chronic myelogenous leukemia, chronic lymphocytic leukemia, lymphoma, Hodgkin's lymphoma, non-Hodgkin's lymphoma, myeloma and myelodysplastic syndrome.

Non-limiting examples of carcinomas that can be treated with the subject immunoconjugates include skin cancer, head and neck, thyroid, lung, nasopharyngeal, colorectal, liver, urinary bladder, ovarian, cervical, endometrial, prostate, gastric, esophageal, pancreatic, renal, and breast cancer.

Non-limiting examples of sarcomas that can be treated with the subject immunoconjugates include angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, Kaposi's sarcoma and synovial sarcoma.

Non-limiting examples of central nervous system cancers that can be treated with the subject immunoconjugates include glioma, meningioma and neuroma.

Non-limiting examples of other cancers that can be treated with the subject immunoconjugates include melanoma.

In some instances, methods of use of the subject immunoconjugates involve administering an immunoconjugate to a subject, as described above, in conjunction with one or more additional therapies to treat a particular cancer. As such, a subject immunoconjugates can be used alone to treat a particular cancer, or alternatively, can be used in combination with or as an adjunct to conventional treatment with other medications, e.g., anti-neoplastic agents. Immunoconjugates can generally be used in combination with any anti-neoplastic agents, such as conventional and/or experimental chemotherapeutic agents, radiation treatments, and the like.

For example, in some aspects, an additional therapy can include an antibody, an anti-neoplastic agent, a cytotoxic agent, an anti-angiogenic agent, or an immunosuppressive agent. Non-limiting examples of additional therapeutic agents include cisplatin, carboplatin, oxaliplatin, mechlorethamine, cyclophosphamide, chlorambucil, ifosfamide, doxorubicin, daunorubicin, valrubicin, idarubicin, epirubicin, actinomycin, bleomycin, plicamycin, mitomycin, bevacizumab, imatinib, erlotinib, gefitinib, ibrutinib, idelalisib, lenalidomide, vincristine, vinblastine, vinorelbine, vindesine, paclitaxel, and docetaxel.

Pharmaceutical Compositions of Immunoconjugates

For therapeutic uses, immunoconjugates can be formulated into pharmaceutical compositions. A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it can be necessary to coat the compound with, or co-administer the compound with, a material to prevent its inactivation. For example, a compound can be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Compositions can also contain adjuvants such as preservatives, wetting agents, emulsifying agents and/or dispersing agents. Prevention of the presence of microorganisms can be ensured both by sterilization procedures and by the inclusion of various antibacterial and antifungal agents, for example, paraben, chlorobutanol, phenol, sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption, such as aluminum monostearate and gelatin.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. A selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition must be sterile and fluid to the extent that the composition is deliverable by syringe. In addition to water, the carrier preferably is an isotonic buffered saline solution.

Aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive residue; L is a linker that is covalently conjugated to the reactive residue of the second variable domain of Ig; D is a drug moiety; and n is an integer selected from 1 to 12, such as from 1 to 11, from 2 to 12, from 3 to 10, from 4 to 9, from 5 to 8, from 6 to 7, from 1 to 3, from 4 to 6, from 7 to 9, or from 10 to 12. In some aspects, n is 1, 2, 3, 4, 5, 6, 7, 8, 9, 10, 11, or 12. Further aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive lysine residue; L is a linker that is covalently conjugated to the reactive lysine residue of the second variable domain of Ig; D is a drug moiety; and n is 1 or 2. In some aspects, a first variable domain of Ig is positioned closer to an N-terminus than a second variable domain. In some aspects, Ig can be a bispecific immunoglobulin molecule. In some aspects, D comprises 2 or more different drug moieties. In some aspects, an antigen-binding fragment comprises a first and second variable domain of Ig, and is selected from a Fab, Fab', F(ab')$_2$, Fv or scFv. In some aspects, Ig comprises a chimeric immunoglobulin sequence. In some aspects, Ig comprises a humanized immunoglobulin sequence. In some aspects, Ig comprises a human immunoglobulin sequence. In some aspects, a second variable domain of Ig comprises the amino acid sequence of SEQ ID NO: 3. In some aspects, a second variable domain of Ig comprises the amino acid sequence of SEQ ID NO: 4.

In some aspects, a binding target is a tumor cell surface antigen. In some aspects, a tumor cell surface antigen is selected from HER2, FOLR1 and CD138. In some aspects, a first variable domain of Ig binds to HER2. In some aspects, a first variable domain of Ig binds to FOLR1. In some aspects, a first variable domain of Ig binds to CD138.

Aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive lysine residue; L is a linker that is covalently conjugated to the reactive lysine residue of the second variable domain of Ig; D is a drug moiety; and n is an integer selected from 1 to 12. Further aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive lysine residue; L is a linker that is covalently conjugated to the reactive lysine residue of the second variable domain of Ig; D is a drug moiety; and n is 1 or 2. In some aspects, D is a cytotoxic agent. In some aspects, a cytotoxic agent is selected from a toxin, a chemotherapeutic agent, an antibiotic, a radioactive isotope, a chelated radioactive isotope and a nucleolytic enzyme. In some aspects, D is an auristatin, a dolostatin or a cemadotin. In some aspects, D is an MMAE or an MMAF. In some aspects, D is a camptothecin. In some aspects, a camptothecin is SN-38. In some aspects, D is a maytansinoid. In some aspects, a maytansinoid is DM1, DM3 or DM4. In some aspects, D is a pyrrolobenzodiazepine (PBD). In some aspects, D is an enediyne. In some aspects, D is a calicheamicin. In some aspects, D is a tiancimycin. In some aspects, D is a doxorubicin. In some aspects, D is an MMDX. In some aspects, D is a PNU-159682.

Aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive residue; L is a linker that is covalently conjugated to the reactive residue of the second variable domain of Ig; D is a drug moiety; and n is selected from an integer from 1 to 12. Further aspects of the invention include an immunoconjugate having the formula Ig-(L-D)$_n$, wherein: Ig is a dual variable domain immunoglobulin molecule, or an antigen-binding fragment thereof, wherein the dual variable domain immunoglobulin molecule comprises a first variable domain that binds to a binding target, and a second variable domain that comprises a reactive lysine residue; L is a linker that is covalently conjugated to the reactive lysine residue of the second variable domain of Ig; D is a drug moiety; and n is 1 or 2. In some aspects, L is a reversible linker. In some aspects, L is an irreversible linker. In some aspects, L is a cleavable linker. In some aspects, L is a non-cleavable linker. In some aspects, L is a branched linker. In some aspects, L is a linear linker.

Aspects of the invention include pharmaceutical compositions for the treatment of cancer, wherein the pharmaceutical composition comprises an effective amount of an immunoconjugate and a pharmaceutically acceptable carrier.

Aspects of the invention include use of an immunoconjugate in the preparation of a medicament for treating cancer. In some aspects, a cancer is a hematological cancer, a carcinoma, a sarcoma, a melanoma, or a central nervous system cancer. In some aspects, a hematological cancer is a leukemia, lymphoma, myeloma, or myelodysplastic syndrome. In some aspects, a leukemia is an acute myeloid leukemia, acute lymphoblastic leukemia, chronic myelogenous leukemia, or chronic lymphocytic leukemia. In some aspects, a lymphoma is Hodgkin's lymphoma or non-Hodgkin's lymphoma. In some aspects, a carcinoma is a skin cancer, head and neck, thyroid, lung, nasopharyngeal, colorectal, liver, urinary bladder, ovarian, cervical, endometrial, prostate, gastric, esophageal, pancreatic, renal, or breast cancer. In some aspects, a sarcoma is an angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, Kaposi's sarcoma or synovial sarcoma. In some aspects, a central nervous system cancer is a glioma, meningioma or neuroma.

In some aspects, a medicament further comprises an effective amount of a second therapeutic agent. In some aspects, a second therapeutic agent is an antibody, an anti-neoplastic agent, a cytotoxic agent, an anti-angiogenic agent, or an immunosuppressive agent. In some aspects, a second therapeutic agent is selected from the group consisting of: cisplatin, carboplatin, oxaliplatin, mechlorethamine, cyclophosphamide, chlorambucil, ifosfamide, doxorubicin, daunorubicin, valrubicin, idarubicin, epirubicin, actinomycin, bleomycin, plicamycin, mitomycin, bevacizumab, imatinib, erlotinib, gefitinib, ibrutinib, idelalisib, lenalidomide, vincristine, vinblastine, vinorelbine, vindesine, paclitaxel, and docetaxel.

Aspects of the invention include an immunoconjugate having the formula Ig-(L-D)$_n$, wherein: Ig comprises the amino acid sequences of SEQ ID NOs: 5 and 6 and the binding target of the first variable domain is HER2; L is a linear, irreversible linker that is covalently conjugated to a reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 7 and 8 and the binding target of the first variable domain is HER2; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 9 and 10 and the binding target of the first variable domain is FOLR1; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 11 and 12 and the binding target of the first variable domain is FOLR1; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 13 and 14 and the binding target of the first variable domain is FOLR1; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 15 and 16 and the binding target of the first variable domain is FOLR1; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 17 and 18 and the binding target of the first variable domain is CD138; L is a linear, irreversible linker that is covalently conjugated to the reactive lysine residue of Ig; D is MMAF; and n is 2.

Aspects of the invention include an immunoconjugate having the formula Ig-(L-D)$_n$, wherein: Ig comprises the amino acid sequences of SEQ ID NOs: 19 and 20 and the binding target of the first variable domain is CD138; L is a linear, irreversible linker that is covalently conjugated to the reactive lysine residue of Ig; D is MMAF; and n is 2.

In some aspects, an immunoglobulin is composed of two identical light chains and two identical heavy chains. In one aspect, an immunoglobulin light chain comprises a kappa light chain. In one aspect, an immunoglobulin light chain comprises a lambda light chain. In one aspect, an immunoglobulin is an IgA immunoglobulin, having an α heavy chain. In one aspect, an immunoglobulin is an IgA1 immunoglobulin. In one aspect, an immunoglobulin is an IgA2 immunoglobulin. In one aspect, an immunoglobulin is an IgD immunoglobulin, having a δ heavy chain. In one aspect, an immunoglobulin is an IgE immunoglobulin, having an ε heavy chain. In one aspect, an immunoglobulin is an IgG immunoglobulin, having a γ heavy chain. In one aspect, an immunoglobulin is an IgG1 immunoglobulin. In one aspect, an immunoglobulin is an IgG2 immunoglobulin. In one aspect, an immunoglobulin is an IgG3 immunoglobulin. In one aspect, an immunoglobulin is an IgG4 immunoglobulin. In one aspect, an immunoglobulin is an IgM immunoglobulin, having a μ heavy chain.

In one aspect, an immunoglobulin comprises at least one variable region. In one aspect, an immunoglobulin is an intact immunoglobulin. In one aspect, an immunoglobulin is a naked immunoglobulin. In one aspect, an immunoglobulin is an immunoglobulin fragment. In one aspect, an immunoglobulin fragment is selected from the group consisting of: Fab, Fab', F(ab')$_2$, Fv and scFv.

In some aspects, an immunoglobulin is a dual variable domain immunoglobulin. In some aspects, an immunoglobulin comprises a native polypeptide sequence. In some aspects, an immunoglobulin comprises a non-native polypeptide sequence. In some aspects, an immunoglobulin comprises a polypeptide. In some aspects, an immunoglobulin is a monoclonal immunoglobulin. In some aspects, an immunoglobulin comprises a chimeric immunoglobulin. In some aspects, an immunoglobulin comprises a humanized immunoglobulin. In some aspects, an immunoglobulin comprises a human immunoglobulin. In some aspects, an immunoglobulin is an isolated immunoglobulin. In some aspects, an immunoglobulin comprises a polypeptide sequence that is a fusion of two or more polypeptide sequences. In some aspects, an immunoglobulin is a conjugated immunoglobulin.

In some aspects, and immunoglobulin specifically binds to or is specific for a binding target. In some aspects, an immunoglobulin has a binding affinity. In some aspects, an immunoglobulin has a K$_d$ value. In some aspects, an immunoglobulin binds to an epitope. In some aspects, an immunoglobulin binds to a target or binding target. In some aspects, a binding target comprises a binding region, to which an immunoglobulin binds. In some aspects, an immunoglobulin binds to an antigen. In some aspects, an immunoglobulin comprises an antigen binding site or antigen binding region.

In some aspects, an immunoglobulin is produced in a host cell. In some aspects, an immunoglobulin is produced by a cell line or a cell culture. In some aspects, an immunoglobulin is produced from a nucleic acid sequence that is operably linked to another nucleic acid sequence.

In some aspects, an immunoglobulin amino acid sequence has a percent amino acid sequence identity to another amino acid sequence.

In some aspects, an immunoconjugate is used for treatment of a subject or mammal.

The following examples, sequences and figures are provided to aid the understanding of the present invention, the true scope of which is set forth in the appended claims. It is understood that modifications can be made in the procedures set forth without departing from the spirit of the invention.

EXAMPLES

Example 1: Chemical Synthesis of β-Lactam-Cit-Val-MMAF

Figure 11:
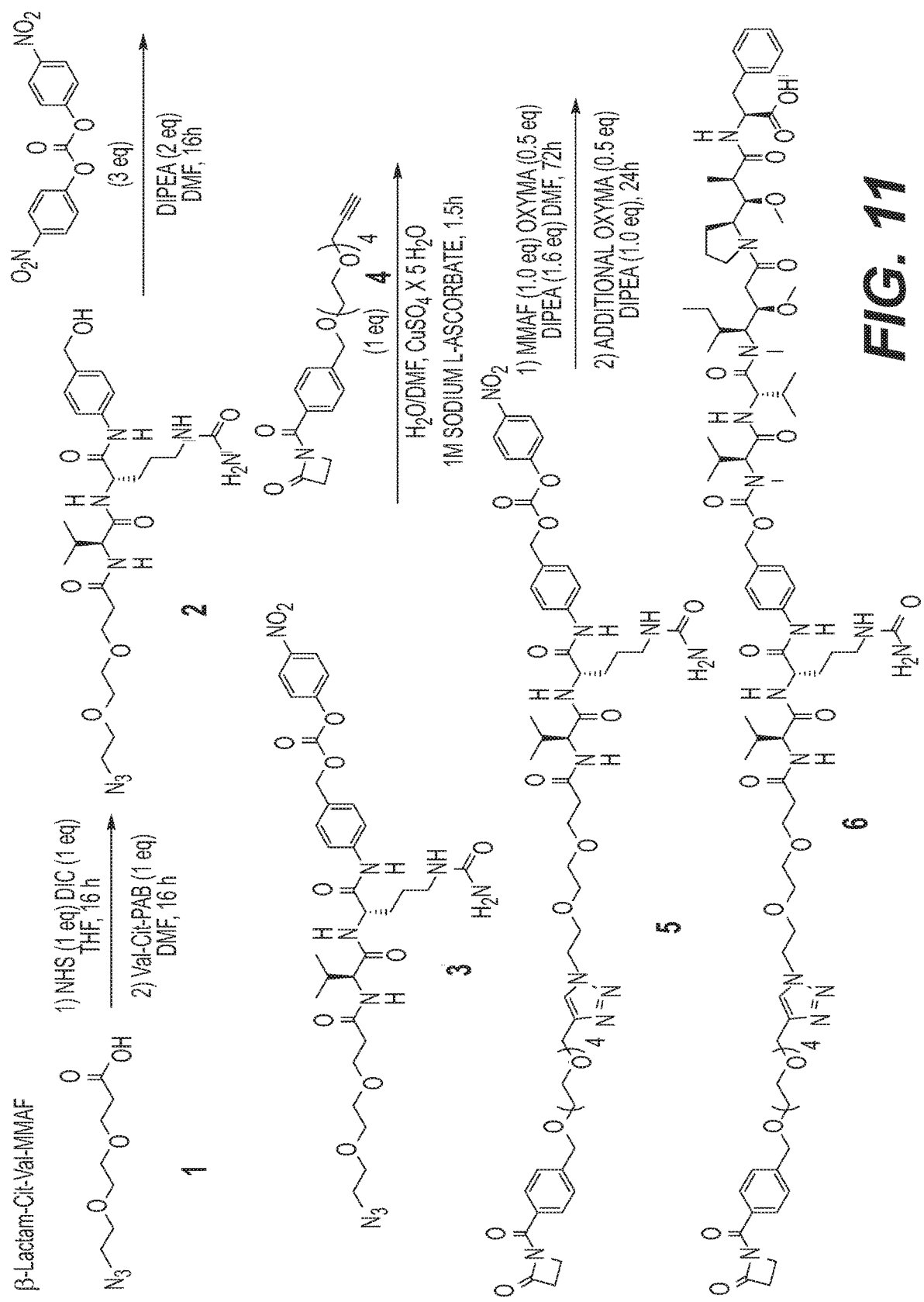
FIG. 11 depicts a reaction process for chemical synthesis of a β-Lactam-Cit-Val-MMAF.

References are made to chemical compounds labeled 1-6 in FIG. 11. To 332 mg of Compound 1 (Gervay-Hague, J. et al. *JACS*. 2011, 133 (10), 3230-3233) is added 107 mg of NHS (1 eq) and 3 ml of dry THF. The reaction is cooled to 0° C., then 0.143 ml (1 eq) of DIC is added. The reaction is warmed to room temperature over 24 h, filtered through celite, and solvent is removed in vacuo. 350 mg (1 eq) of Val-Cit-PAB (Trail, P. A. et al. *Bioconjugate Chem.* 2002, 13, 855-869) is added then 5.6 ml of dry DMF and the reaction is stirred for 16h. Product formation is confirmed after 16 hours by LC/MS. The solvent is removed in vacuo and the crude material is triturated with CH$_2$Cl$_2$ then filtered and rinsed with hexanes. The crude brown solid is purified by column chromatography (9:1 CH$_2$Cl$_2$:MeOH, Rf=0.2) (61% Yield).

312 mg of compound 2, 505 mg of bis-nitrocarbonate (3 eq), 0.193 ml DIPEA (2 eq), and 7 ml of dry DMF is combined and stirred for 16h. The solvent is removed in vacuo and the crude material is purified by reverse-phase HPLC. (35% Yield).

38 mg of compound 3, 22 mg of compound 4 (Barbas, C. F. et al. *ACS Med. Chem. Lett.*, 2014, 5 (2), 133-137), 6 mg of CuSO$_4$ 5H$_2$O, 0.5 ml DMF, and 0.25 ml of H$_2$O is combined and degassed for 30 min. 12 µL 1M sodium ascorbate is then added and the reaction is stirred for 1.5 h then purified by reverse-phase HPLC. (60% Yield).

2.0 mg MMAF, 4.8 mg compound 5 (1.5 eq), 0.2 mg Oxyma (0.5 eq), 0.77 µl DIPEA (1.6 eq), and 70 µl dry DMF is combined in a flame dried microwave vial. After 72h, additional 0.2 mg Oxyma (0.5 eq) and 0.48 µl DIPEA (1 eq) is added. 24 h later the reaction is purified by reverse-phase HPLC to obtain 1.9 mg of compound 6 (40% Yield).

Example 2: Chemical Synthesis of β-Lactam-PEG Linker-MMAF

Figure 12:
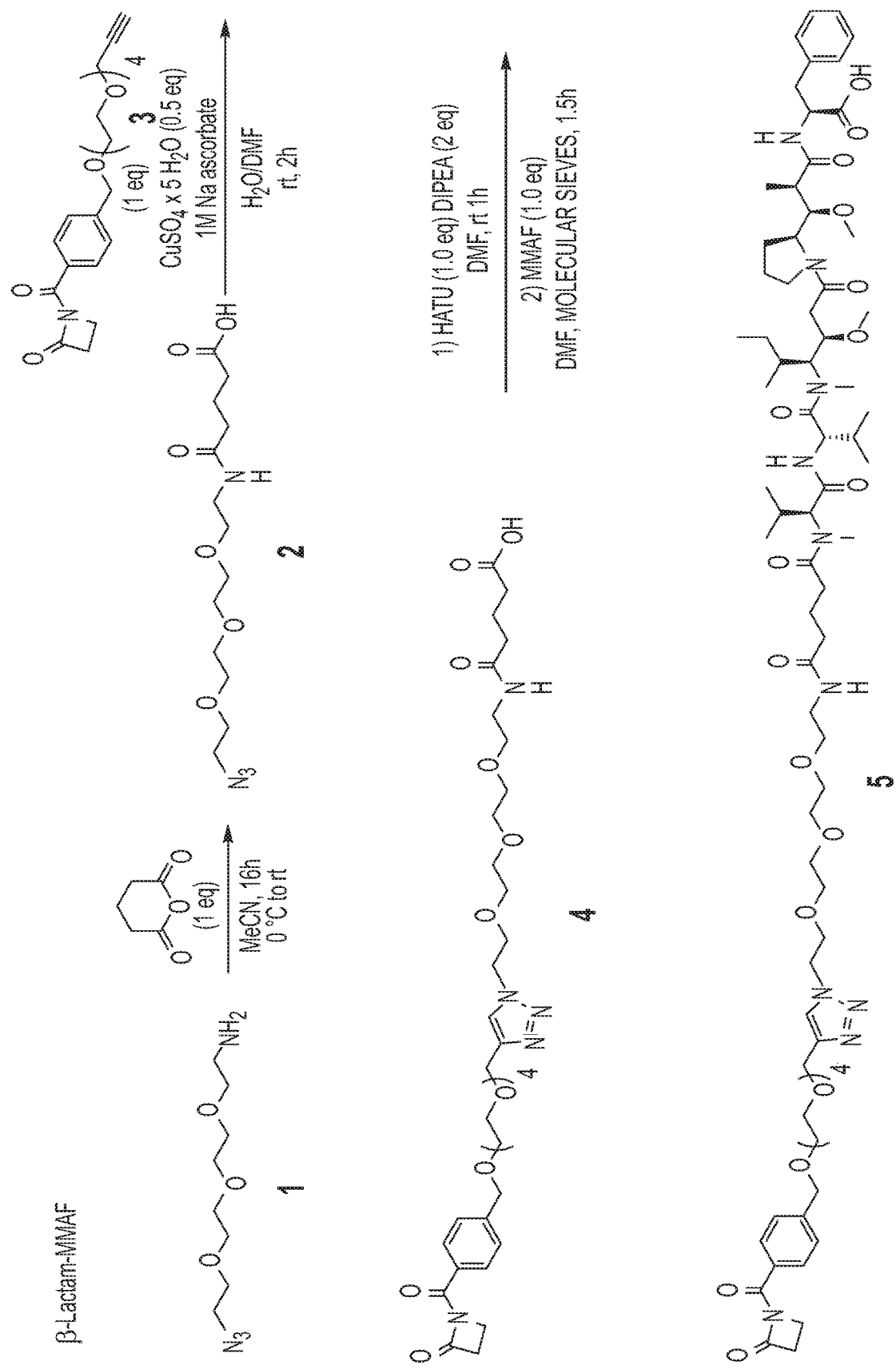
FIG. 12 depicts a reaction process for chemical synthesis of a β-Lactam-PEG linker-MMAF.

References are made to chemical compounds labeled 1-5 in FIG. 12. 332 mg of compound 1 (Okoth, R. et al. *J. Org. Chem.*, 2013, 9, 608-612) is dissolved in 1.6 ml MeCN. 173 mg of glutaric anhydride (1 eq) is dissolved in 1 ml MeCN and added to compound 1 over 30 min. 18 h later, the solvent is removed in vacuo. The crude product is dissolved in CH$_2$Cl$_2$ and purified by column chromatography (95:5, CH$_2$Cl$_2$:MeOH) (88% Yield).

18 mg of compound 2, 22 mg of compound 3 (Barbas, C. F. et al. *ACS Med. Chem. Lett.*, 2014, 5 (2), 133-137), 6 mg of CuSO$_4$ 5H$_2$O (0.5 eq), 0.25 ml DMF, and 0.25 ml of H$_2$O is combined and degassed for 30 min. 12 µL 1M sodium ascorbate is then added and the reaction is stirred for 1.5 h then purified by reverse-phase HPLC. (43% Yield).

3 mg of compound 4, 7 mg of 4 Å molecular sieves, 1.5 mg of HATU (1 eq), 1.5 µl DIPEA (2 eq), and 33 µl dry DMF is combined in flame dried vial. After 1 hour, 1.4 mg MMAF is added with 40 µl dry DMF. After 1.5h, purified using reverse-phase HPLC to obtain compound 5 (82% Yield).

Example 3: Solid Phase Chemical Synthesis of β-Lactam-Hydrocarbon Linker-MMAF

Figure 44:
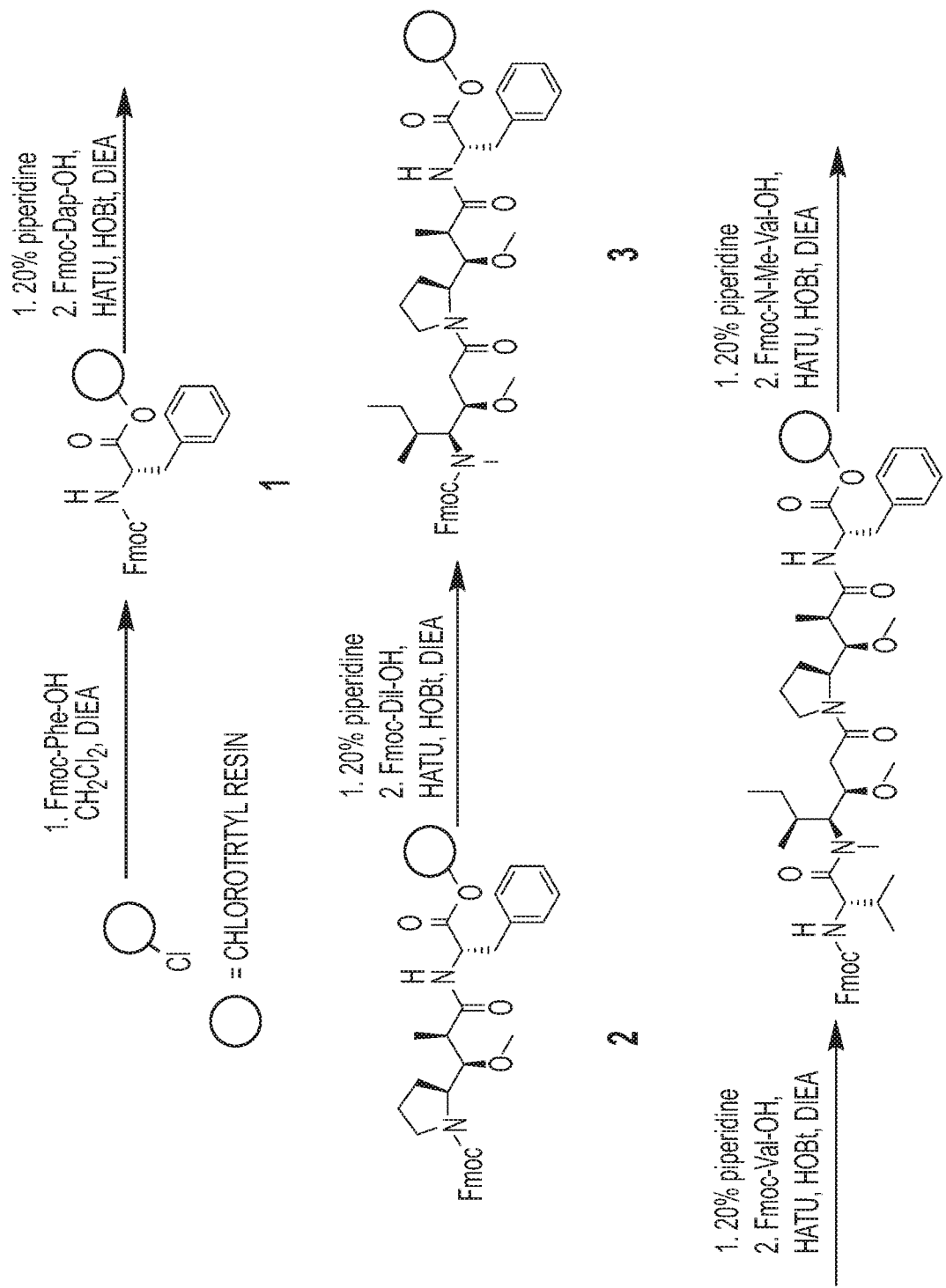
FIG. 44 provides a solid-phase synthesis scheme of β-lactam MMAF.
Figure 44:
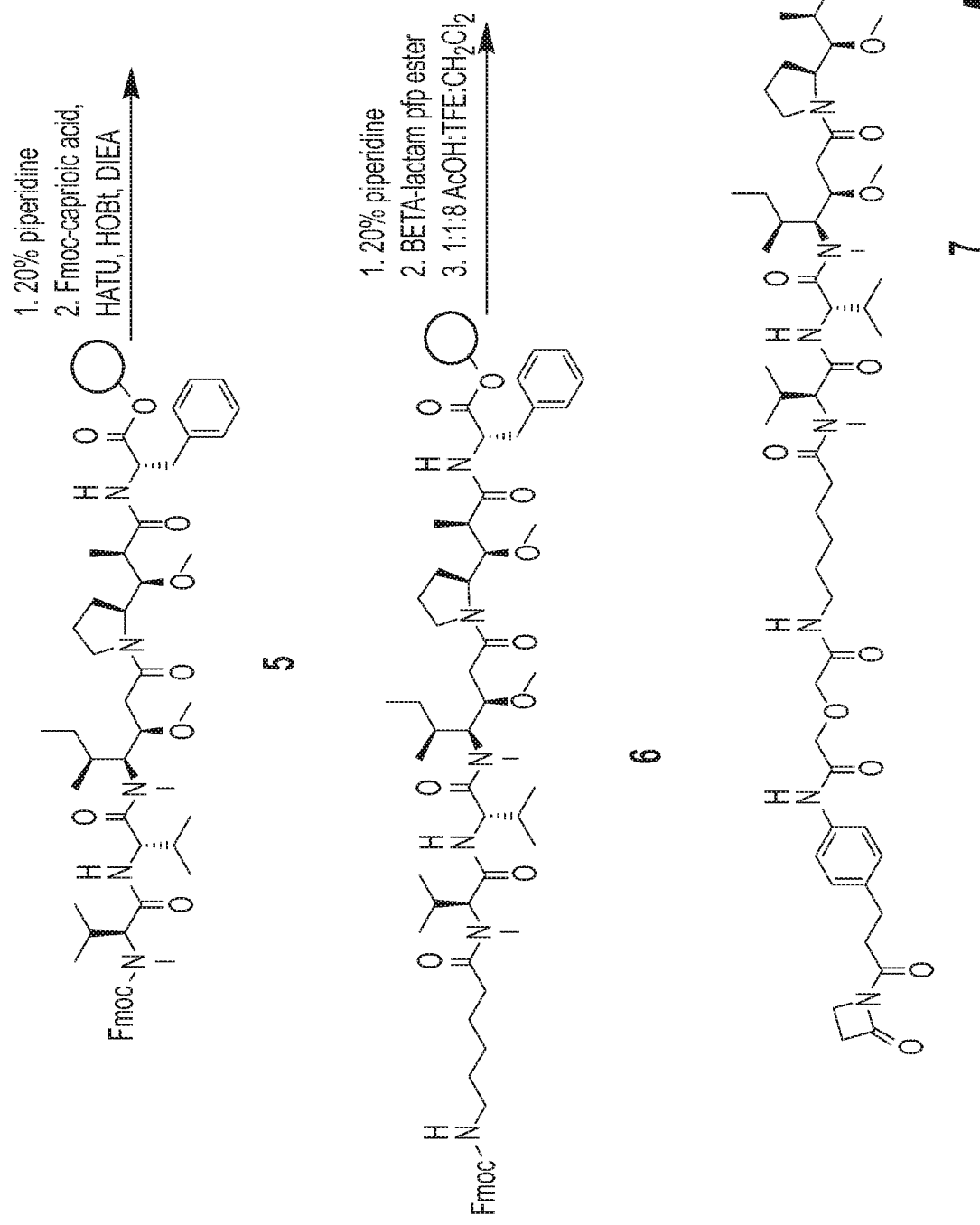

References are made to chemical compounds labeled 1-7 in FIG. 44. Fmoc-Phe-OH (15 eq) dissolved in 4 ml of dry $CH_2Cl_2$ and 0.5 ml of DIPEA is added to pre-swollen chlorotrityl resin. The mixture is agitated for 4 h then solvent is removed and agitated with MeOH for 20 min to obtain resin 1. The mixture is then deprotected with 20% piperidine in DMF (2 mL×20 min×2 times), washed with DMF, and is agitated with a freshly prepared solution of Fmoc-Dap-OH (3 equiv), HATU (3 equiv), and DIPEA (10 equiv) in DMF (1.5 mL) at room temperature (overnight), then drained and washed with DMF to obtain resin 2. The mixture is then Fmoc-deprotected with 20% piperidine in DMF (2 mL×20 min×2 times), is agitated with a freshly prepared solution of Fmoc-Dil-OH (2.5 equiv), HATU (2.5 equiv), and DIPEA (5 equiv) in DMF (2.5 mL) at room temperature (overnight), and washed with DMF to obtain resin 3. Unfunctionalized resin is capped with a solution of acetic anhydride (10:10:80 v/v $Ac_2O$:DIEA:DMF) at room temperature (30 min). Resin 3 is Fmoc-deprotected with 20% piperidine in DMF (2 mL×20 min×2 times), is agitated with a freshly prepared solution of Fmoc-Val-OH (6.0 equiv), HATU (6.0 equiv), and DIEA (12 equiv) in DMF (4.2 mL) at room temperature (overnight), and then is washed with DMF. Unfunctionalized resin is then capped with a solution of acetic anhydride (10:10:80 v/v $Ac_2O$:DIPEA:DMF) at room temperature (30 min) and washed with DMF to obtain resin 4. Resin 4 is Fmoc-deprotected with 20% piperidine in DMF (2 mL×20 min×2 times), is agitated with a freshly prepared solution of Fmoc-N-methyl-Val-OH (5 equiv), HATU (5 eq), DIPEA (10 equiv) in DMF (4.2 mL) at room temperature (3 h), then is washed with DMF. Unfunctionalized resin is then capped with a solution of acetic anhydride (10:10:80 v/v $Ac_2O$: DIPEA:DMF) at room temperature (30 min) and washed with DMF to obtain resin 5. Resin 5 is Fmoc-deprotected with 20% piperidine in DMF (2 mL×20 min×2 times), is agitated with a freshly prepared solution of Fmoc-caproic acid (6 equiv), HATU (6 equiv), and DIEA (12 eq) in DMF (2.5 mL) at room temperature (overnight), and then is washed with DMF. Unfunctionalized resin is then capped with a solution of acetic anhydride (10:10:80 v/v $Ac_2O$: DIPEA:DMF) at room temperature (30 min), and is washed with DMF to obtain resin 6. Resin 6 is Fmoc-deprotected with 20% piperidine in DMF (2 mL×20 min×2 times), is washed with DMF, and is then agitated with a freshly prepared solution of β-Lactam pfp ester (Magano, *J. Org. Process Res. Dev.*, 2014, 18 (1), 142-151) (3 equiv), and DIPEA (3 eq) in DMF (1.5 ml) at room temperature (1 h). The resin is then washed, sequentially, with DMF and DCM. The resin is then treated with dilute AcOH solution (1:1:8 v/v AcOH:TFE:DCM; 2.5 mL×30 min×2 times) to cleave peptide product, concentrated in vacuo, and purified using reverse-phase HPLC, giving compound 7.

Example 4: HER2-h38C2-DVD1 and DVD2 Cloning, Expression and Purification

DNA fusing the variable domain sequence of anti-HER2 to the variable domain sequence of h38C2 is custom synthesized as gBlocks Gene Fragments (Integrated DNA Technologies) or is prepared by PCR. Two versions with different peptide linker sequences (ASTKGP (SEQ ID NO: 1) for DVD1 or TVAAPSVFIFPP (SEQ ID NO: 2) for DVD2) separate the variable domain sequences. All antibodies use constant domains from human IgG1. DNA is amplified by PCR and cloned into pCEP4 (Invitrogen) with NheI/XhoI ligation. DNA is verified by DNA sequencing and all plasmids are purified with the QIAGEN Plasmid Maxi Kit for transfections.

Human embryonic kidney (HEK) 293 cells (ATCC) are maintained in DMEM (Dulbecco's Modified Eagle's Medium with GlutaMAX; Life Technologies) containing 10% (v/v) Fetal Bovine Serum (FBS; Life Technologies) and 1% (v/v) Penicillin Streptomycin (Pen Strep; Life Technologies) in a humidified 5% $CO_2$ atmosphere at 37° C. The mammalian cell expression vectors described above are transiently transfected into HEK 293 cells using polyethylenimine (PEI; Polysciences). After 12-16 h of transfections, media is replaced with fresh DMEM without FBS. Culture supernatants are collected on days 3, 6, and 9 after transfections and filtered using 0.45-µm Stericup filter units (Millipore). The supernatants are loaded on a 1 mL recombinant Protein A column (HiTrap; GE Healthcare) connected to an ÄKTApurifier system (GE Healthcare). PBS is used for column equilibration and washing, 0.5 M acetic acid (pH 3.0) for elution, and 1 M Tris-HCl (pH 8.0) for immediate neutralization. The neutralized eluate is buffer exchanged into PBS and concentrated simultaneously using 30-kDa cutoff centrifugal filter devices (Millipore). All immunoglobulins are determined to be >95% pure by SDS-PAGE.

Example 5: FOLR1-h38C2-DVD1 and DVD2 Cloning, Expression and Purification

DNA fusing the variable domain sequence of anti-FOLR1 to the variable domain sequence of h38C2 is custom synthesized as gBlocks Gene Fragments (Integrated DNA Technologies) or is prepared by PCR. Two versions with different peptide linker sequences (ASTKGP (SEQ ID NO: 1) for DVD1 or TVAAPSVFIFPP (SEQ ID NO: 2) for DVD2) separate the variable domain sequences. All antibodies use constant domains from human IgG1. DNA is amplified by PCR and cloned into pCEP4 (Invitrogen) with NheI/XhoI ligation. DNA is verified by DNA sequencing and all plasmids are purified with the QIAGEN Plasmid Maxi Kit for transfections.

Human embryonic kidney (HEK) 293 cells (ATCC) are maintained in DMEM (Dulbecco's Modified Eagle's Medium with GlutaMAX; Life Technologies) containing 10% (v/v) Fetal Bovine Serum (FBS; Life Technologies) and 1% (v/v) Penicillin Streptomycin (Pen Strep; Life Technologies) in a humidified 5% $CO_2$ atmosphere at 37° C. The mammalian cell expression vectors described above are transiently transfected into HEK 293 cells using polyethylenimine (PEI; Polysciences). After 12-16 h of transfections, media is replaced with fresh DMEM without FBS. Culture supernatants are collected on days 3, 6, and 9 after transfections and filtered using 0.45-µm Stericup filter units (Millipore). The supernatants are loaded on a 1 mL recombinant Protein A column (HiTrap; GE Healthcare) connected to an ÄKTApurifier system (GE Healthcare). PBS is used for column equilibration and washing, 0.5 M acetic acid (pH 3.0) for elution, and 1 M Tris-HCl (pH 8.0) for immediate neutralization. The neutralized eluate is buffer exchanged into PBS and concentrated simultaneously using 30-kDa cutoff centrifugal filter devices (Millipore). All immunoglobulins are determined to be >95% pure by SDS-PAGE.

Example 6: CD138-h38C2-DVD1 and DVD2 Cloning, Expression and Purification

DNA fusing the variable domain sequence of anti-CD138 to the variable domain sequence of h38C2 is custom synthesized as gBlocks Gene Fragments (Integrated DNA Technologies) or is prepared by PCR. Two versions with different peptide linker sequences (ASTKGP (SEQ ID NO: 1) for DVD1 or TVAAPSVFIFPP (SEQ ID NO: 2) for DVD2) separate the variable domain sequences. All antibodies use constant domains from human IgG1. DNA is amplified by PCR and cloned into pCEP4 (Invitrogen) with NheI/XhoI ligation. DNA is verified by DNA sequencing and all plasmids are purified with the QIAGEN Plasmid Maxi Kit for transfections.

Human embryonic kidney (HEK) 293 cells (ATCC) are maintained in DMEM (Dulbecco's Modified Eagle's Medium with GlutaMAX; Life Technologies) containing 10% (v/v) Fetal Bovine Serum (FBS; Life Technologies) and 1% (v/v) Penicillin Streptomycin (Pen Strep; Life Technologies) in a humidified 5% $CO_2$ atmosphere at 37° C. The mammalian cell expression vectors described above are transiently transfected into HEK 293 cells using polyethylenimine (PEI; Polysciences). After 12-16 h of transfections, media is replaced with fresh DMEM without FBS. Culture supernatants are collected on days 3, 6, and 9 after transfections and filtered using 0.45-µm Stericup filter units (Millipore). The supernatants are loaded on a 1 mL recombinant Protein A column (HiTrap; GE Healthcare) connected to an ÄKTApurifier system (GE Healthcare). PBS is used for column equilibration and washing, 0.5 M acetic acid (pH 3.0) for elution, and 1 M Tris-HCl (pH 8.0) for immediate neutralization. The neutralized eluate is buffer exchanged into PBS and concentrated simultaneously using 30-kDa cutoff centrifugal filter devices (Millipore). All immunoglobulins are determined to be >95% pure by SDS-PAGE.

Example 7: Conjugation of β-Lactam-MMAF to DVD Immunoglobulin

To 300 µg of dual variable domain immunoglobulin comprising h38C2 variable domains (each having a single, uniquely reactive lysine) in 270 µl PBS add 1.2 µl DMSO, add 1.5 µl (10 mM stock in DMSO, 10 eq) of β-lactam-MMAF and vortex, then incubate at room temperature for 2h. Load the antibody-drug conjugate solution on a G-25 prepacked sephadex column (GE Healthcare) that is equilibrated with PBS. Elute the antibody-drug conjugate using PBS.

Figure 17:
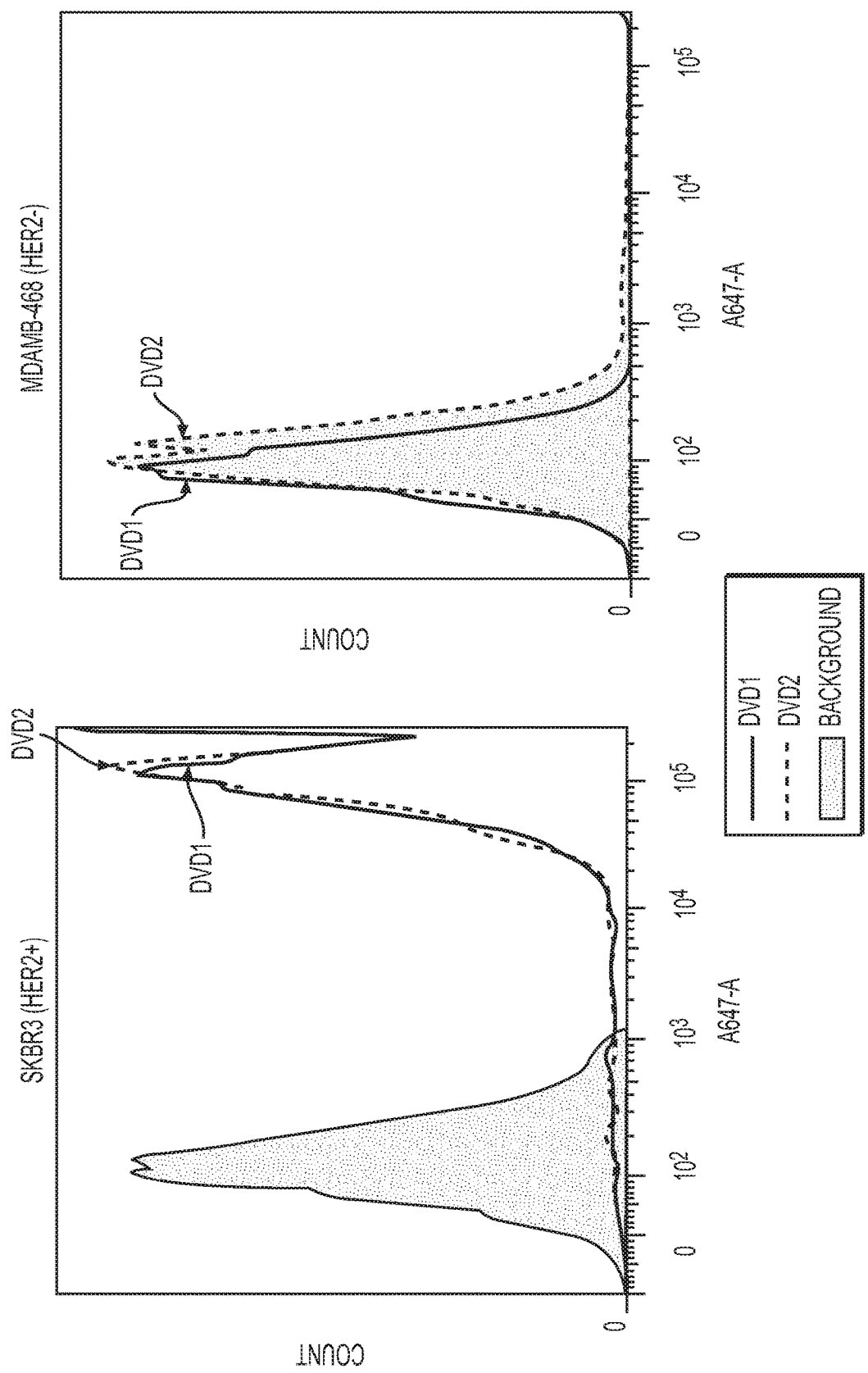
FIG. 17 provides binding data that demonstrates specific binding of an anti-HER2 dual variable domain immunoconjugate to HER2$^+$ cells.
Figure 17:
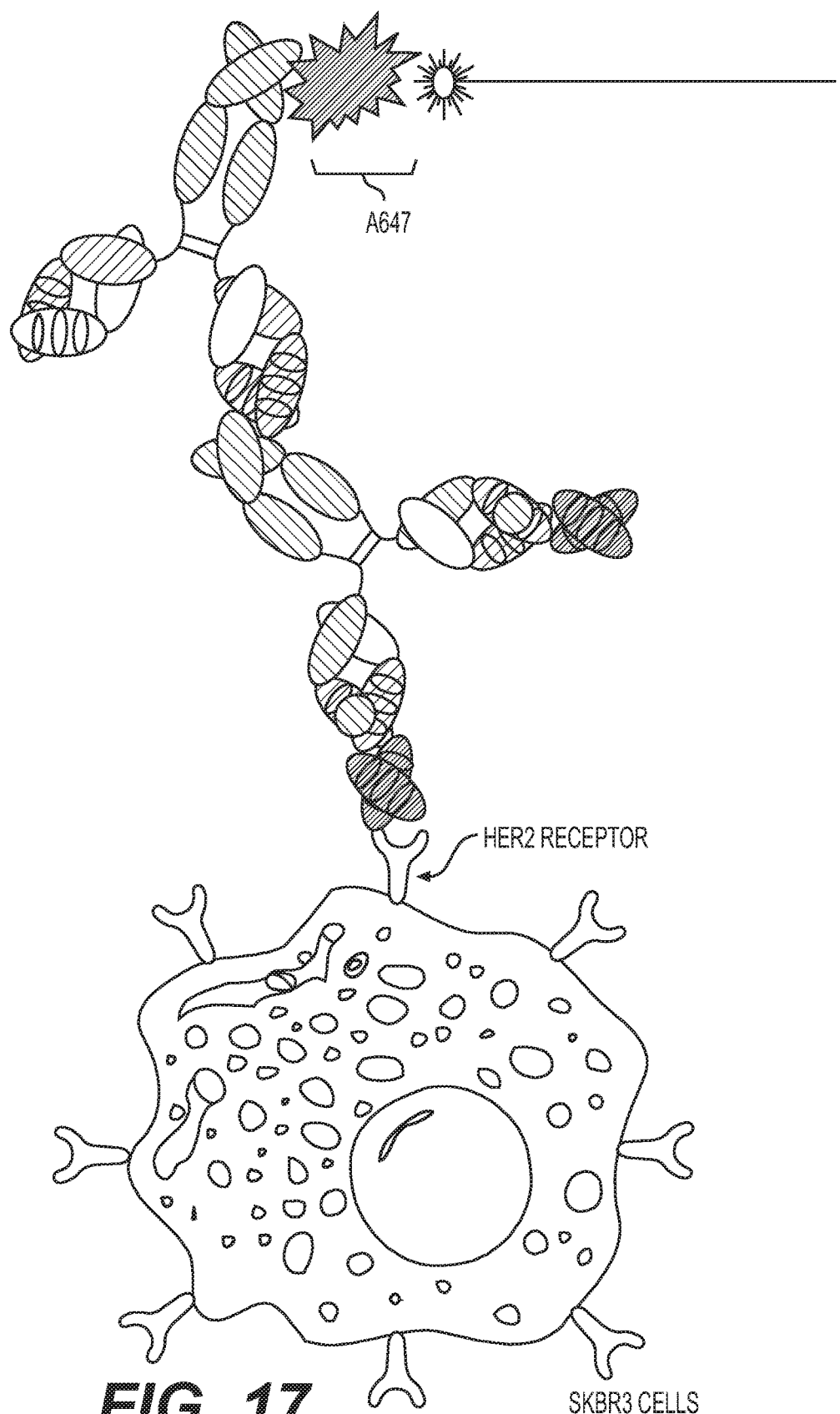

Example 8: Binding Analysis of Anti-HER2 Immunoconjugate to HER⁺ and HER⁻ Cells As depicted in FIG. 17, human breast cancer cell lines SK-BR-3 and MDA-MB-468 are purchased from ATCC. Both cell lines are maintained at 37° C. in a humidified 5% CO2 atmosphere in DMEM completed with 10% FBS and 1% Pen Strep. Cells are harvested using TrypLE (Life Technologies) and transferred to a V-shaped 96-well microtiter plate and washed with 200 µl FACS buffer (1% FBS in PBS). 1 µg of DVD in 100 µl of PBS is added to each well and incubated for 30 min on ice. The cells are washed with 200 µl FACS buffer then stained with 647-conjugated goat anti-human Fcg (Jackson ImmunoResearch) (10 µl, diluted 1:100 in FACs Buffer) on ice for 20 min. The cells are washed with 200 µl FACS buffer (×2), resuspended in 200 µl FACS buffer, and fluorescence is measured by flow cytometry (BD Facs Canto II). Data is analyzed using FlowJo software (Tree Star, Inc.).

Example 9: Cytotoxicity Assays with Anti-HER2 Immunoconjugates

Human breast cancer cell lines SK-BR-3 and MDA-MB-468 are maintained at 37° C. in a humidified 5% $CO_2$ atmosphere in DMEM completed with 10% FBS and 1% Pen Strep. Cells are harvested using TrypLE (Life Technologies) and transferred to a Flat-Bottom 96-well tissue culture plate (5000 cells/well) 24 hours before treatment. Serial dilutions are prepared in DMEM completed with 10% FBS and 1% Pen Strep. Original cell media is removed and 100 µl of treatment solution is added (performed in triplicate) and the culture plate is maintained at 37° C. in a humidified 5% $CO_2$ atmosphere for 72h. 20 µl CellTiter 96® Aqueous One Solution (Promega) is added to each well and the plate is developed at 37° C. in a humidified 5% $CO_2$ atmosphere. The cells are then contacted with an immunoconjugate, or with one of several control compositions.

Figure 18:
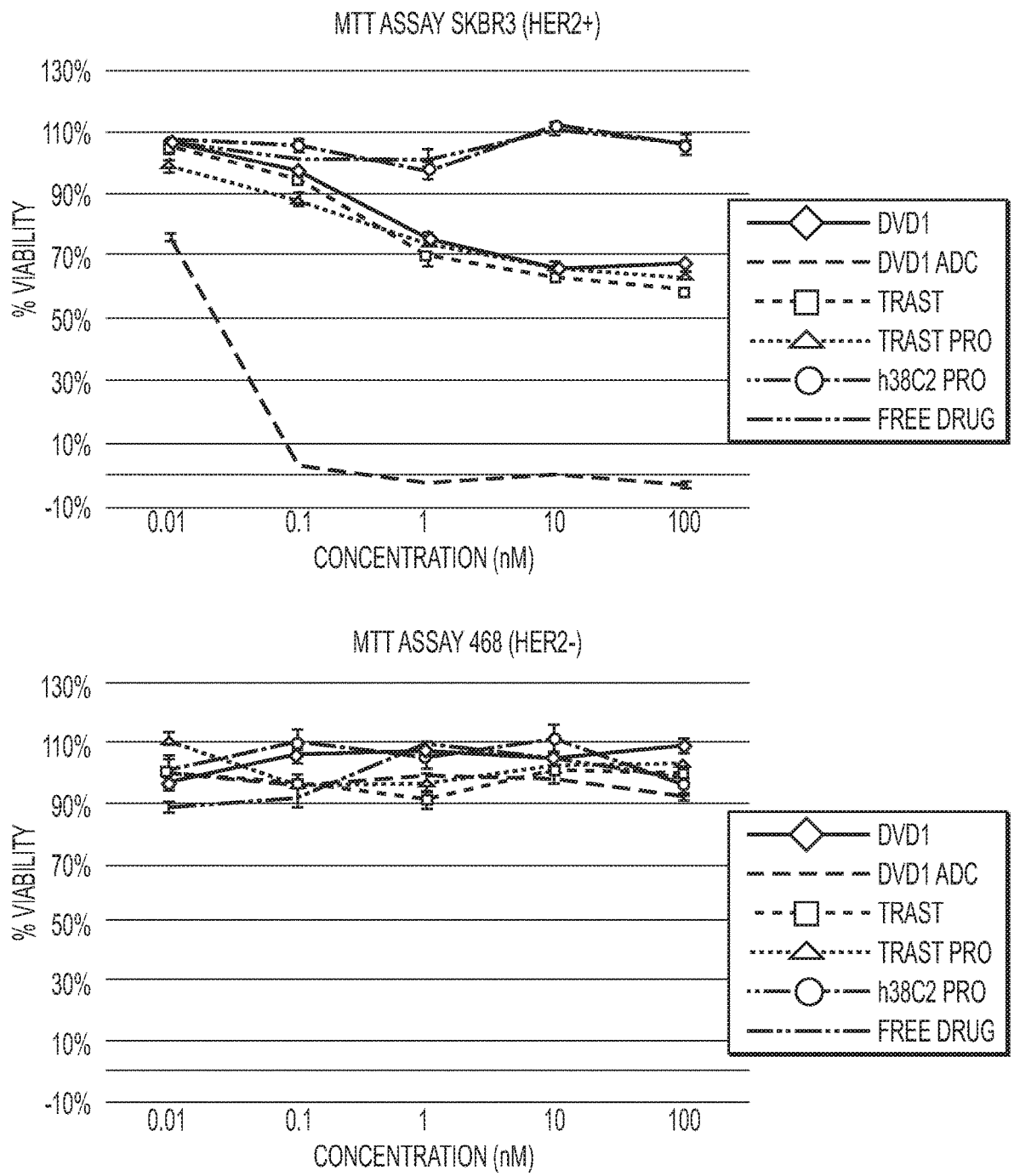
FIG. 18 depicts two graphs providing data from a first cytotoxicity assay demonstrating cell killing by an anti-HER2 dual variable domain immunoconjugate.

With reference to the graphs depicted in FIG. 18, DVD1 refers to the naked HER2-h38C2-DVD1 immunoglobulin (i.e., with no linker/drug moiety composition conjugated thereto); DVD1 ADC refers to the DVD1 immunoglobulin with a β-lactam-hydrocarbon linker-MMAF attached thereto; trast refers to a naked anti-HER2 antibody (trastuzumab); trast pro refers to the naked anti-HER2 antibody that has been mixed with a β-lactam-hydrocarbon linker-MMAF composition; h38C2 pro refers to an h38C2 antibody that has been conjugated to a β-lactam-hydrocarbon linker-MMAF composition but does not include a HER2 variable region binding domain; and free drug refers to the β-lactam-hydrocarbon linker-MMAF composition.

Figure 19:
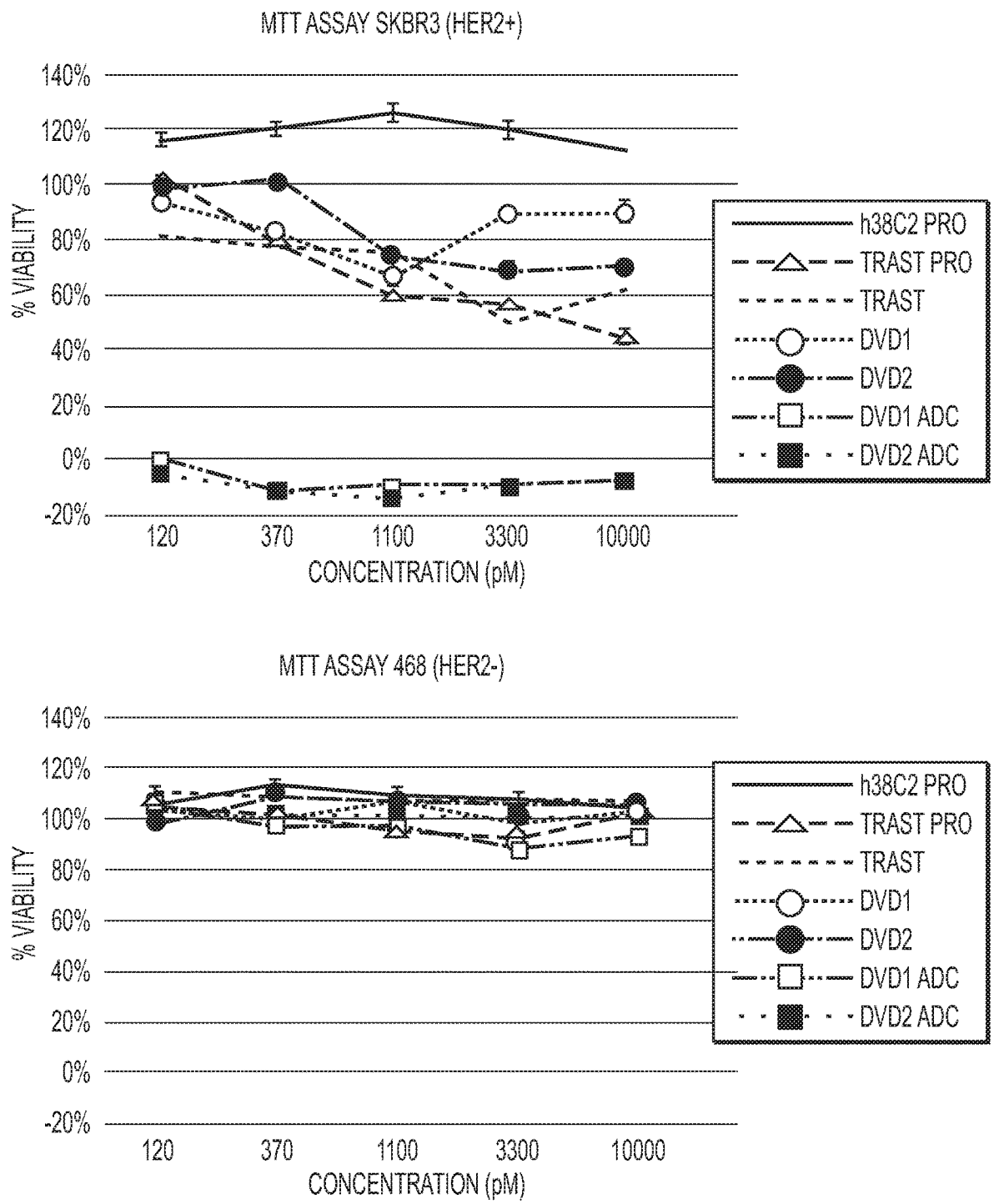
FIG. 19 depicts two graphs providing data from a second cytotoxicity assay demonstrating cell killing by an anti-HER2 dual variable domain immunoconjugate.

With reference to the graphs depicted in FIG. 19, h38C2 pro refers to an h38C2 antibody that has been conjugated to a β-lactam-hydrocarbon linker-MMAF composition but does not include a HER2 variable region binding domain; trast pro refers to the naked anti-HER2 antibody that has been mixed with a β-lactam-hydrocarbon linker-MMAF composition; trast refers to a naked anti-HER2 antibody (trastuzumab); DVD1 refers to the naked HER2-short peptide linker-h38C2-DVD1 immunoglobulin (i.e., with no linker/drug moiety composition conjugated thereto); DVD2 refers to the naked HER2-long peptide linker-h38C2-DVD2 immunoglobulin (i.e., with no linker/drug moiety composition conjugated thereto); DVD1 ADC refers to the DVD1 immunoglobulin with a β-lactam-hydrocarbon linker-MMAF attached thereto; and DVD2 ADC refers to the DVD2 immunoglobulin with a β-lactam-hydrocarbon linker-MMAF attached thereto.

With reference to the graphs depicted in FIG. 20, DVD1 refers to the naked HER2-short peptide linker-h38C2-DVD1 immunoglobulin (i.e., with no linker/drug moiety composition conjugated thereto); DVD2 refers to the naked HER2-long peptide linker-h38C2-DVD2 immunoglobulin (i.e., with no linker/drug moiety composition conjugated thereto); DVD1 ADC refers to the DVD1 immunoglobulin with a β-lactam-hydrocarbon linker-MMAF attached thereto; DVD2 ADC refers to the DVD2 immunoglobulin with a β-lactam-hydrocarbon linker-MMAF attached thereto; trast refers to a naked anti-HER2 antibody (trastuzumab); trast ADC refers to the naked anti-HER2 antibody that has been mixed with a β-lactam-hydrocarbon linker-MMAF composition; and h38C2 ADC refers to an h38C2 antibody that has been conjugated to a β-lactam-hydrocarbon linker-MMAF composition but does not include a HER2 variable region binding domain.

Cytotoxicity is assessed based on fluorescence using a plate reader (Spectramax M5) at 490 nM. Results are provided in the graphs in FIG. 18, FIG. 19 and FIG. 20.

Example 10: Molecular Weight Analysis of DVD Compositions

Figure 25:
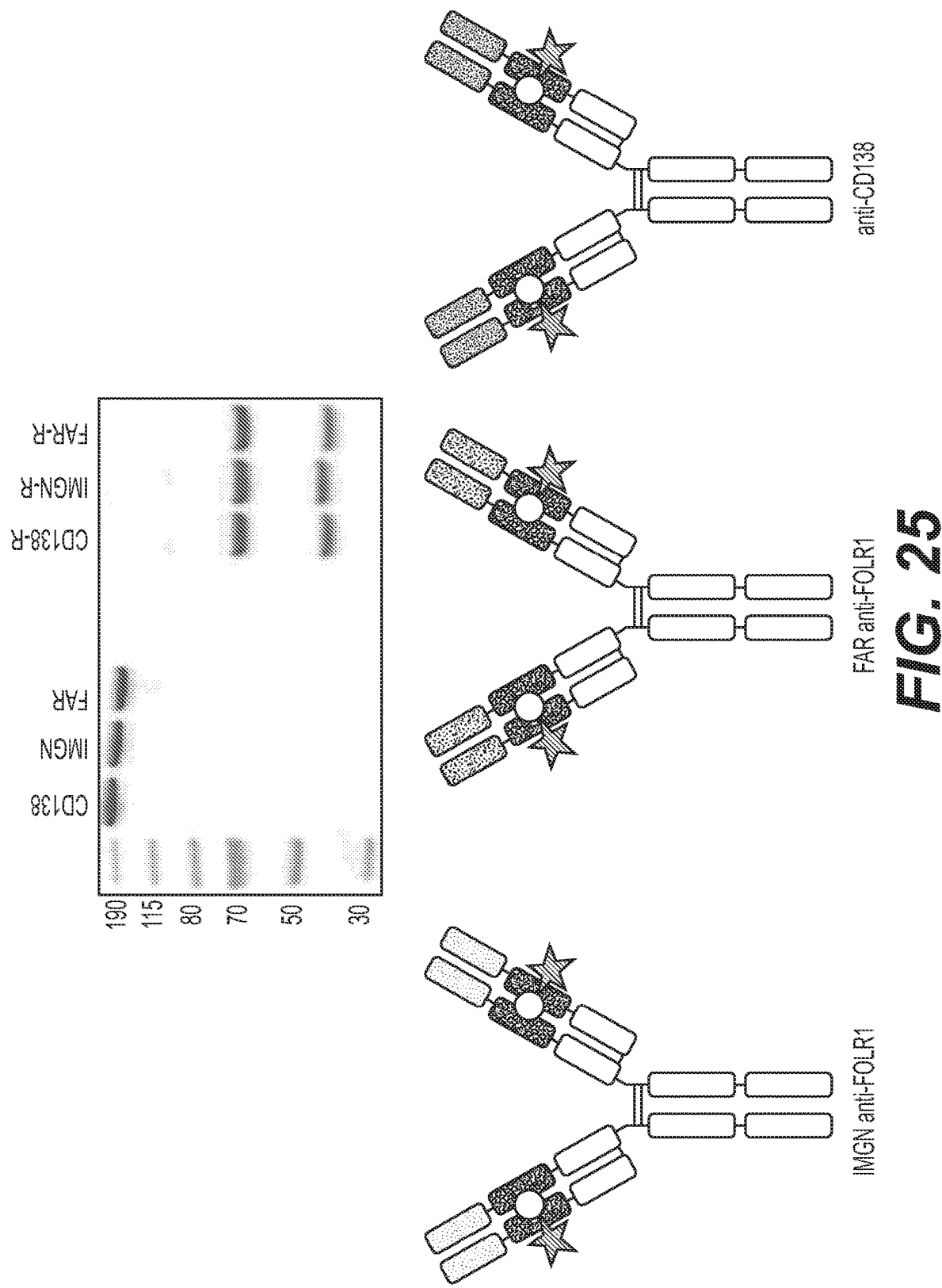
FIG. 25 provides schematic illustrations of the structure of IMGN anti-FOLR1, FAR anti-FOLR1, and anti-CD138 DVD ADCs, as well as Coomassie Gel data from unconjugated DVDs.
Figure 25:
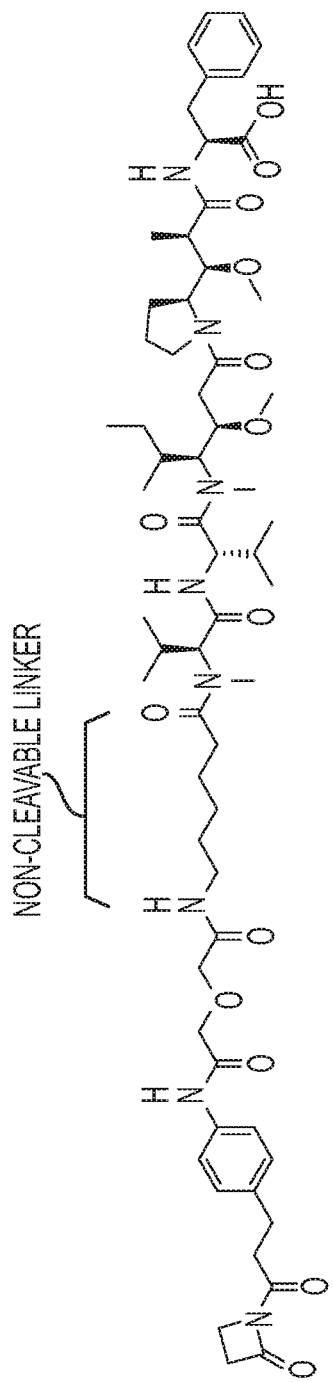

Purity of DVD compositions was confirmed using Coomassie stained SDS-PAGE under reducing (size=200 kDa) and nonreducing conditions (heavy chain=70 kDa, light chain=40 kDa) for both DVD1 and DVD2. Results are provided in FIG. 21 and FIG. 25.

Example 11: Selective Binding of DVD Compositions Demonstrated by Flow Cytometry DVD1 and DVD2 were incubated with SKBR3 (HER2+) or MDA-MB-468 (HER2−) for 30 min on ice then stained with AlexaFluor 647 conjugated F(ab')$_2$ goat anti-human (Jackson ImmunoResearch). Results are provided in FIG. 22. The results demonstrate that DVD1 and DVD2 compositions selectively bound to SKBR3 (HER+) cells.

Figure 23:
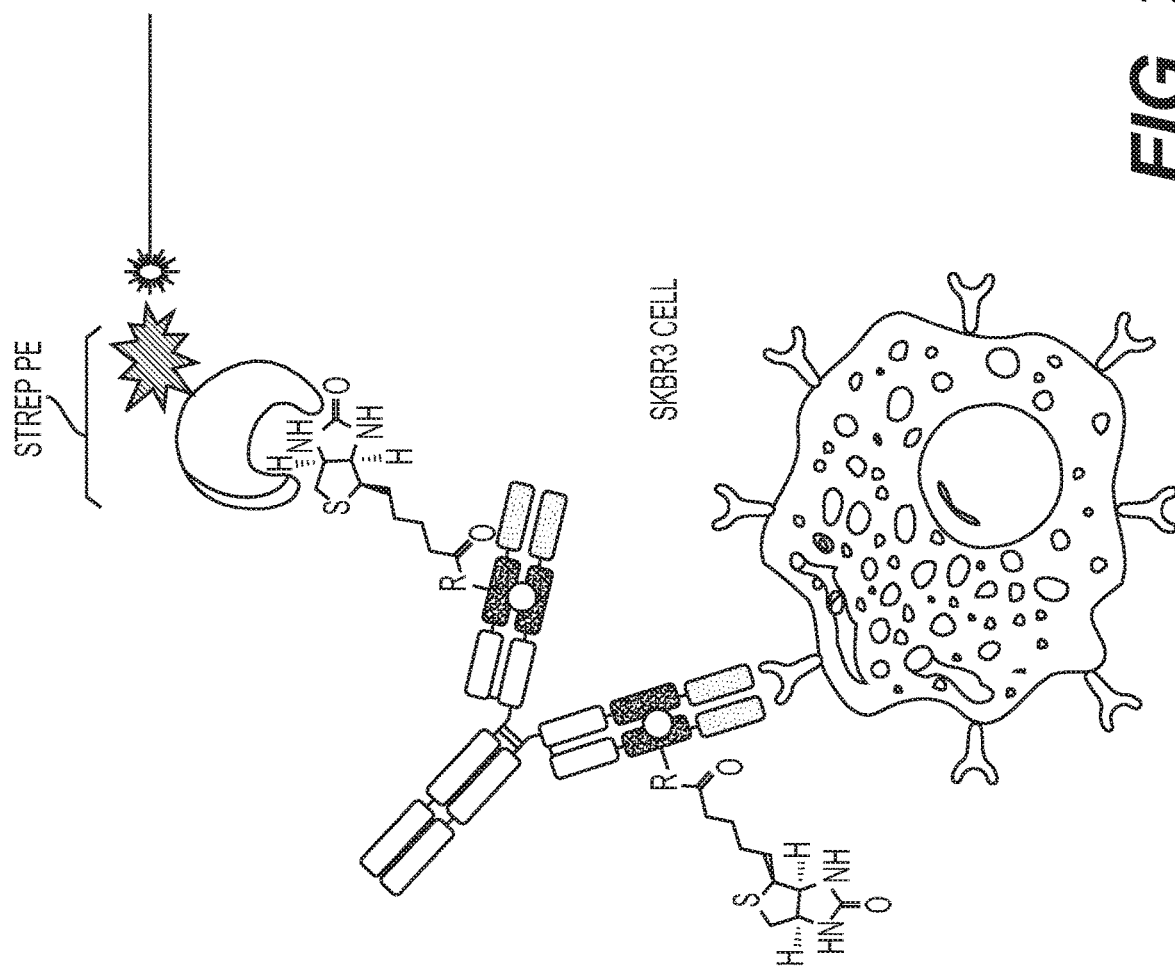
FIG. 23 provides a schematic illustration as well as flow cytometry data demonstrating β-lactam biotin labeling of DVD1 and DVD2 and binding to SKBR3 cells (HER2+) using streptavidin PE for detection. No detection was observed with MDA-MB-468 cells (HER2-).
Figure 23:
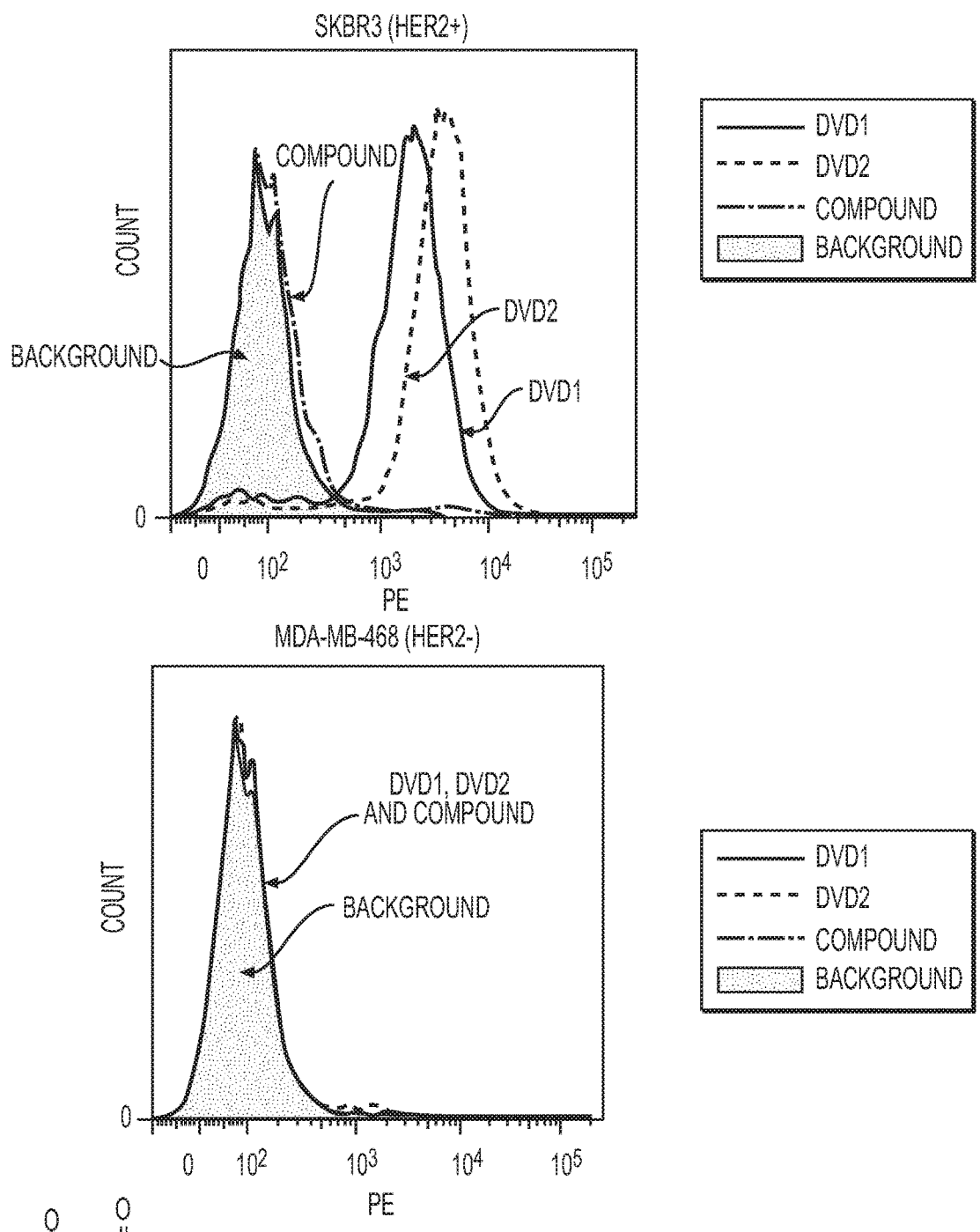

To examine non-specific binding of biotin β-lactam, DVD1 and DVD2 were incubated with 3 eq of biotin β-lactam (referred to as "Compound" in the figures) at room temperature for 2 hours, then incubated with SKBR3 (HER2+) or MDA-MB-468 (HER2-) for 30 min on ice and stained with PE conjugated Streptavidin (BioLegend). Results are provided in FIG. 23. The results demonstrate that DVD1 and DVD2 compositions selectively bound to SKBR3 (HER+) cells, whereas the biotin β-lactam compound did not bind to the HER2+ cells in a non-specific manner.

Figure 24:
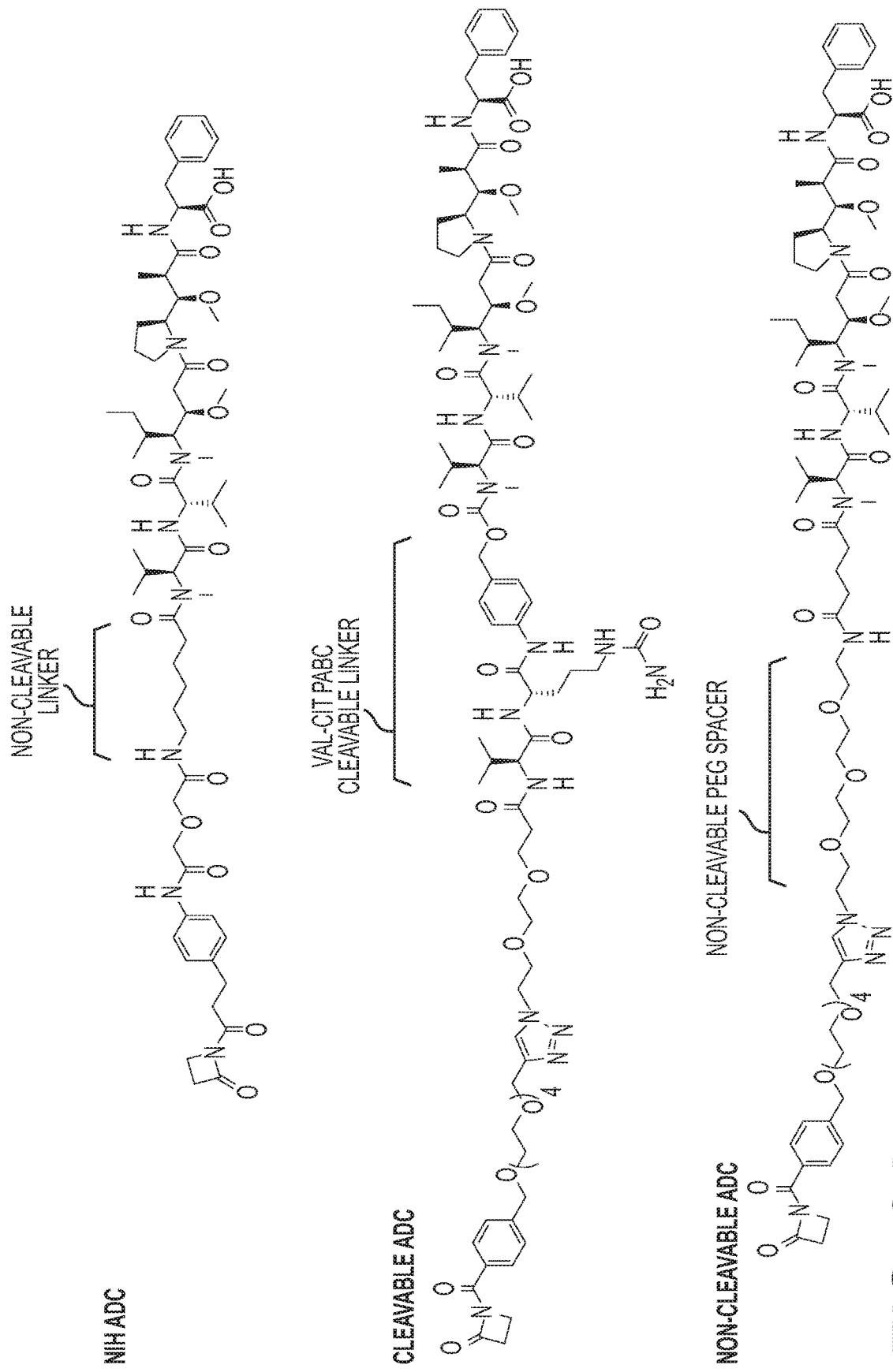
FIG. 24 provides graphical data that demonstrates cytotoxicity of anti-HER2 DVD1 ADC against SKBR3 (HER2+) and no cytotoxicity against MDA-MB-468 (HER2-) cells.
Figure 24:
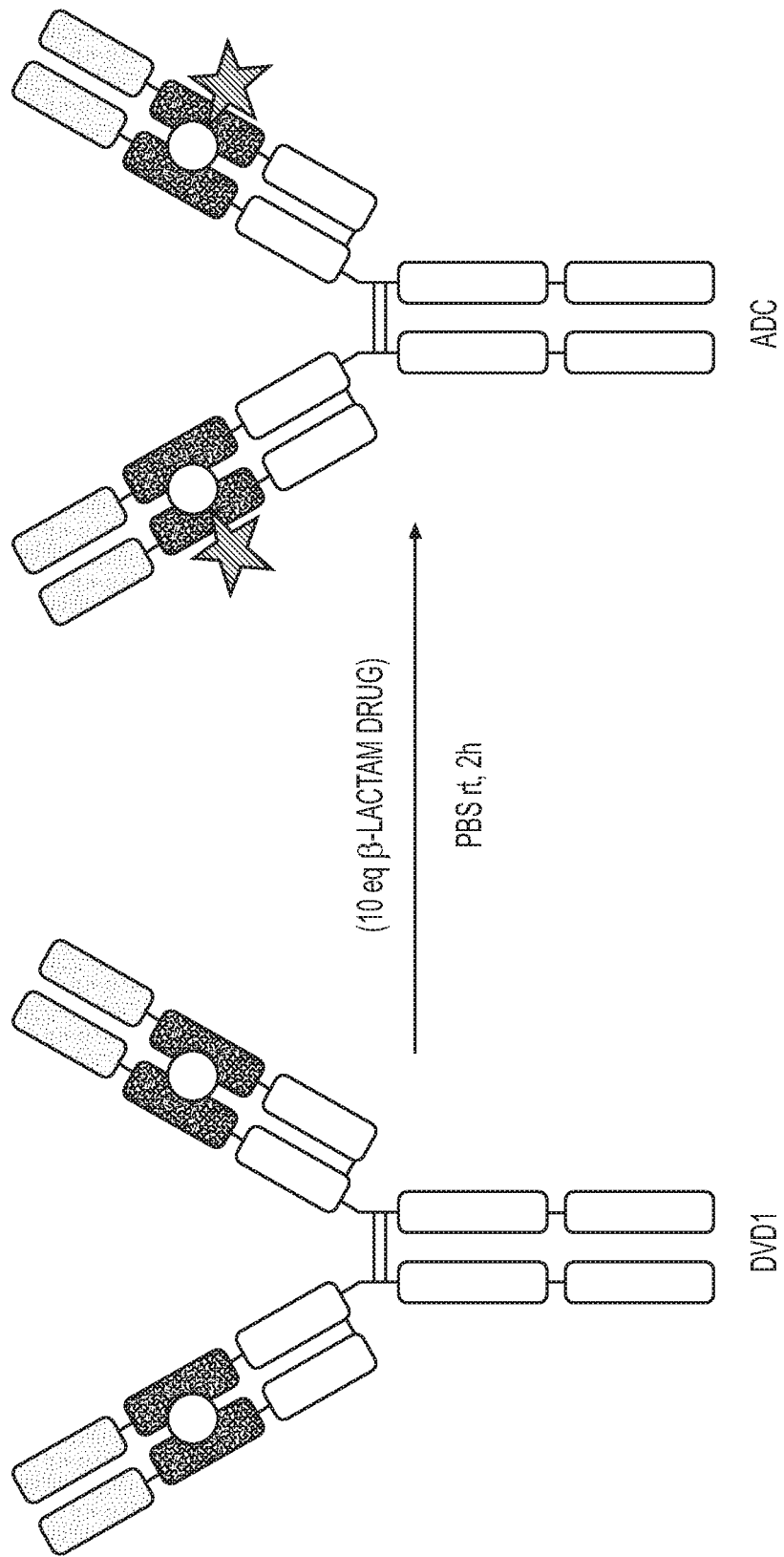
Figure 24:
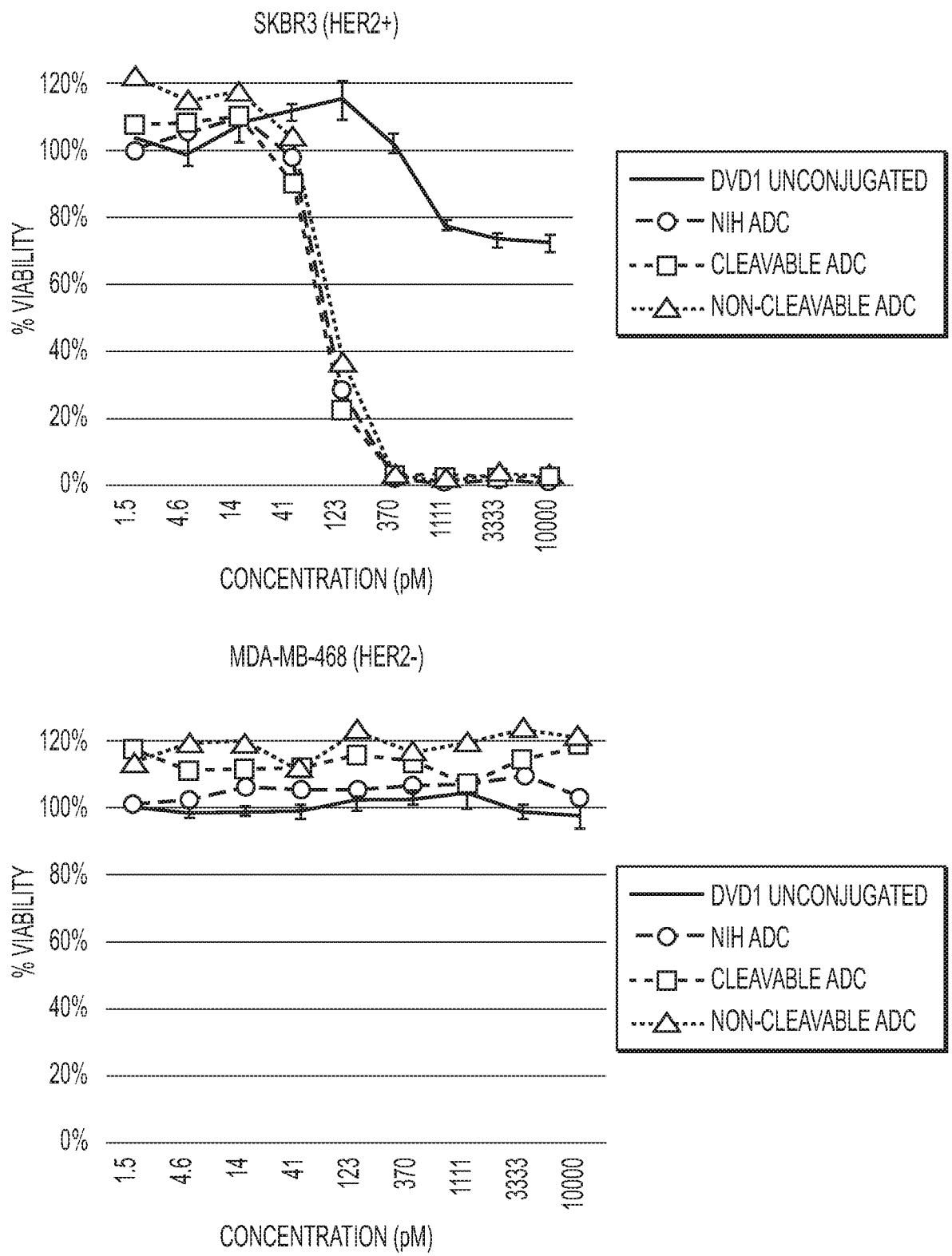
Figure 29:
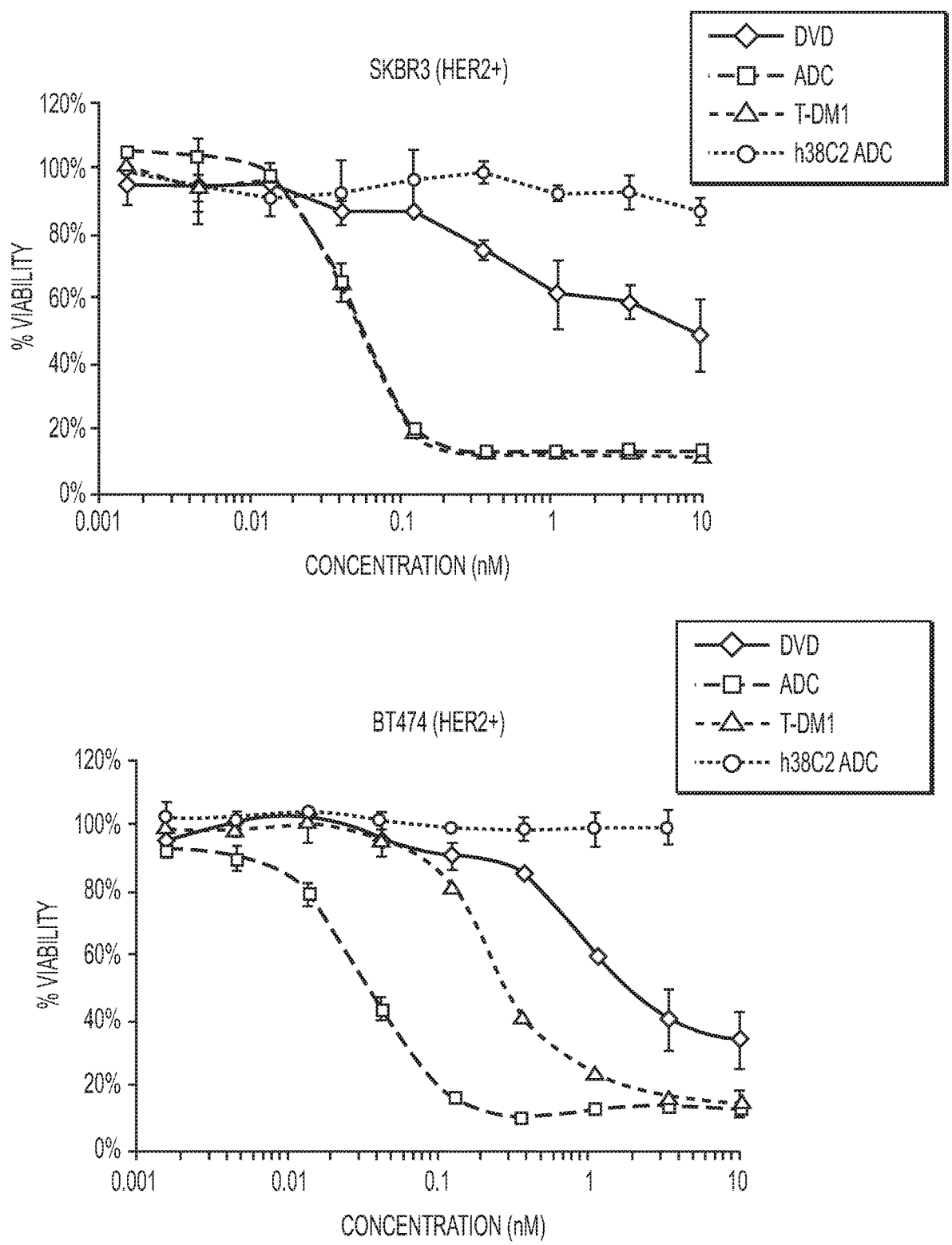
FIG. 29 provides graphical data that demonstrates cytotoxicity of DVD1-ADC against SKBR3, BT474, KPL4, DYT2, and MDA-MB-468 cells.
Figure 29:
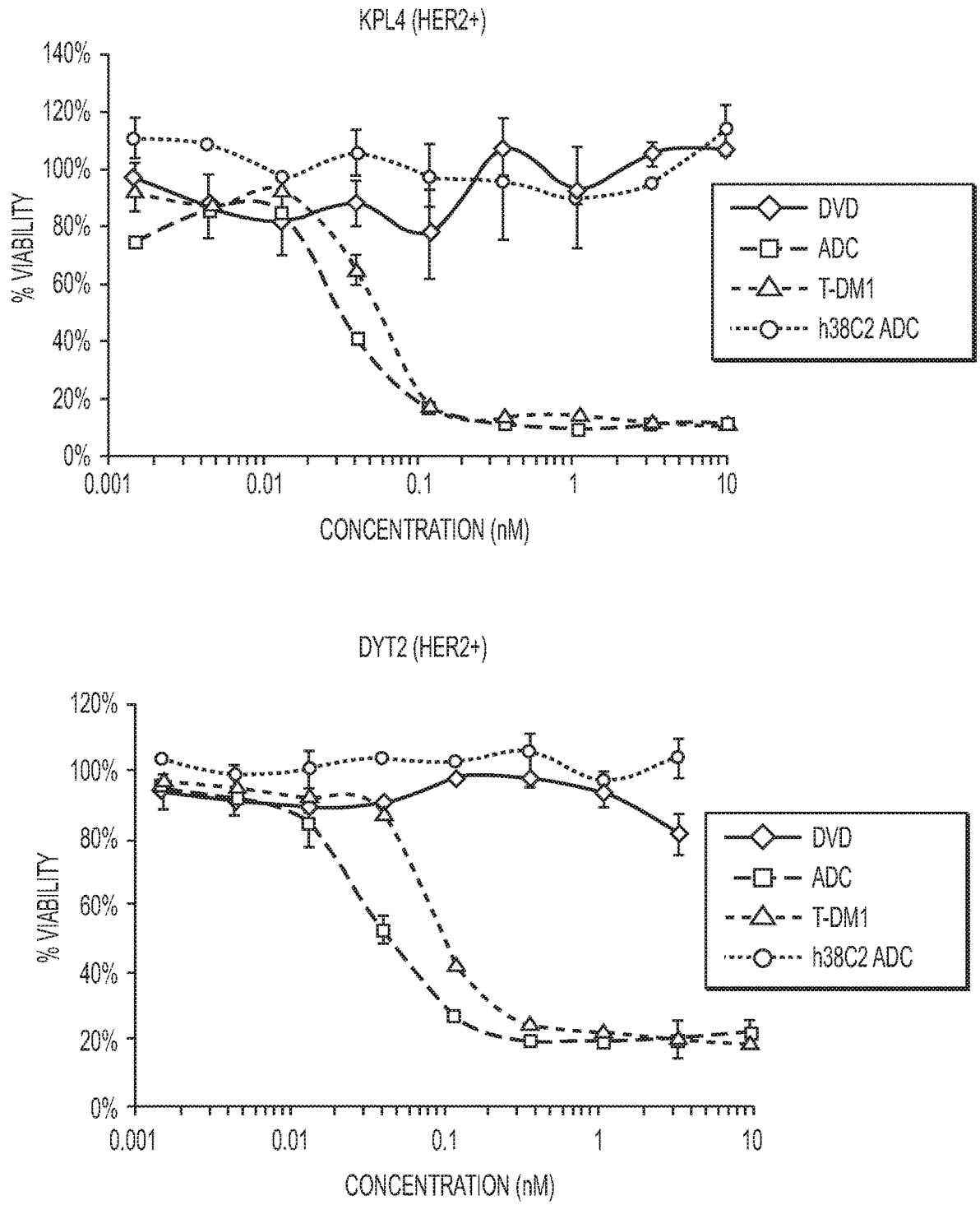
Figure 29:
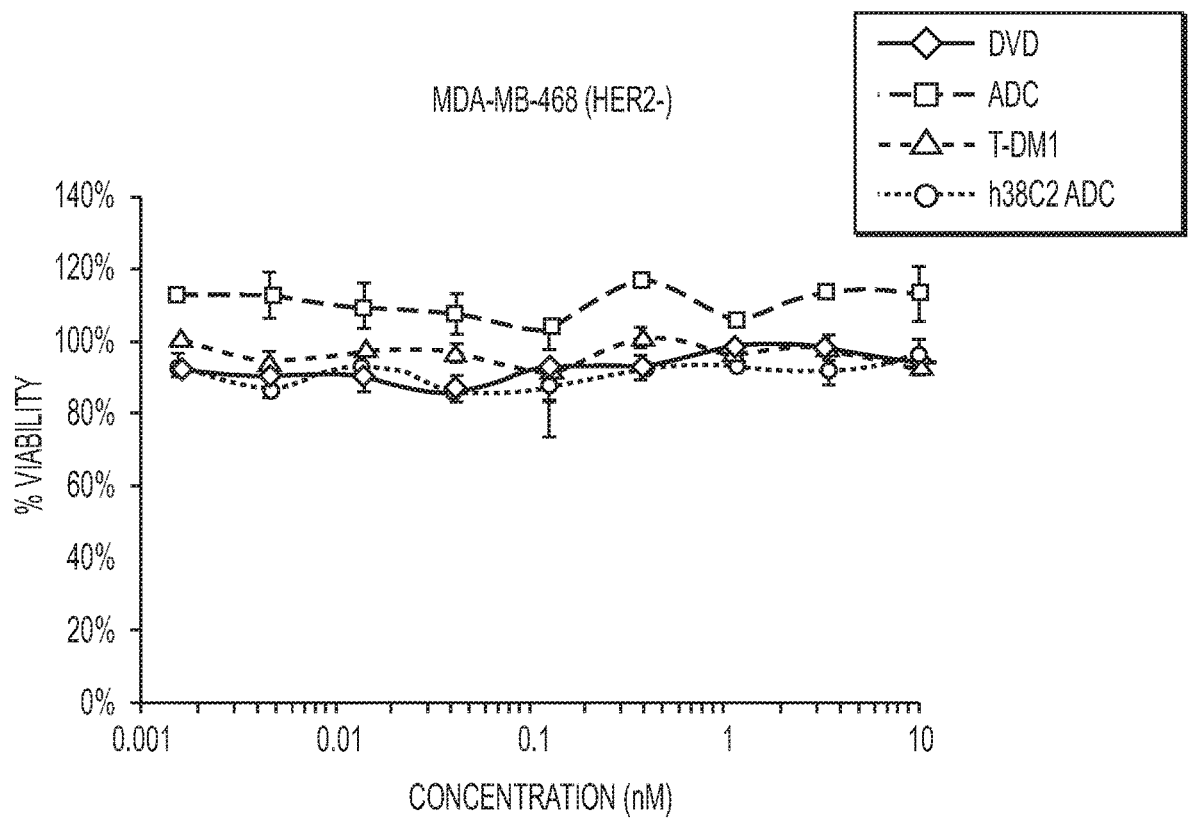

Example 12: Cytotoxicity of ADCs Against SKBR3 (HER2+), BT474 (HER2+), KPL4 (HER2+), DYT2 (HER2+), and MDA-MB-468 (HER2-) Cells Indicated cell types were plated in 96-well plates at 5×10$^3$ cells per well. Cells were allowed to adhere overnight. Serial dilutions of ADCs were added to the cells at concentrations ranging from 0 to 10 nM. After incubation for 72 h, the cell viability was measured using the CellTiter 96 AQueous One Solution Cell Proliferation Assay (Promega) following the manufacturer's instructions. The cell viability was calculated as a percentage of untreated cells 100%). Results are provided in FIG. 24 and FIG. 29. The results demonstrate that the ADCs had cytotoxic activity against HER2+ cells.

Figure 26:
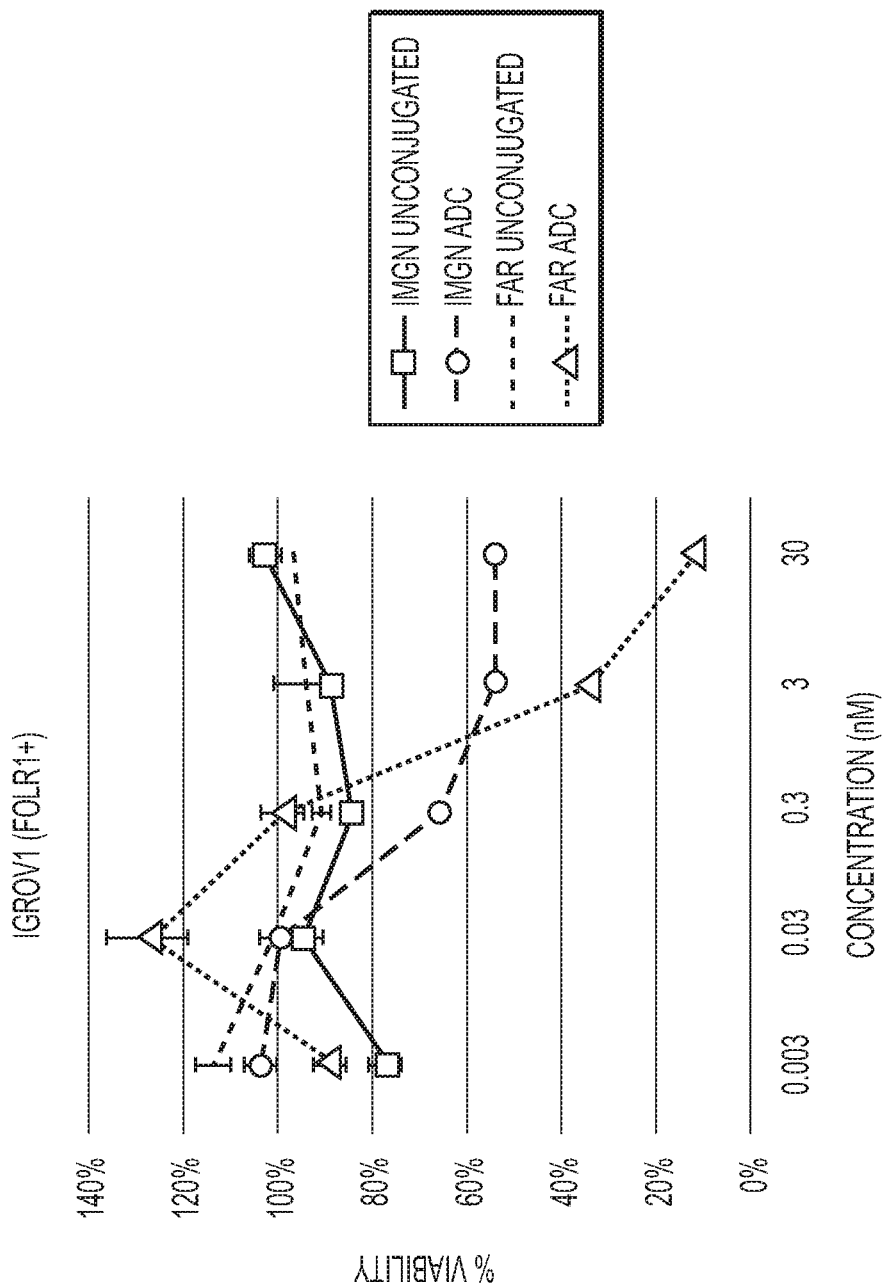
FIG. 26 provides graphical data that demonstrates cytotoxicity of anti-FOLR1 ADCs against IGROV1 (FOLR1+) cells.
Figure 27:
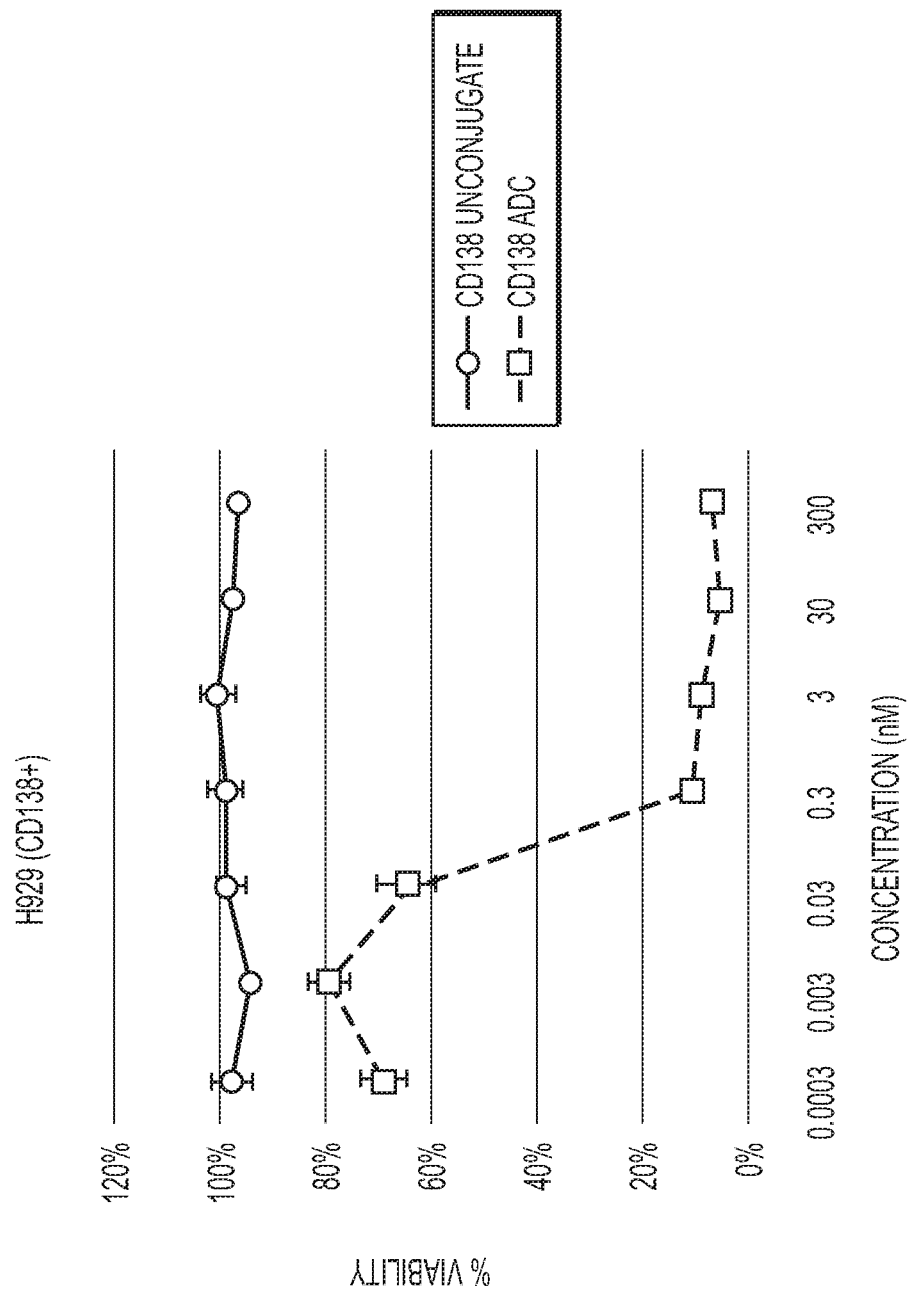
FIG. 27 provides graphical data that demonstrates cytotoxicity of anti-CD138 ADC against H929 (CD138+) cells.

Example 13: Cytotoxicity of ADCs Against IGROV1 (FOLR1+) and 11929 (CD138+) Cells Human cancer cell lines IGROV1 (FOLR1+) and H929 (CD138+) were maintained at 37° C. in a humidified 5% CO$_2$ atmosphere in DMEM or RPMI completed with 10% FBS and 1% Pen Strep. IGROV cells were harvested using TrypLE (Life Technologies) and transferred to a Flat-Bottom 96-well tissue culture plate (5000 cells/well) 24 h before treatment. H929 cells were treated immediately. Serial dilutions were prepared in DMEM or RPMI completed with 10% FBS and 1% Pen Strep. For IGROV1 cells, original cell media was removed and 100 µl of treatment solution was added (performed in triplicate) and the culture plate was maintained at 37° C. in a humidified 5% CO$_2$ atmosphere for 72 h. For H929 100 µl of treatment solution was added. The cells were then contacted with an immunoconjugate, or with one of several control compositions. 20 µl of CellTiter 96® Aqueous One Solution (Promega) was added to each well and the plate was developed at 37° C. in a humidified 5% CO$_2$ atmosphere. Results are provided in FIG. 26 and FIG. 27. The results demonstrate that the immunoconjugates had cytotoxic activity against the target cell types.

Example 14: Catalytic Activity of DVD Compositions

Figure 32:
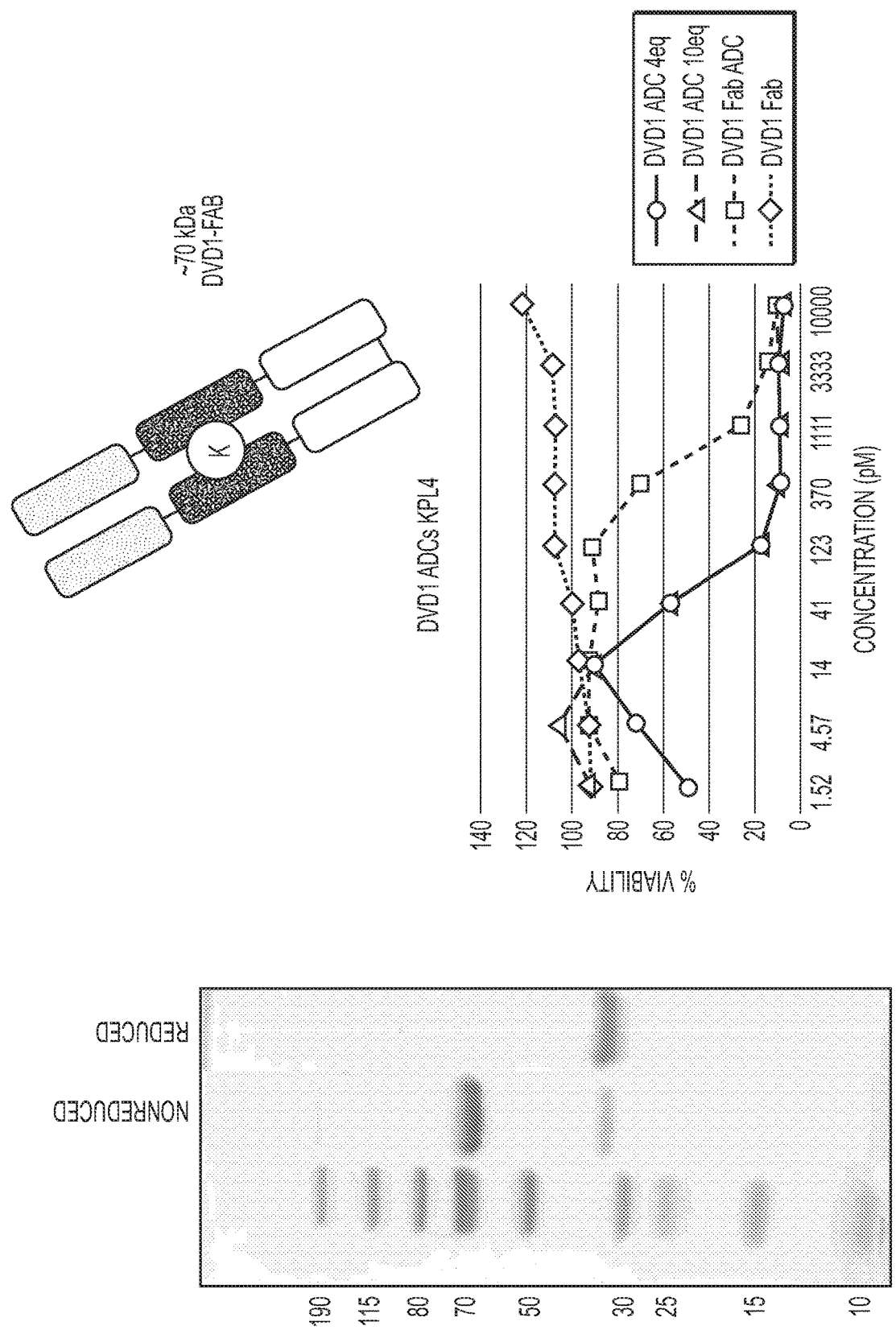
FIG. 32 provides a schematic illustration of a non-limiting example of a DVD1-Fab composition, as well as Coomassie Gel data, catalytic activity data, and cytotoxicity data against KPL4 (HER2+) cells.
Figure 34:
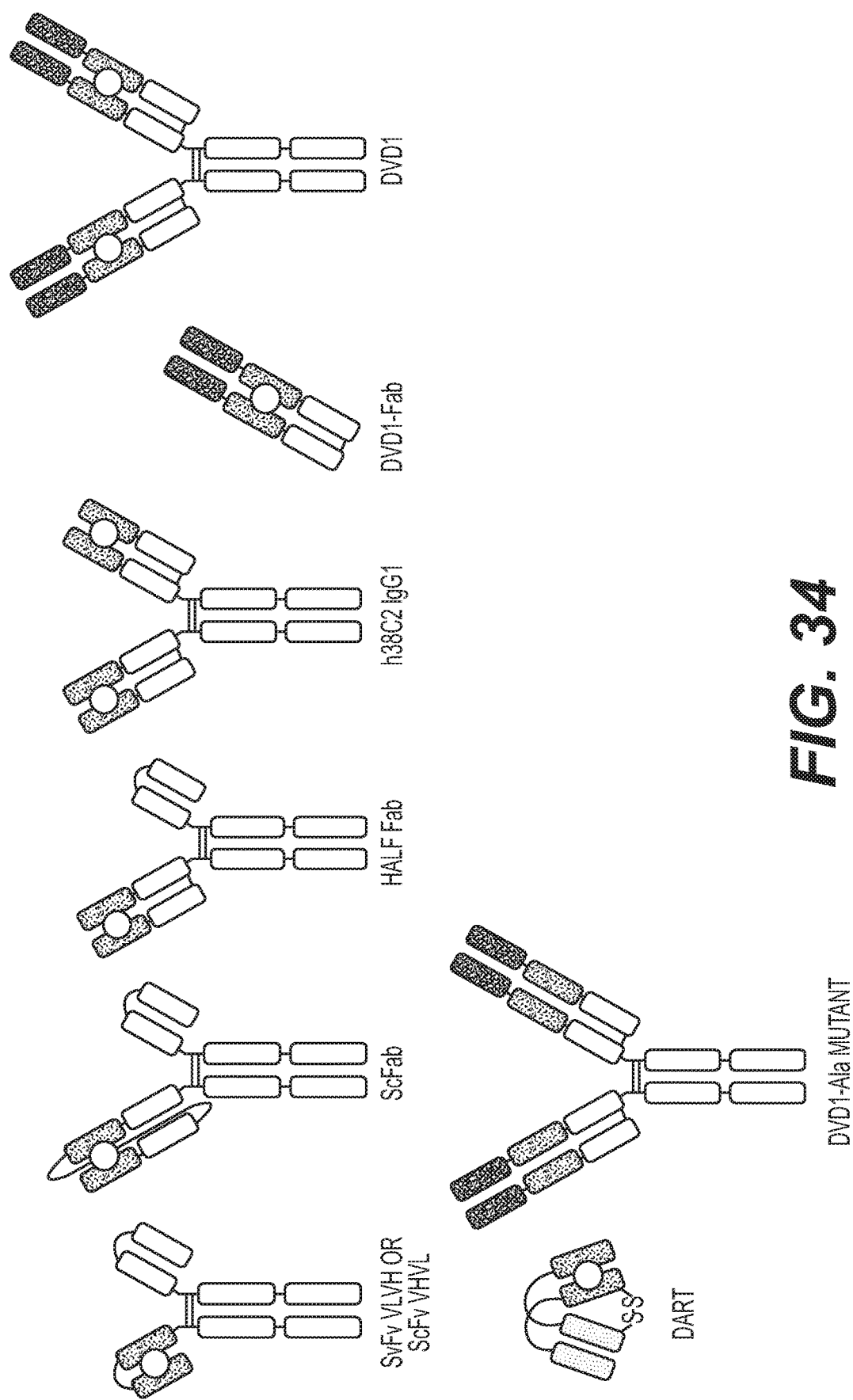
FIG. 34 provides schematic illustrations of various non-limiting examples of DVD compositions.

98 µl of antibody (1 µM in PBS) was dispensed in a 96-well plate. 2 µl of Methodol (10 mM in EtOH) was then added and the excitation ($\lambda_{ext}$=330 nM) and emission ($\lambda_{en}$=452 nM) was recorded every 5 min using a spectrofluorometer. To 548 µl DVD1 (10.33 mg/ml, 51.7 µM) was added 11.3 µl (10 mM in DMSO) β-lactam MMAF (4 eq with respect to antibody). The solution was vortexed, incubated at room temperature for 4 hours, and purified using a PD-10 desalting column (GE Healthcare). The conjugates in PBS were stored at 4° C. for short term use and at −80° C. in aliquots for long term use. Antibody concentrations were determined based on the absorbance at 280 nM. h38C2 IgG1 was used as a positive control using the same conjugation conditions. The catalytic activity was assessed using a known assay, as described in Sinha, S.C. Nature Protocols 2, 449-456 (2007), the disclosure of which is incorporated herein by reference in its entirety. Unconjugated DVD1 and h38C2 IgG1 were used as positive controls. Trastuzumab IgG1 was used as a negative control. Schematic illustrations of various DVD compositions are provided in FIG. 34. Results of the catalytic activity assay are provided in FIG. 28, FIG. 32, and FIG. 35. The results demonstrate that the catalytic activity of each composition correlates with the number of available reactive lysine residues. For example, as provided in FIG. 35, h38C2-IgG1 (which has 2 variable domains that each contain 1 reactive lysine residue) exhibited roughly twice the catalytic activity of DVD1-Fab (which has 1 variable domain that contains 1 reactive lysine residue). The catalytic activity of certain compositions (e.g., the scFv and DART format compositions, which as depicted in FIG. 34) showed diminished catalytic activity when compared to the Fab, scFab, IgG, and their corresponding DVD format compositions. The compositions that have no reactive lysine residues (e.g., Trastuzumab) showed no catalytic activity.

Example 15: Mass Spectroscopy Analysis of DVD Compositions

Figure 33:
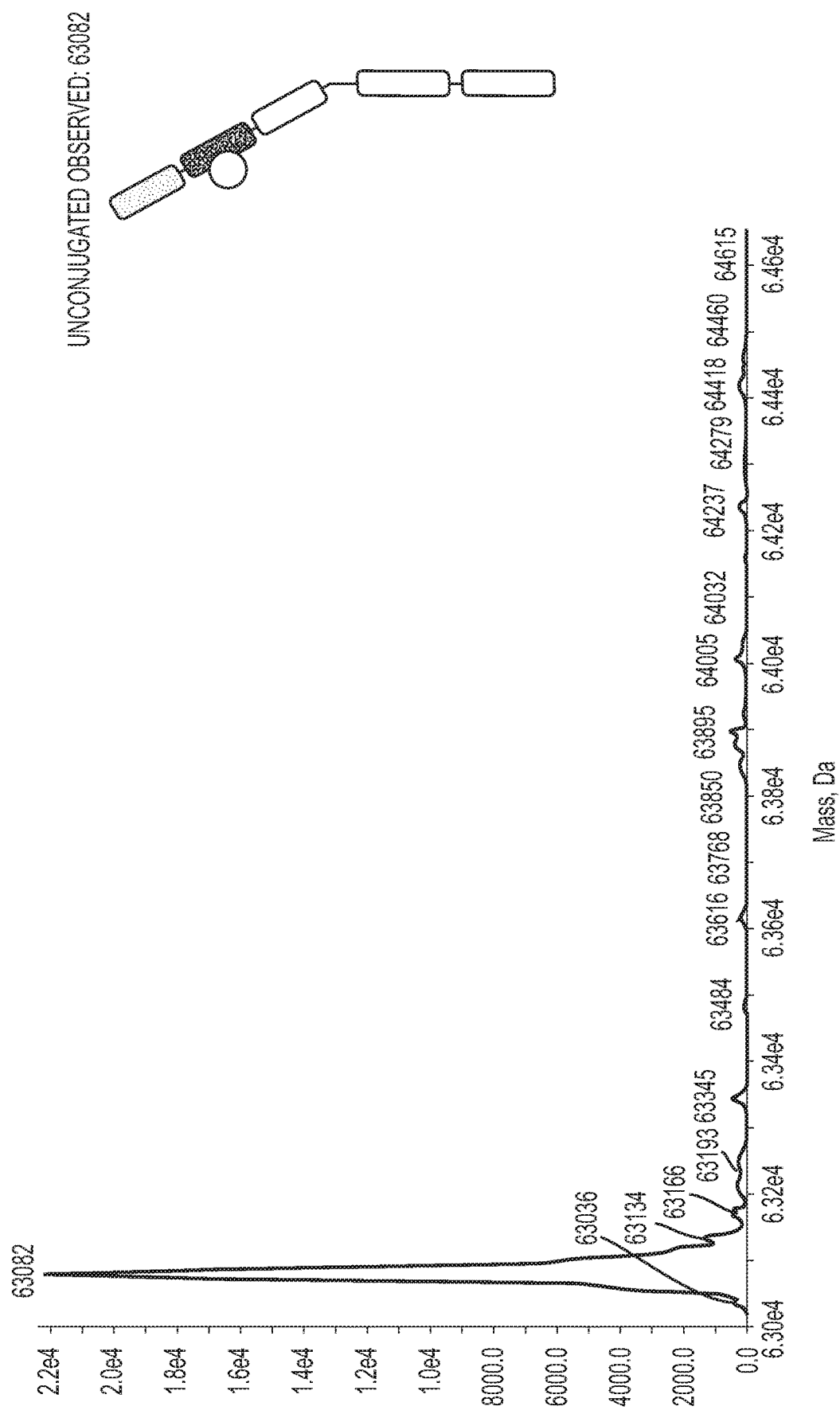
FIG. 33 provides MALDI-TOF mass spectroscopy data from DVD1 and DVD1-ADC heavy chains.
Figure 33:
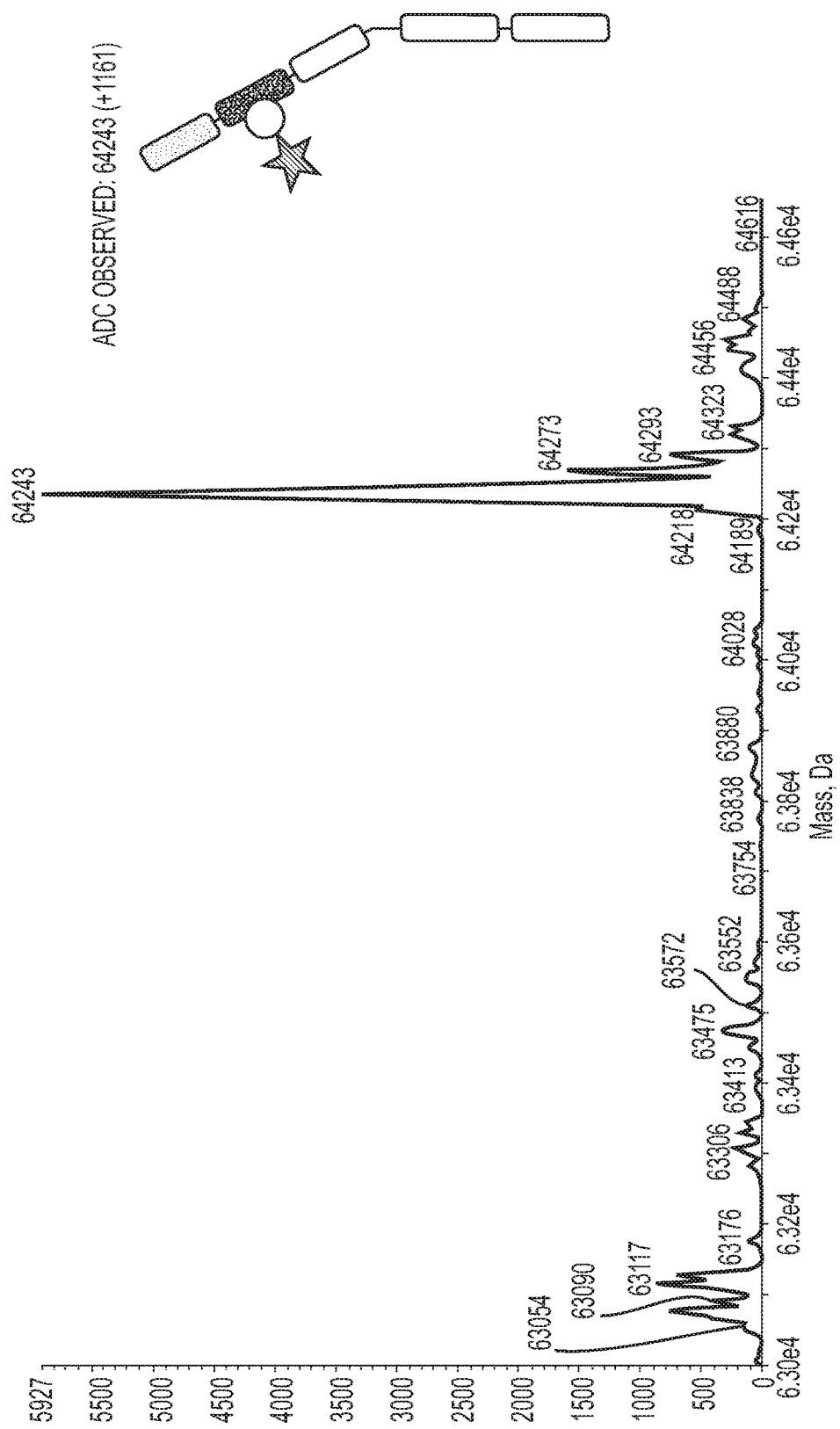

Unconjugated DVD1 and Antibody-Drug Conjugate (ADC) were deglycosylated using PNGase F (New England Biolabs) according to the manufacturer's instructions, reduced using DTT (final concentration was 50 mM DTT), and analyzed using MALDI-TOF Mass Spectrometry. The mass of the ADC heavy chain corresponded with 1 drug per heavy chain, demonstrating precise conjugation of a defined number of drug molecules per DVD. Results are provided in FIG. 33.

Example 16: In Vivo Cytotoxicity of DVD Compositions

Figure 30:
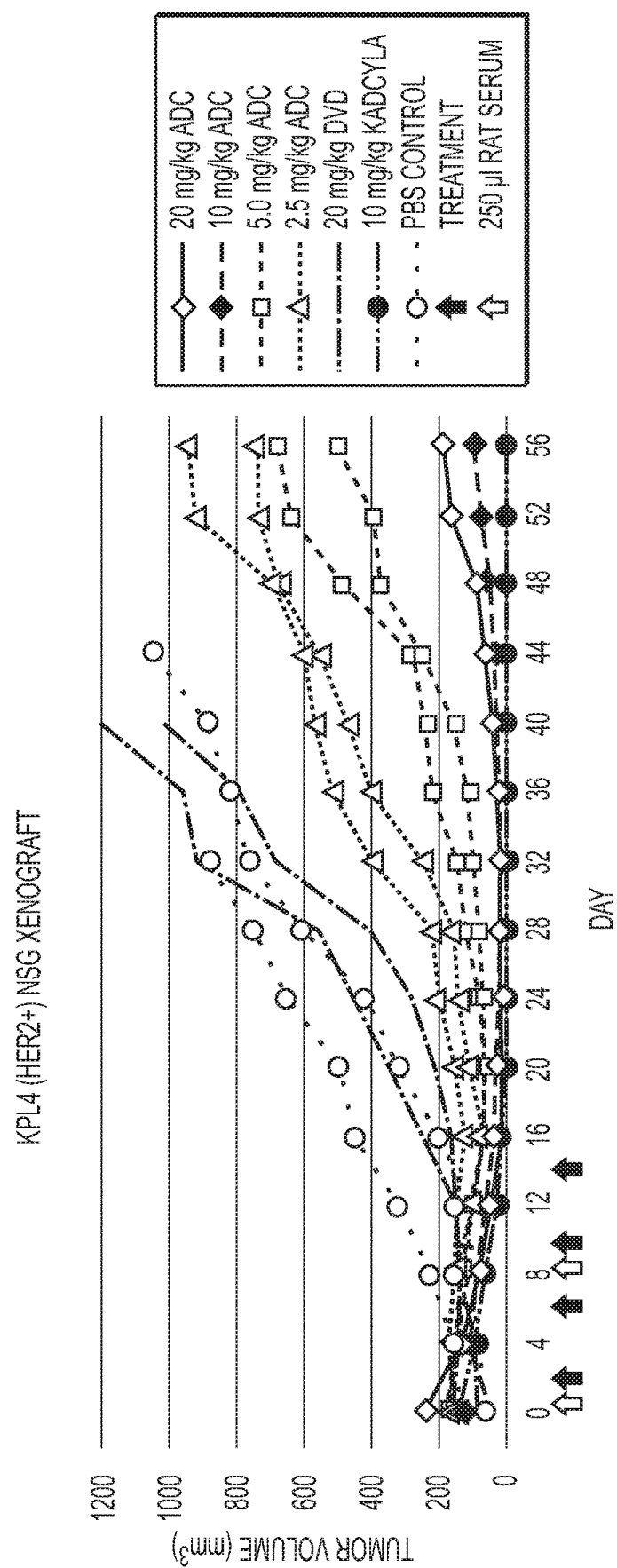
FIG. 30 provides graphical data depicting tumor volume as a function of dose in an in vivo xenograft model of KPL4-implanted NSG mice (n=2 per group) and dose response with DVD1-ADC.

KPL-4 (HER2+) cells in 1:1 mixture of PBS and BD Matrigel (BD Bioscience) were inoculated subcutaneously into the mammary fat pad of 7-weeks old female NSG mice (Jackson Laboratory) (5×10⁶ per mouse). When tumors reached ~200 mm³, the mice were randomly assigned to 7 groups of 2 mice each and treated with anti-HER2 DVD1 ADC at 2.5, 5.0, 10, or 20 mg/kg, or with unconjugated anti-HER2 DVD1 at 10 mg/kg, or with vehicle (PBS) alone, or with ado-trastuzumab emtansine biosimilar (Levena Biopharma) at 10 mg/kg via i.v. (tail vein) injection every 4 days for a total of 4 cycles (*Note: the 20 mg/kg ADC group was only 1 cycle). The mice were pre-dosed with 250 µl of sterile rat serum 1 day before 2/4 injections. The tumor size was monitored every 4 days via caliper measurement. All procedures were approved by the Institutional Animal Care and Use Committee of The Scripps Research Institute and were performed according to the NIH Guide for the Care and Use of Laboratory Animals. Results are provided in FIG. 30. The results demonstrate that the ADCs were able to reduce tumor volume as compared to vehicle control (e.g., PBS).

Figure 31:
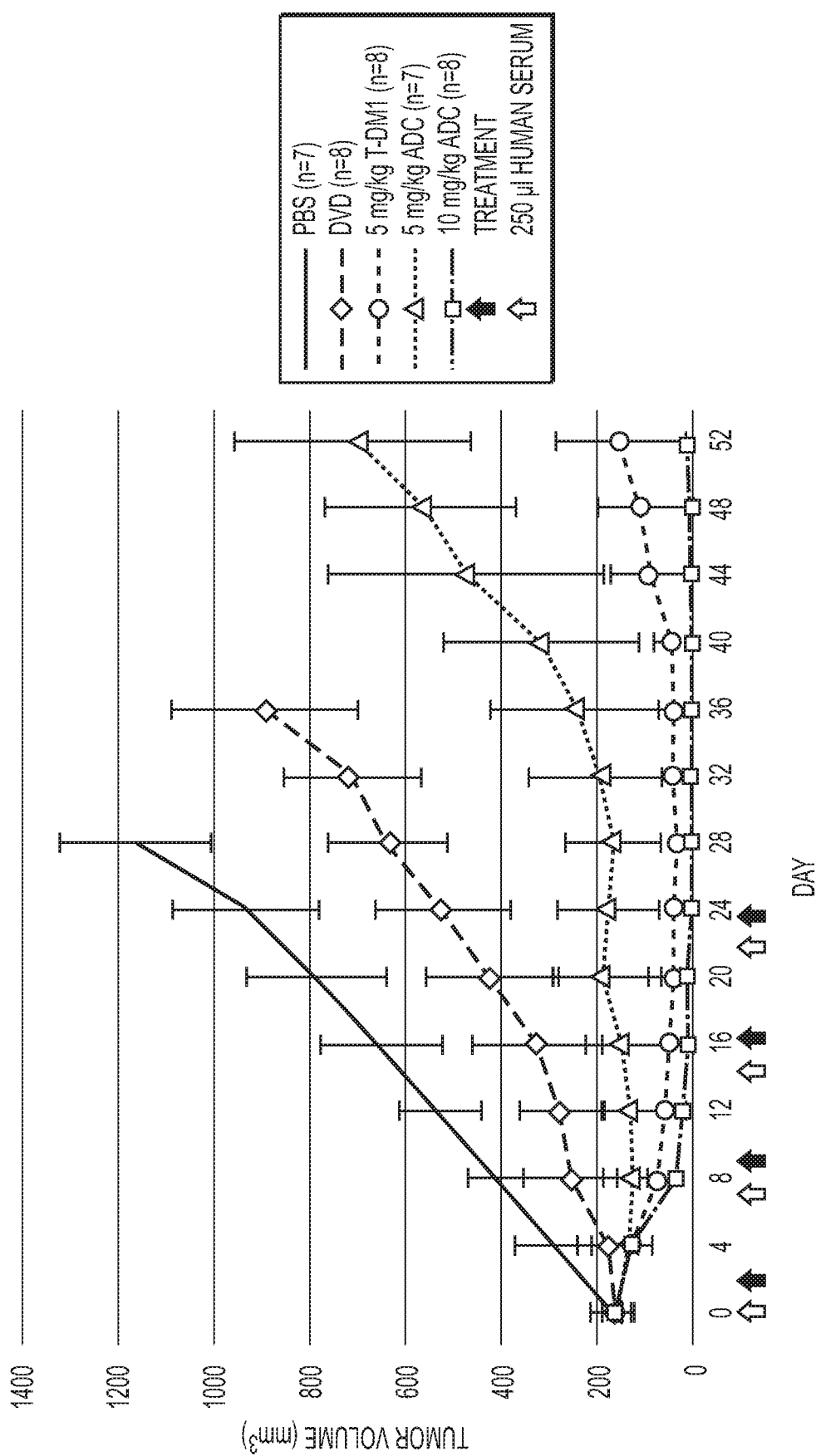
FIG. 31 provides graphical data depicting tumor volume as a function of dose in an in vivo xenograft of KPL4-implanted NSG mice (n=7 or 8 per group).

KPL-4 (HER2+) cells in 1:1 mixture of PBS and BD Matrigel (BD Bioscience) were inoculated subcutaneously into the mammary fat pad of 7-weeks old female NSG mice (Jackson Laboratory) (6×10⁶ per mouse). When tumors reached ~200 mm³, the mice were randomly assigned to 5 groups of 7 or 8 mice each and treated with anti-HER2 DVD1 ADC at 5 or 10 mg/kg, or with unconjugated anti-HER2 DVD1 at 10 mg/kg, or with vehicle (PBS) alone, or with ado-trastuzumab emtansine biosimilar (Levena Biopharma) at 5 mg/kg via i.v. (tail vein) injection every 7 days for a total of 4 cycles. The mice were pre-dosed with 250 µl of sterile human serum (Sigma Aldrich) 1 day before every injection. The tumor size was monitored every 4 days via caliper measurement. All procedures were approved by the Institutional Animal Care and Use Committee of The Scripps Research Institute and were performed according to the NIH Guide for the Care and Use of Laboratory Animals. Results are provided in FIG. 31. The results demonstrate that the ADCs were able to reduce tumor volume as compared to vehicle control (e.g., PBS).

Example 17: DVD1-Fab Cloning, Expression, Purification, Catalytic Activity, and Cytotoxicity PCR fragments were cloned into mammalian expression vector pCEP4 (Invitrogen) by Nhe1-HF/Xho1 ligation. The heavy chain contained the first constant domain of human IgG1 (CH0 at the C-terminus. The light chain contained the first constant domain of human C kappa ($C_k$) at the C-terminus. The mammalian cell expression vectors were transiently co-transfected (light and heavy chain) into Human Embryonic Kidney (HEK) 293 cells (Life Technologies) with polyethylenimine (PEI). The DVD1-Fab composition was purified using a HiTrap Protein A HP column (GE Healthcare). Typical yields were 10 mg/L. SDS-PAGE was used to confirm purity, and catalytic activity was evaluated as described in Example 14. h38C2 IgG1 was used as a positive control, and trastuzumab IgG1 was used as a negative control. Cytotoxicity was assessed as described in Example 12. Results are provided in FIG. 32. As expected, the DVD1-Fab composition had roughly ½ the catalytic activity of the h38C2-IgG1 composition. The cytotoxicity data demonstrates that both the DVD1-ADC and the DVD1-Fab-ADC had cytotoxic activity against HER2+ cells. As expected, due to the lower amount of drug on the DVD1-Fab-ADC as compared to the DVD1-ADC composition, the cytotoxic activity of the DVD1-Fab-ADC was lower than that of the DVD1-ADC composition.

Example 18: DVD2-Fab Cloning, Expression, Purification, and Catalytic Activity

Anti-HER2 DVDs are prepared by linking the $V_H$ and $V_L$ of trastuzumab to the $V_H$ and $V_L$ of h38C2 via a short (ASTKGP) or long (TVAAPSVFIFPP) linker for DVD1 and DVD2 respectively. The anti-CD138 and anti-CD79b DVDs are expressed using the short (ASTKGP) linker. The desired sequences are synthesized as gBlocks (Integrated DNA Technologies) and expressed with a human IgG1 heavy chain or k light chain constant domain. The DVD expression cassettes are NheI/XhoI-cloned into mammalian expression vector pCEP4 and transiently transfected into HEK 293 cells for production. The supernatants are collected 3 times over a 9-day period followed by filtration and purification using 1-mL HiTrap Protein A HP columns (GE Healthcare Life Sciences) in conjunction with an ÄKTA FPLC instrument (GE Healthcare Life Sciences). Yields are typically 10 mg/L. The purity of DVDs is confirmed by SDS-PAGE followed by Coomassie staining, and the concentration was determined by measuring the absorbance at 280 nm. To ensure the Lys reactivity of h38C2 is retained in DVD format, its activity was assessed directly using an assay relying on its catalytic aldolase activity to convert methodol to its parent aldehyde via a retro-aldol reaction. The formation of the fluorescent aldehyde is quantified using a fluorometer.

Specifically, DVDs or IgG1s are diluted to 1 µM in PBS (pH 7.4) and are dispensed in 98-µl aliquots into a 96-well plate in triplicate. Then, 2 µl of 10 mM methodol in ethanol is added and the fluorescence is assessed immediately using a SpectraMax M5 instrument (Molecular Devices) with SoftMax Pro software, a wavelength of excitation ($\lambda_{ext}$) set to 330 nm, a wavelength of emission ($\lambda_{em}$) set to 452 nm, and starting at 0 min using 5-min time points. The signal is determined by normalizing to 98 µL PBS with 2 µL of the methodol preparation added.

Figure 36:
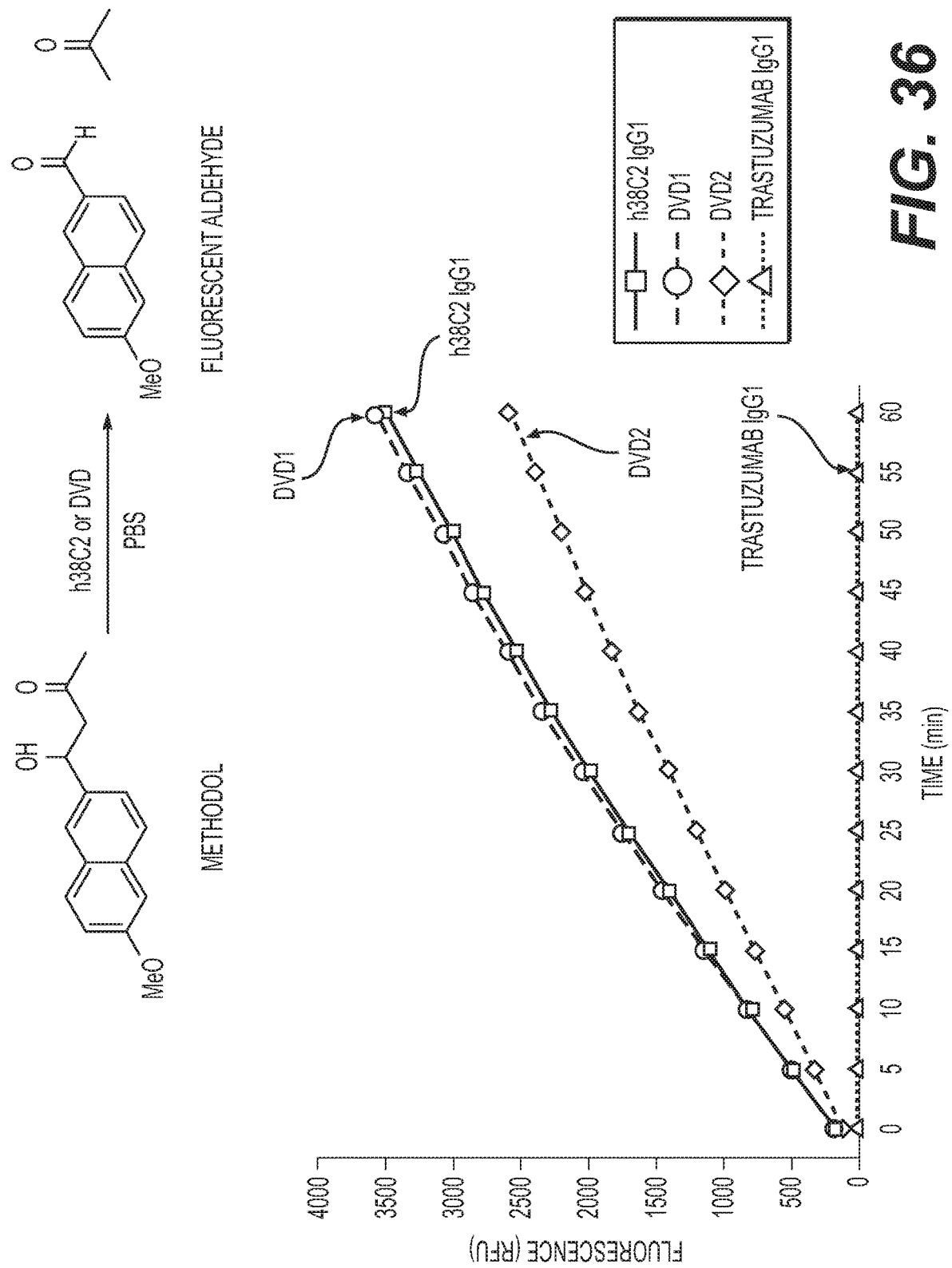
FIG. 36 provides graphical data that demonstrates catalytic activity of various compositions, including h38C2, DVD1, DVD2, and trastuzumab.

FIG. 36 shows activity of the h38C2 lysine being measured directly using methodol as a substrate, which is converted to a fluorescent aldehyde and detected. DVD1 had equal activity to parent h38C2 IgG1 with DVD2 having decreased activity. Trastuzumab IgG1 is used as a negative control.

Example 19: Generation of DVD Based Drug Conjugates and Evaluation of their Activity Against HER2+ Breast Cancer Cell Lines In Vitro To prepare the desired ADC, a β-lactam functionalized monomethyl auristatin F (MMAF) compound with a noncleavable linker is synthesized (FIG. 37A). The β-lactam handle is used for conjugation because it reacts irreversibly with the Lys of h38C2 by forming a stable amide bond, thus preventing the possibility of premature drug release. MMAF is chosen with a noncleavable linker because this payload has been used to prepare potent ADCs against a variety of targets and noncleavable linkers have been reported to have higher maximum tolerated doses. ADCs are prepared by incubating DVD1 with 4 equivalents of β-lactam MMAF (2 equivalents with respect to each Lys residue) in PBS for 4 hours (FIG. 37B). FIG. 44 provides a solid-phase synthesis scheme of β-lactam MMAF. Since the Lys reacts with the β-lactam moiety to form an amide bond, the Lys is no longer catalytically active, thus complete conjugation is confirmed by loss of catalytic activity (FIG. 37C).

All conjugations are performed in PBS (pH 7.4) after the antibodies are concentrated to 50 μM (10.0 mg/mL) using a 30-kDa cutoff centrifugal filter device. 6.0 μl of β-lactam-MMAF (1 mM of a 10% DMSO solution in PBS, 4 eq) is added to 300 μg of antibody for a final reaction volume of 36 μl. The solution is incubated for 4 hours at room temperature. All conjugations are deemed complete by loss of catalytic activity using the methodol assay using a portion of the crude reaction diluted to 1 μM using PBS. Upon completion, unreacted compound is removed by using a PD-10 desalting column (GE Healthcare). To prepare ADC on a larger scale, 11.3 μl of β-lactam-MMAF (10 mM in 100% DMSO) was added to 5.7 mg of antibody for a final reaction volume of 560 μl. The solution was incubated for 4 hours at room temperature and purified as described previously. The conjugates in PBS are stored at 4° C. for short term use and at −80° C. in aliquots for long term use. Antibody concentrations are determined with the Bio-Rad Protein Assay, using a known concentration of an unconjugated antibody as standard.

Cells are plated in 96-well plates at $5\times10^3$ cells per well for all BC cells, except KPL-4 ($3\times10^3$ cells per well). $2.0\times10^4$ cells per well for MM or Ramos cells. BC cells are allowed to adhere overnight and suspension cells are treated immediately. Serial dilutions of unconjugated antibody and ADCs are added to the cells at concentrations ranging from 0 to 10 nM. After incubation for 72 h, the cell viability i measured using the CellTiter 96 AQueous One Solution Cell Proliferation Assay (Promega) following the manufacturer's instructions. The cell viability is calculated as a percentage of untreated cells 100%).

Figure 38:
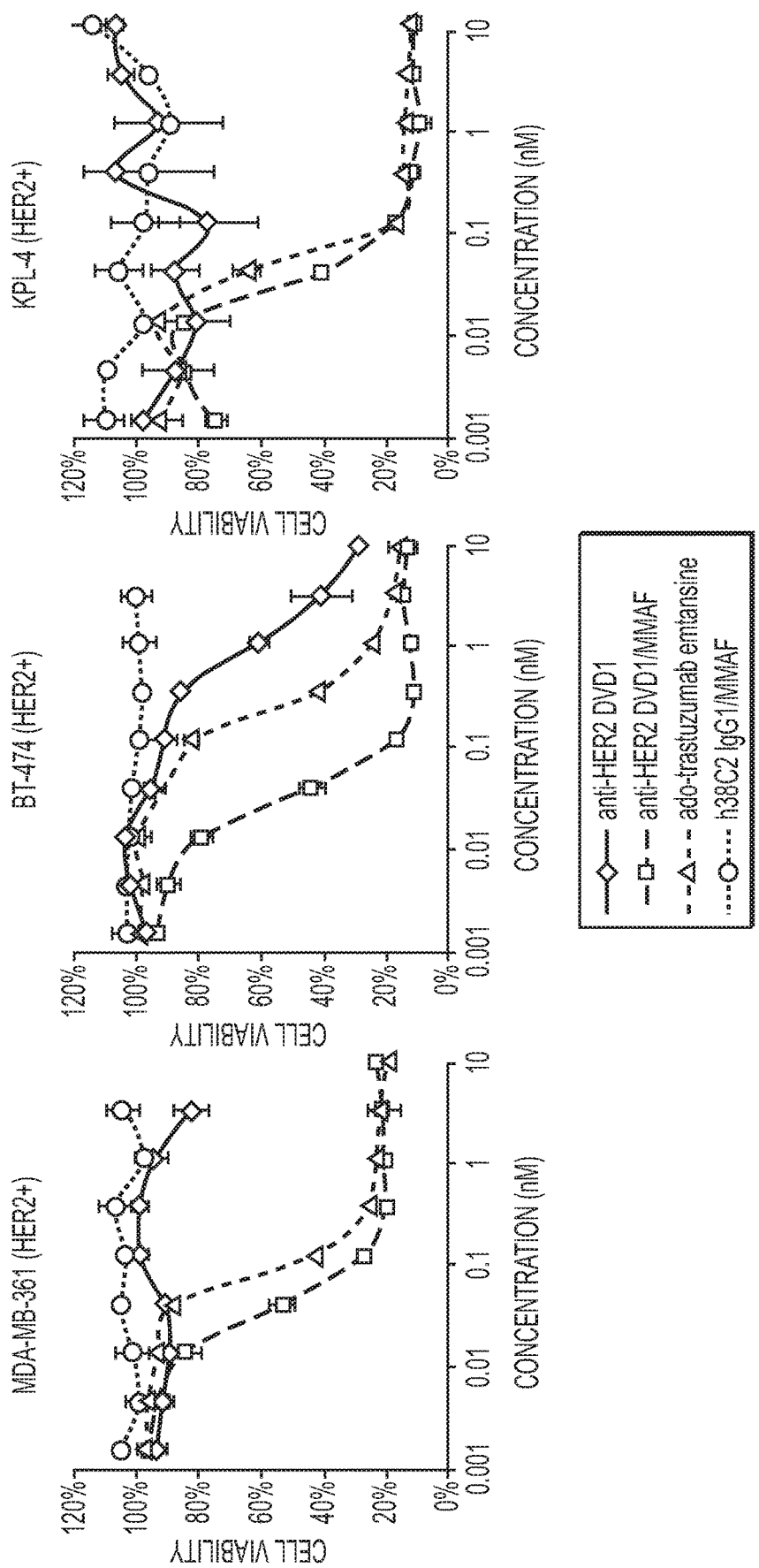
FIG. 38 provides graphical data depicting in vitro activity of anti-HER2 DVD1/MMAF against HER2+ cells.
Figure 39A:
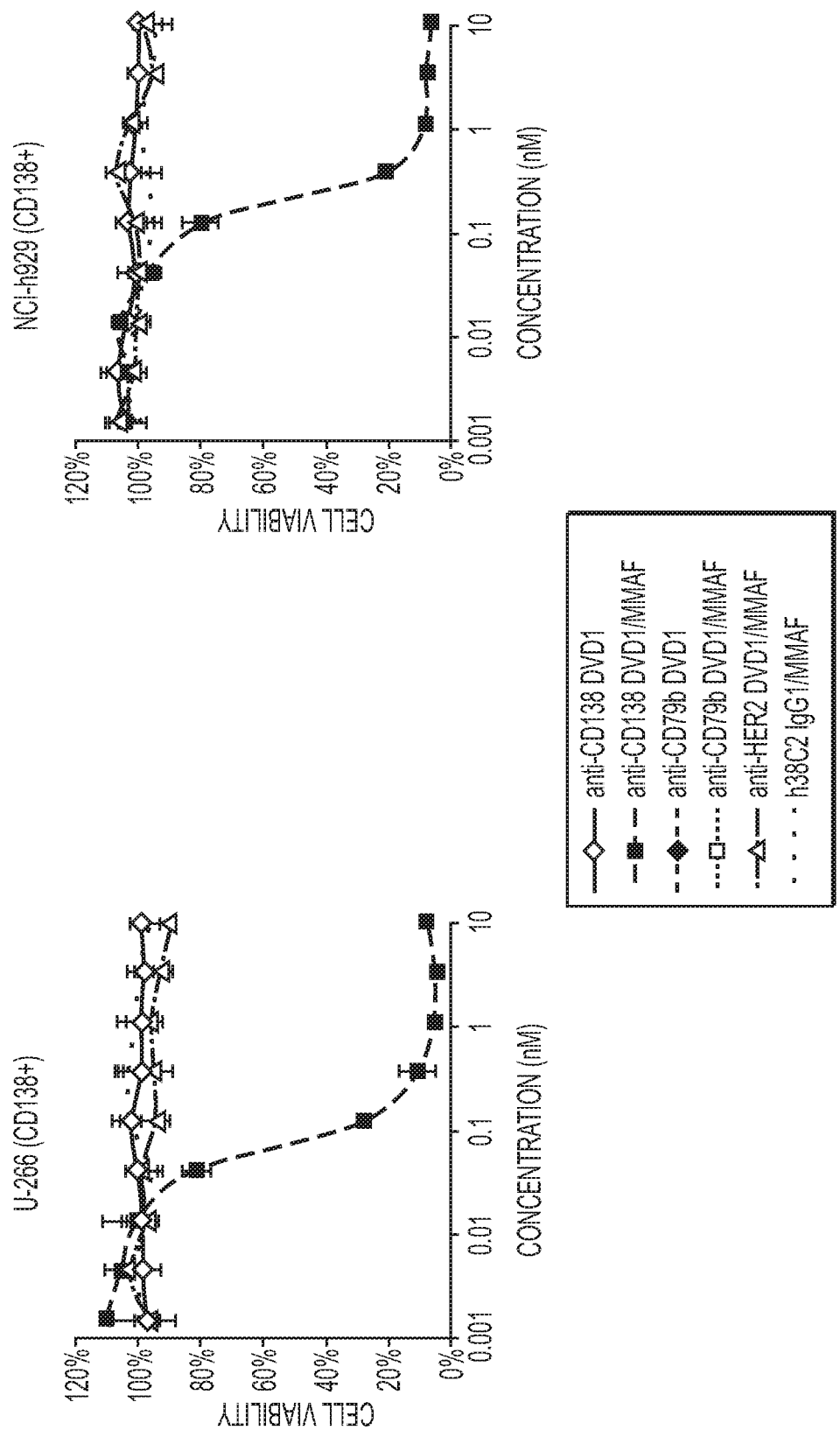
FIG. 39 provides graphical data depicting in vitro activity of anti-CD138 DVD1/MMAF and anti-CD79b DVD1/MMAF.
Figure 39B:
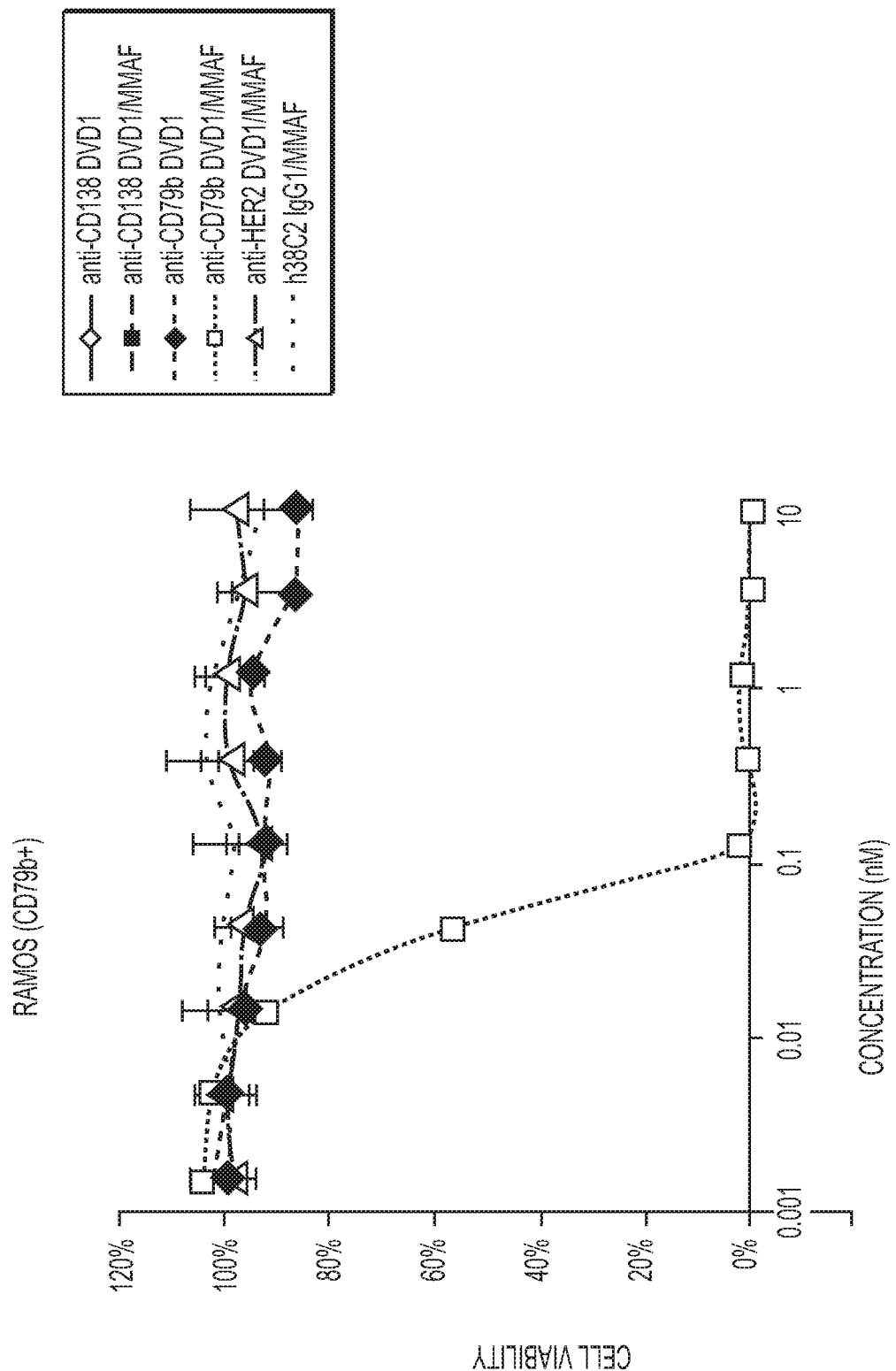

The in vitro cytotoxicity of the conjugate is evaluated against HER2+(SK-BR-3) and HER2-(MDA-MB-468) BC cells. The ADC is highly potent against target expressing cells (IC50=double digit picomolar) with no cytotoxicity observed with the HER2-cell line (FIG. 29: SKBR3 (HER2+) panel). As a negative control h38C2 IgG1 is incubated with β-lactam MMAF in parallel and is tested against these cells lines. Since h38C2 lacks the additional anti-HER2 targeting domain, no cytotoxicity is observed as predicted. The ADC is also found to be highly potent against several other HER2+ cell lines (FIG. 38). Referring to FIG. 38, in vitro cytotoxicity of anti-HER2 DVD1/MMAF following incubation with HER2+BC cell lines MDA-MB-361, BT-474, and KPL-4 for 72 h at 37° C. (mean±SD of triplicates) is depicted. To demonstrate the utility of this strategy, two additional ADCs are also prepared by substituting the HER2 targeting variable domain for a CD138 and CD79b targeting domain. Both of these antigens are clinically established ADC targets for the treatment of multiple myeloma (MM) and non-Hodgkin lymphoma (NHL) Both ADCs are highly potent (IC50=double digit picomolar) against target expressing cells (FIG. 39). Referring to FIG. 39A, cytotoxicity of anti-CD138 DVD1/MMAF conjugate following incubation with CD138+MM cell lines U-266 and NCI-H929 for 72 h at 37° C. (mean±SD of triplicates) is depicted. Referring to FIG. 39B, Cytotoxicity of anti-CD79b DVD1/MMAF conjugate following incubation with CD79b+ Burkitt's Lymphoma cell line (Ramos) for 72 h at 37° C. (mean±SD of triplicates) is depicted. Anti-HER2 DVD1/MMAF and h38C2 IgG1/MMAF are used as negative controls.

Example 20: Analytical Characterization of Anti-HER2 DVD1/MMAF Drug Conjugates

Figure 40A:
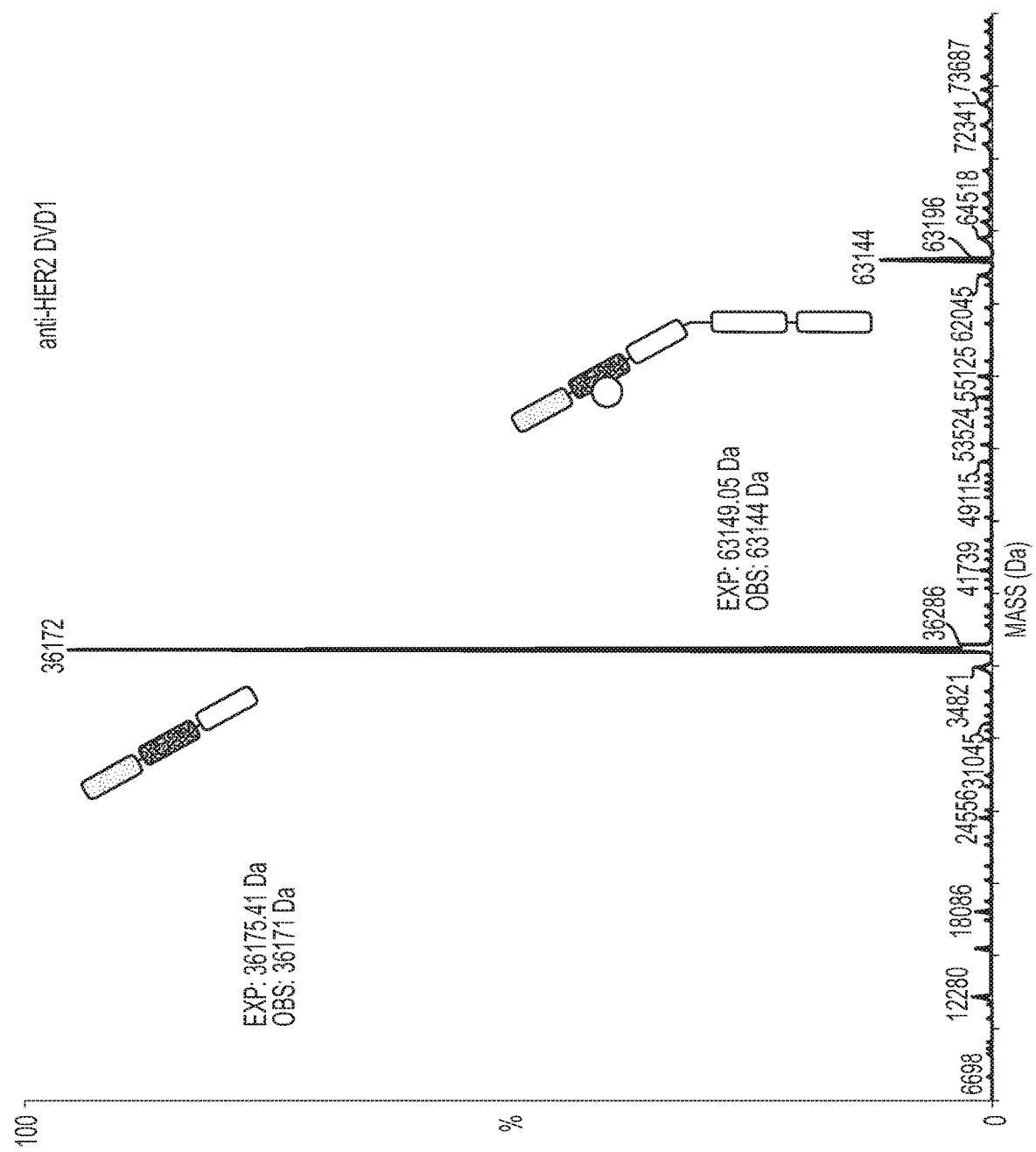
FIG. 40A provides graphical data depicting electrospray ionization time of flight (ESI-TOF) of reduced unconjugated anti-HER2 DVD1.
Figure 40B:
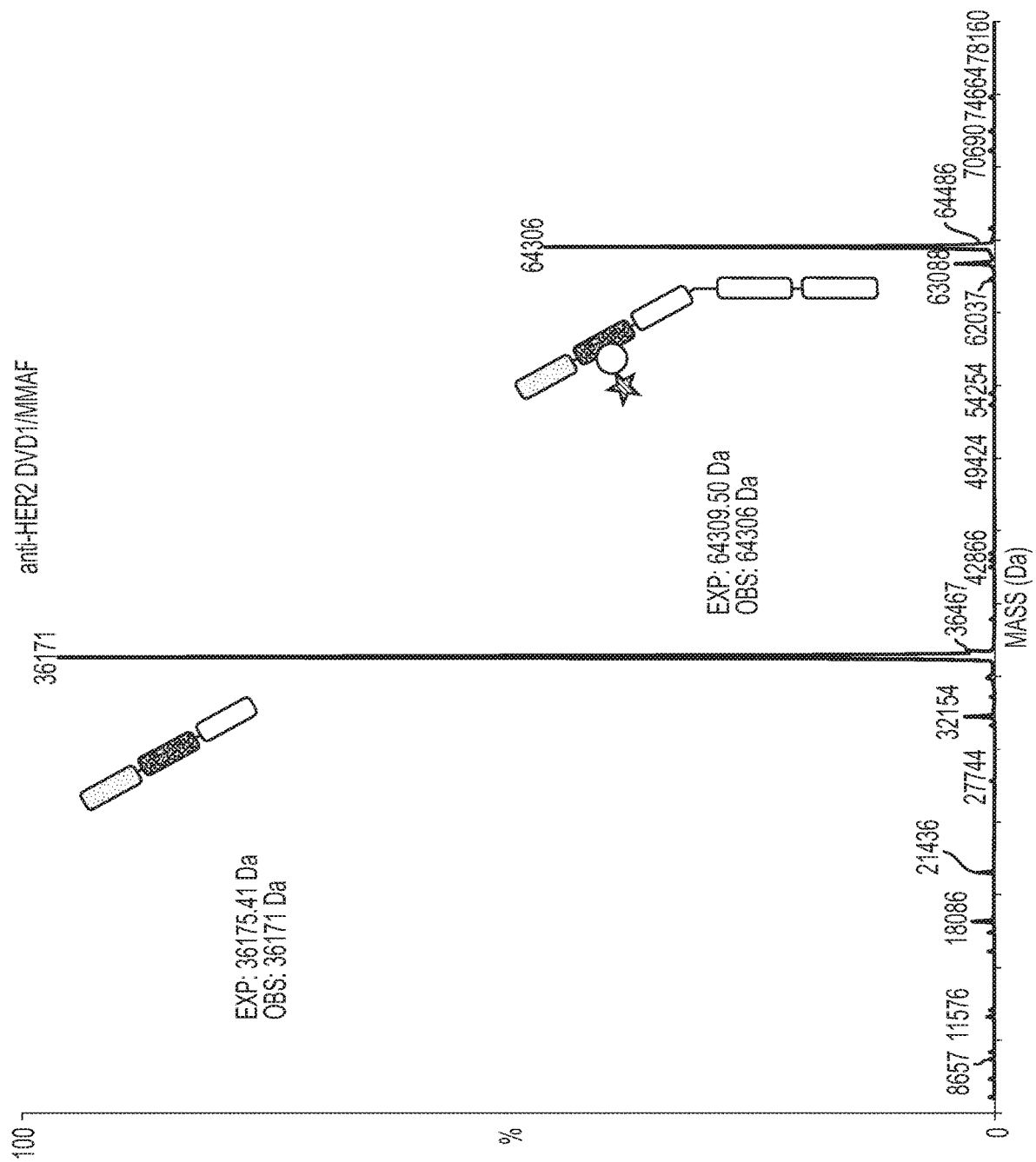
FIG. 40B provides graphical data depicting electrospray ionization time of flight (ESI-TOF) of reduced conjugated anti-HER2 DVD1/MMAF.
Figure 41A:
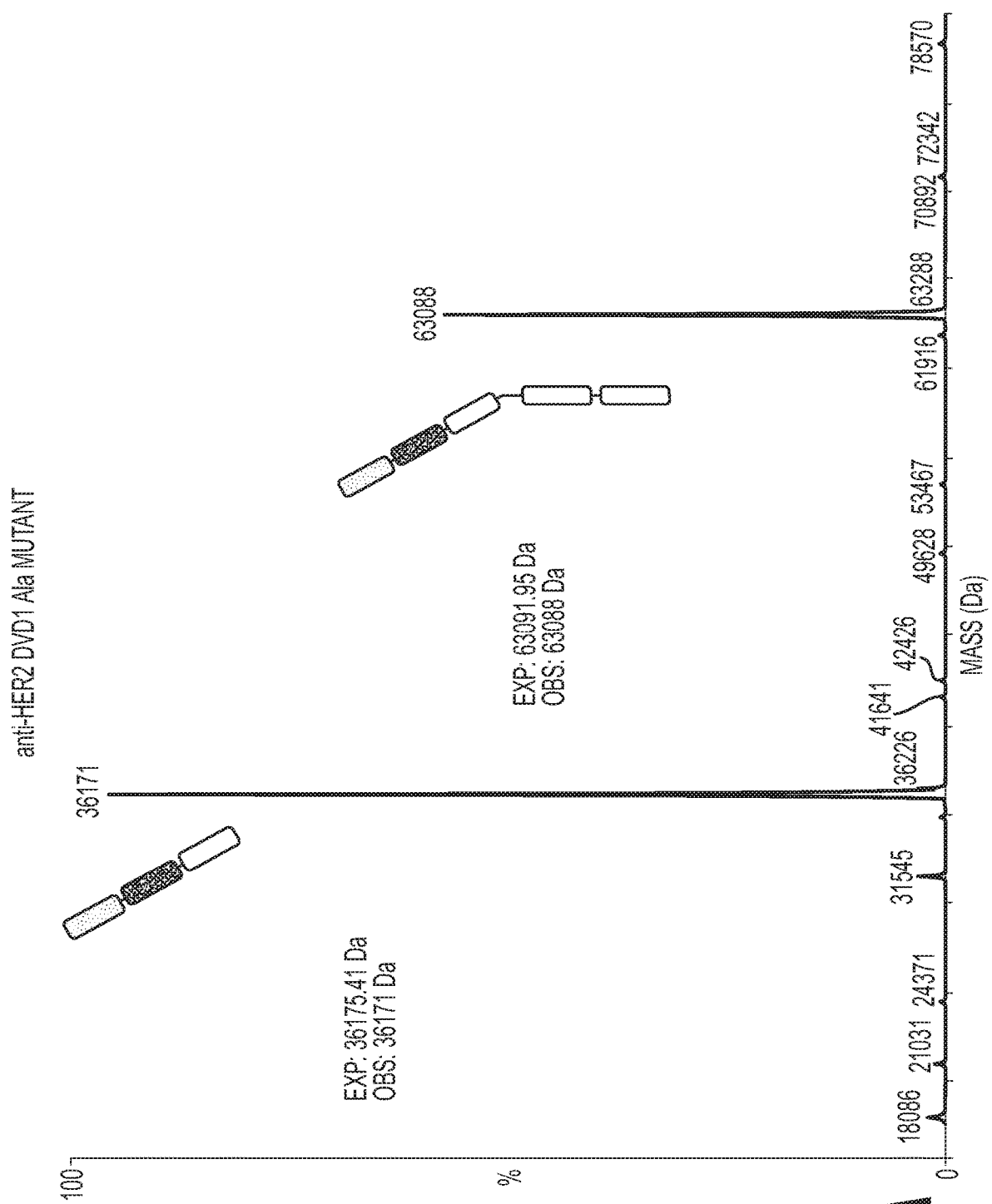
FIG. 41A provides graphical data depicting electrospray ionization time of flight (ESI-TOF) of Alanine mutant of reduced anti-HER2 DVD1 Ala mutant.
Figure 41B:
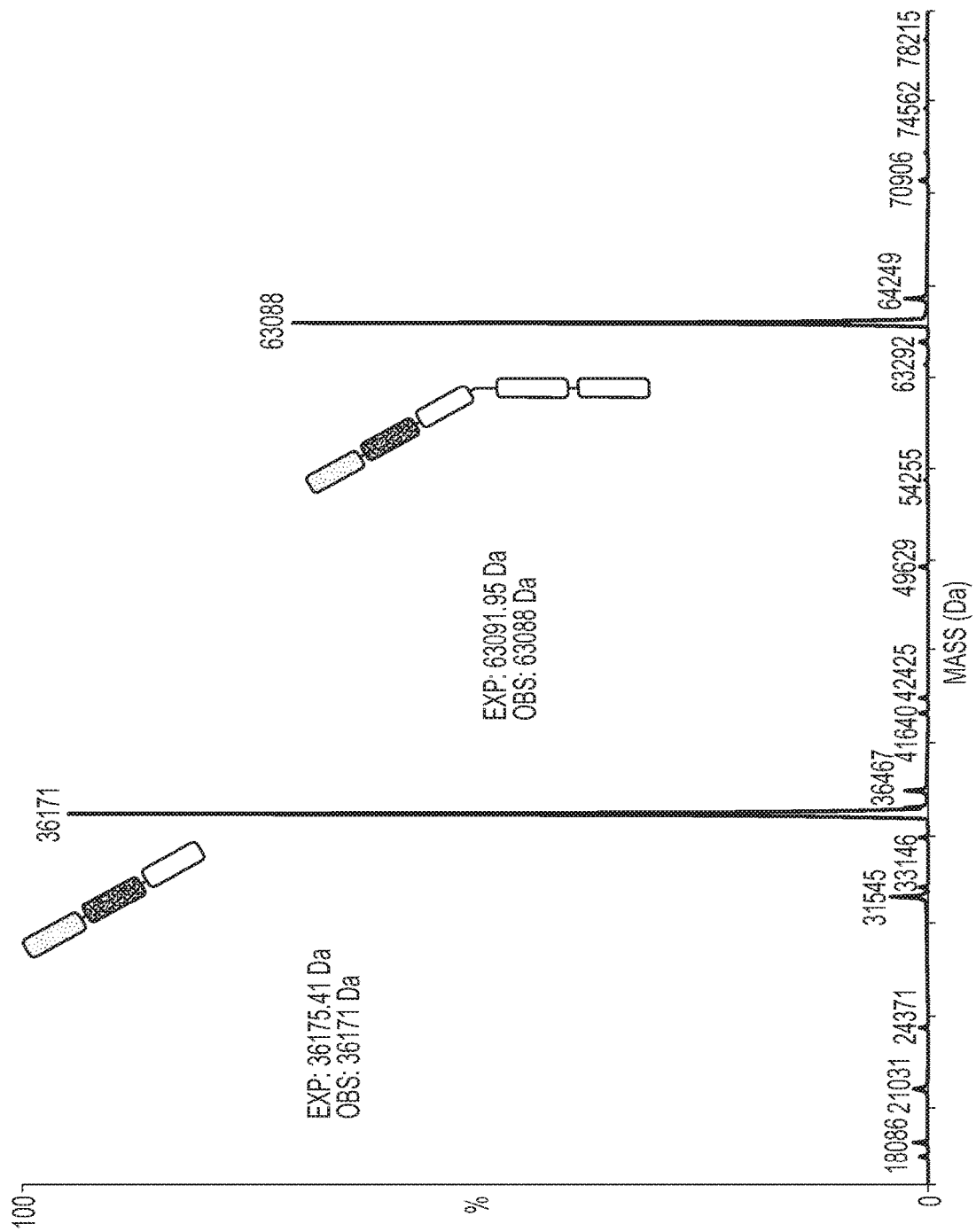
FIG. 41B provides graphical data depicting electrospray ionization time of flight (ESI-TOF) of Alanine mutant of reduced anti-HER2 DVD1/MMAF Ala mutant.

To confirm the drug loading of this ADC platform, mass spectrometry is used to determine the mass of the heavy and light chain. All samples are deglycosylated with PNGase F (New England Biolabs) overnight at 37° C. under reducing conditions (50 mM DTT in PBS). The PNGase F is removed using a Protein G HP SpinTrap (GE Healthcare) according to the manufacturer's instructions. The samples are reduced again prior to sample analysis (10 mM DTT in PBS). Data is obtained on an Agilent Electrospray Ionization Time of Flight (ESI-TOF) mass spectrometer. Deconvoluted masses are obtained using Agilent BioConfirm Software. Since the only lysine expected to react with the β-lactam MMAF drug compound is located on the heavy chain, the mass of the heavy chain should only increase by the addition of one drug compound and no modification should be observed on the light chain. When the mass of unconjugated anti-HER2 DVD1 is compared to the anti-HER2 DVD1/MMAF, the mass increases corresponding to the addition of a single drug molecule with no change in mass detected for the light chain (FIG. 40). Referring to FIG. 40, unconjugated anti-HER2 DVD1 (FIG. 40A) and conjugated anti-HER2 DVD1/MMAF (FIG. 40B) are first deglycosylated with PNGase F and are reduced with 10 mM DTT before analysis. No conjugation is detected on the light chain and the increase in mass of the heavy chain (~1160 Da) corresponds to the addition of β-lactam MMAF. No unconjugated or higher drug loaded species are detected. Thus, the drug to antibody ratio (DAR) is 2 for intact anti-HER2 DVD1/MMAF. No higher drug loaded species are detected. Furthermore, when the Lys is mutated to alanine (Ala) and conjugated in parallel with β-lactam MMAF, no modification is detected (FIG. 41). Referring to FIG. 41, Anti-HER2 DVD1 is mutated to replace the lysine of h38C2 with an alanine and incubated with β-lactam MMAF using the conditions in Example 19. In FIG. 41, unconjugated anti-HER2 DVD1 Ala mutant (FIG. 41A) and conjugated anti-HER2 DVD1/MMAF Ala mutant (FIG. 41B) are first deglycosylated with PNGase F and are reduced with 10 mM DTT before analysis. No conjugation is detected on the light or heavy chain following incubation with β-lactam MMAF indicating the lysine of h38C2 as the drug attachment site. This data combined with the fact that the ADC is no longer catalytically active, strongly suggests that the Lys residue is the only conjugation point. Since the DVD based ADCs are composed of two heavy and light chains, the DAR is therefore 2.

Figures 43A, 43B:
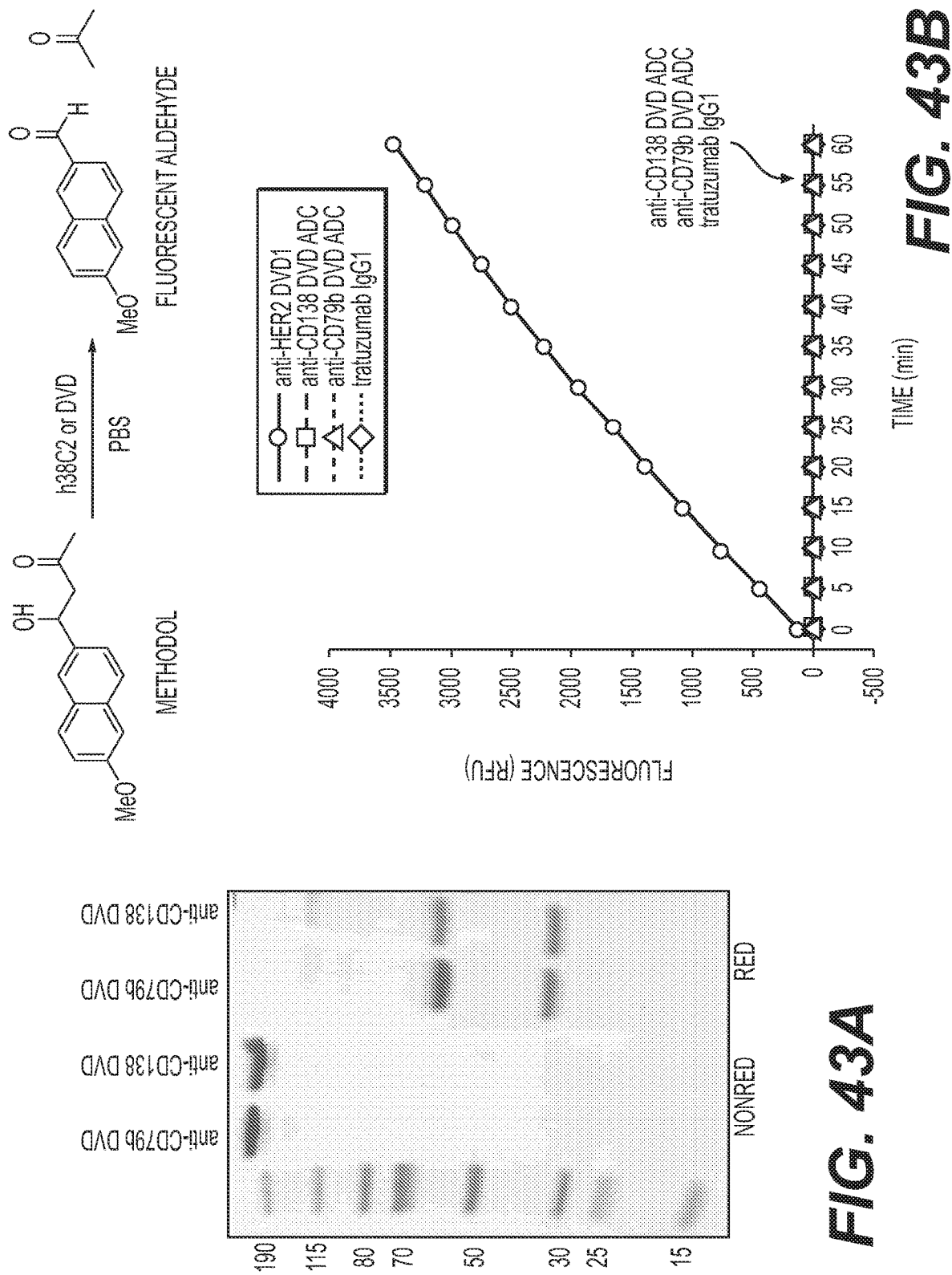
FIG. 43A provides a Coomassie stained SDS-PAGE of both anti-CD138 DVD1 and anti-CD79b DVD1.
FIG. 43B provides graphical data depicting catalytic activity of anti-CD138 DVD1/MMAF and anti-CD79b DVD1/MMAF.

Example 21: Evaluation of Anti-HER2 DVD1/MMAF in a Human Breast Cancer Xenograft Mouse Model Referring to FIG. 43A, Coomassie stained SDS-PAGE confirms the purity of both anti-CD138 DVD1 and anti-CD79b DVD1 under nonreducing (expected=~200 kDa) and reducing conditions (expected heavy chain=~63 kDa, light chain=~36 kDa). Molecular weights from a pre-stained protein ladder are shown on the left. Referring to FIG. 43B, anti-CD138 DVD1 and anti-CD79b DVD1 are incubated with 4 equivalents of β-lactam MMAF as described for the preparation of anti-HER2 DVD1/MMAF. Complete conjugation is confirmed by assessing the catalytic activity of the resulting anti-CD138 DVD1/MMAF and anti-CD79b DVD1/MMAF with unconjugated anti-HER2 DVD1 as a positive control and trastuzumab IgG1 as a negative control. Complete loss of catalytic activity confirms complete conjugation.

The anti-HER2 DVD1/MMAF is evaluated in vivo. BC xenograft studies are conducted using KPL-4 cells with female NSG mice. KPL-4 cells ($6\times10^6$ per mouse) in a 1:1 mixture of PBS and BD Matrigel (BD Bioscience) are inoculated subcutaneously into the mammary fat pad of 7-weeks old female NSG mice (The Jackson Laboratory). When tumors reach ~150 mm$^3$, the mice are randomly assigned to 5 groups of 7-8 mice each and are treated with anti-HER2 DVD1/MMAF at 5 mg/kg or 10 mg/kg, or with unconjugated anti-HER2 DVD1 at 10 mg/kg, or with ado-trastuzumab emtansine biosimilar (Levena Biopharma) at 5 mg/kg, or with vehicle (PBS) alone, by i.v. (tail vein) injection every 4 days for a total of 4 cycles. The mice are predosed with 250 µl of sterile-filtered human serum (Sigma Aldrich) 24 hours before each cycle by i.p. injection. The tumor size is monitored every 4 days using caliper measurement. All procedures are approved by the Institutional Animal Care and Use Committee of The Scripps Research Institute and are performed according to the NIH Guide for the Care and Use of Laboratory Animals.

Figure 42A:
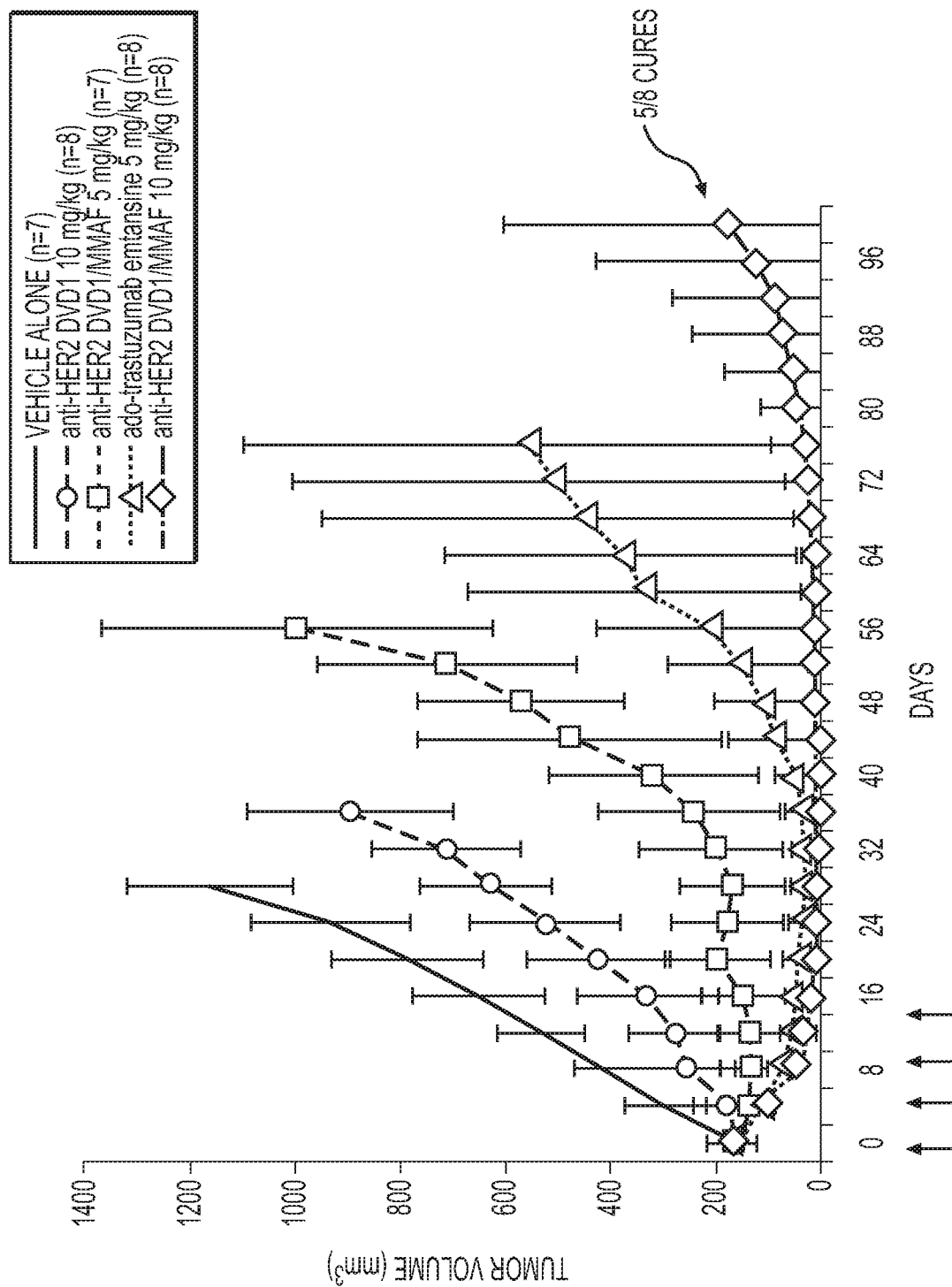
FIG. 42A provides graphical data depicting in vivo activity of the anti-HER2 DVD1/MMAF conjugate as a function of tumor volume.
Figure 42B:
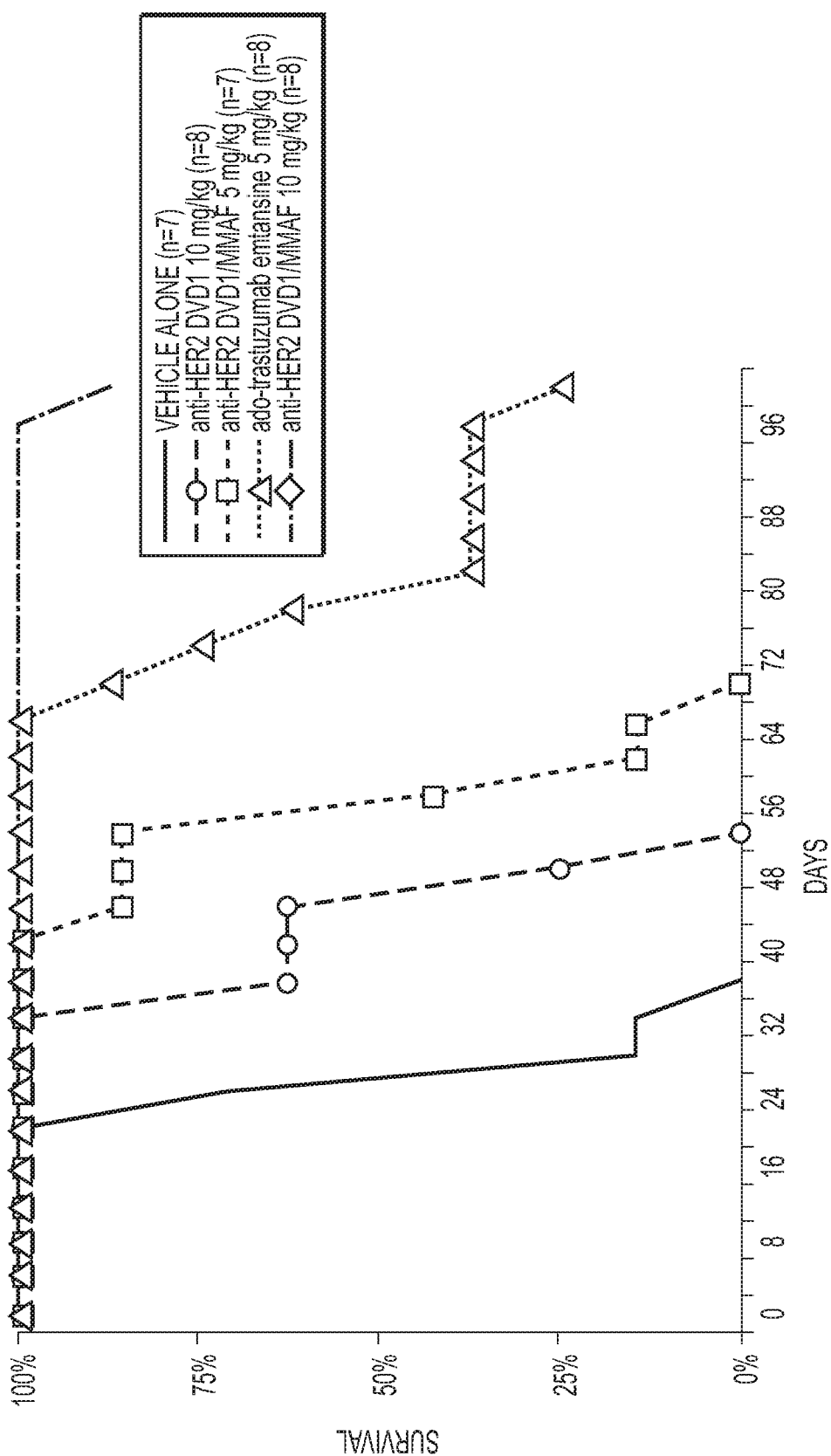
FIG. 42B provides a Kaplan-Meier survival curve depicting in vivo activity of the anti-HER2 DVD1/MMAF conjugate.

Mice bearing established tumors (~150 mm$^3$) are treated every four days with an intravenous (i.v.) injection of 5 mg/kg or 10 mg/kg of anti-HER2 DVD1/MMAF, 10 mg/kg unconjugated anti-HER2 DVD1, the benchmark ADC ado-trastuzumab emtansine at 5 mg/kg, or vehicle for a total of four treatments. Since NSG mice lack serum IgG, each animal is predosed with 250 µl of human serum to prevent clearance of the injected antibodies via macrophages binding to the constant domains. Significant tumor regression and growth inhibition is observed for both anti-HER2 DVD1/MMAF doses (FIG. 42A). Referring to FIG. 42A, human BC cell line KPL-4 is xenografted into the mammary fat pads of female NSG mice, is grown to ~150 mm$^3$, is randomized into 5 groups comprising 7 or 8 mice each, and is treated with i.v. (tail vein) injections of the indicated ADCs and controls four times every four days at the indicated doses. 250 µl of human serum is injected i.p. (peritoneum) 24 hours before each injection. Mean±SD values are plotted. The survival is also significantly longer compared to vehicle for both anti-HER2 DVD1/MMAF doses and unconjugated anti-HER2 DVD groups (FIG. 42B). Furthermore, the 10 mg/kg anti-HER2 DVD ADC group has five out of the eight animal cures at the end of the experiment on day 100, with 7/8 animals surviving. At this dose, both tumor regression and survival are superior to ado-trastuzumab emtansine at 5 mg/kg. Two important considerations when comparing the ADC platform to ado-trastuzumab emtansine are antibody size and drug loading. The ADC platform is 25% larger (200 kDa) than ado-trastuzumab emtansine (150 kDa) and has fewer drugs attached per antibody (2 drugs/antibody) versus (avg 3.5 drugs/antibody) for ado-trastuzumab emtansine. When considering these factors and normalizing to nanomoles of cytotoxic agent per dose, 10 mg/kg of anti-HER2 DVD ADC is effectively a lower dose (~98 nmoles MMAF) when compared to 5 mg/kg ado-trastuzumab emtansine (~114 nmoles mertansine). Despite this higher dose of active drug, no animals are cured using 5 mg/kg ado-trastuzumab emtansine during the course of the study and overall survival was lower with only 2/8 animals surviving at the end of the study.

Example 22: Comparing Catalytic Activity Across Different DVDs

Figure 45:
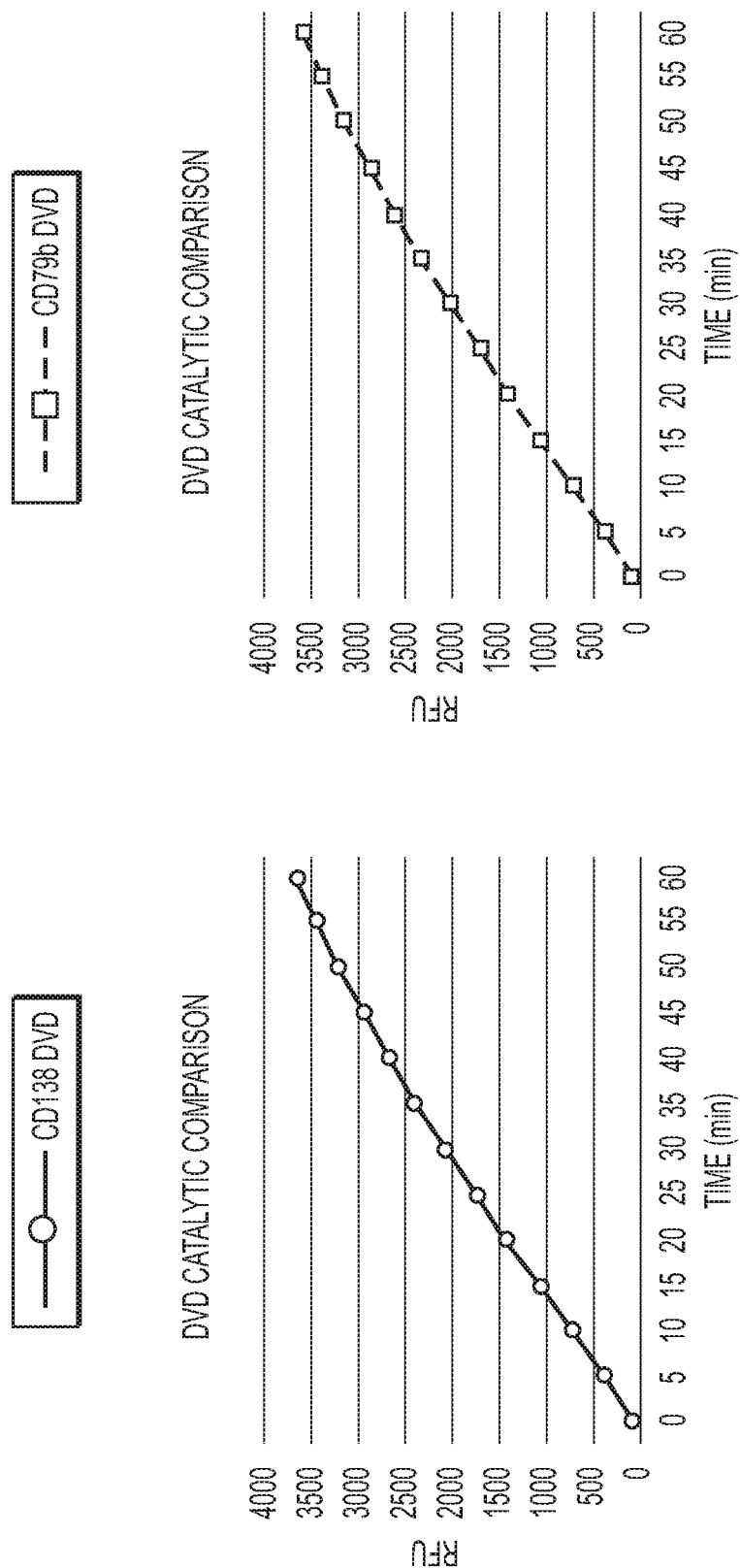
FIG. 45 provides graphical data depicting that all DVDs have essentially identical catalytic activity to parent h38C2 IgG1.
Figure 45:
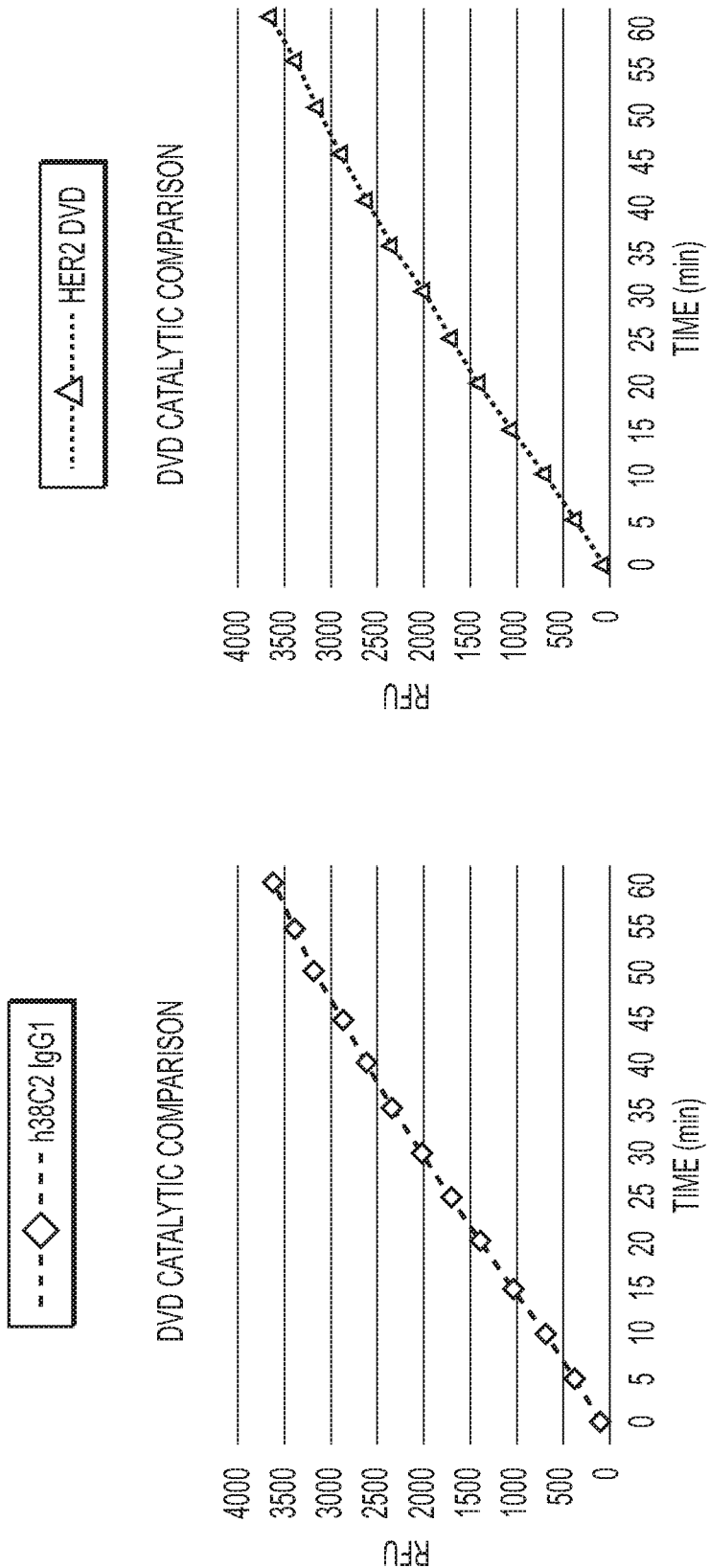

The catalytic activity across CD138 DVD, CD79b DVD, h38C2 IgG1, and HER2 DVD2 are compared using the catalytic activity provided above in Example 18. Referring to FIG. 45, all the tested DVDs have essentially identical catalytic activity to parent h38C2 IgG1. This suggests that the h38C2 Fv portion is a universal adaptor for site-specific drug conjugation independent of the upstream targeting Fv portion.

Figure 46:
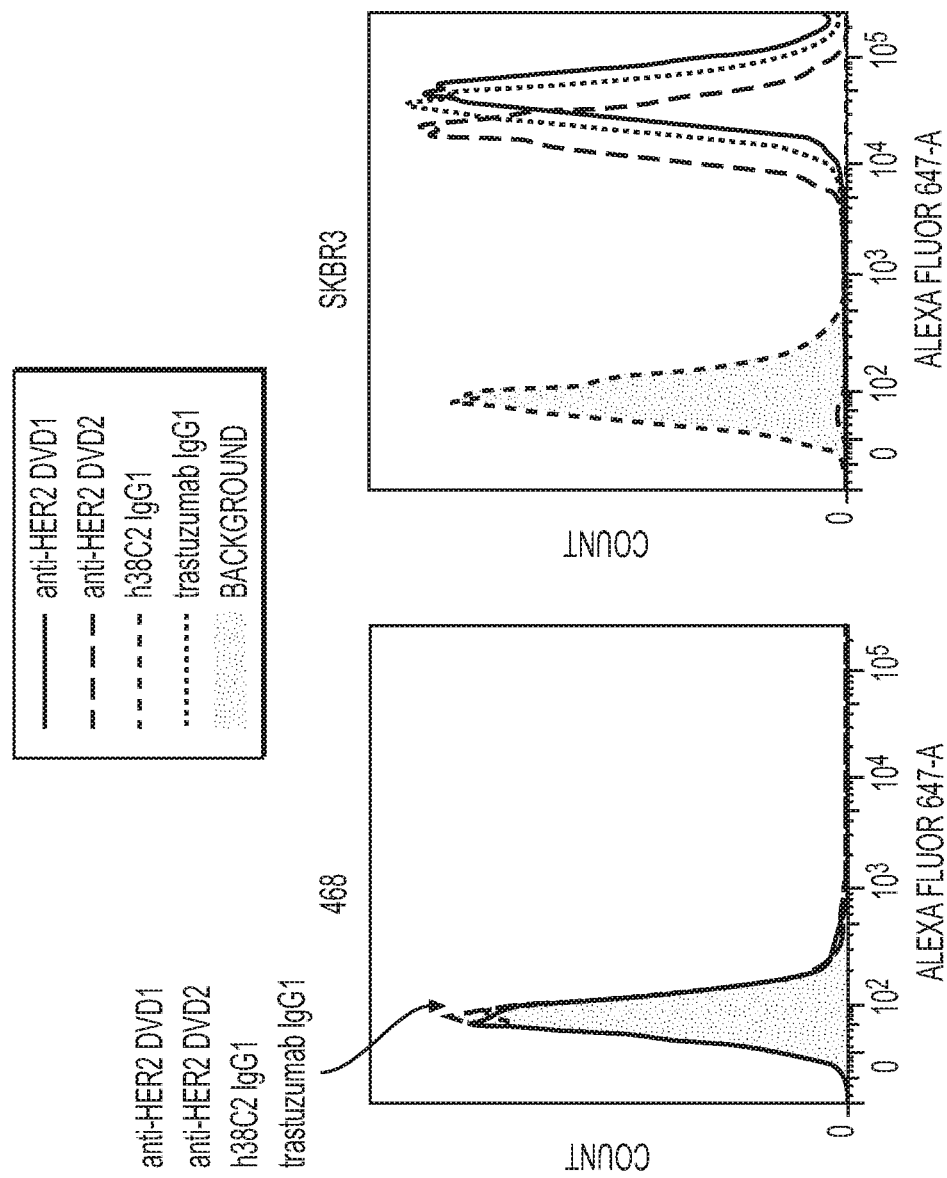
FIG. 46 provides flow cytometry data indicating the binding of all DVDs against target expressing cells.
Figure 46:
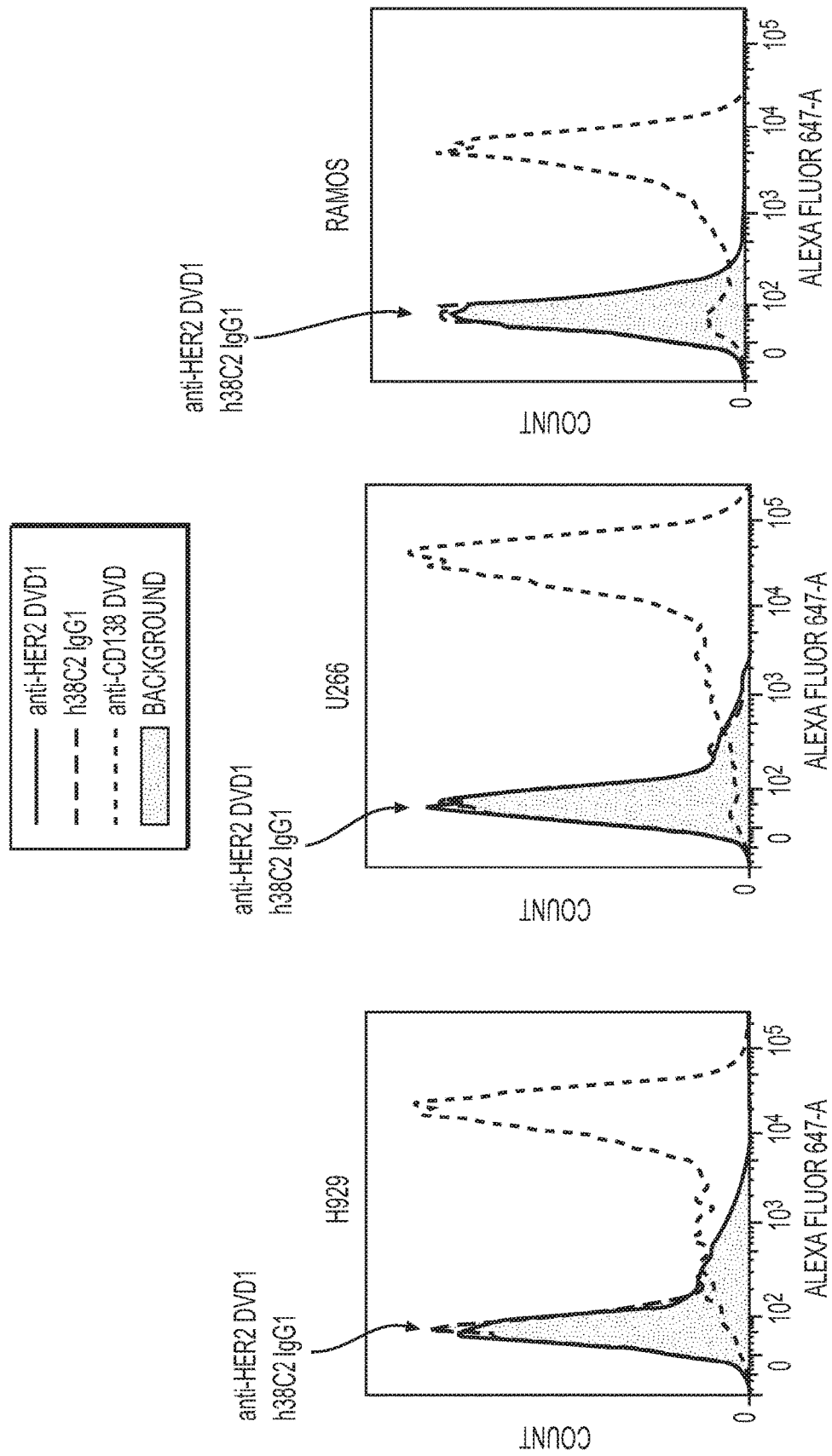

The binding activities of these DVDs are also tested against target expressing cells. SK-BR-3, MDA-MB-468, H929, U266, and Ramos cells are harvested using TrypLE (Life Technologies) and dispensed in a V-bottom 96-well plate (Corning). The cells are washed with 200 µL flow cytometry buffer (PBS, 2% (w/v) FBS, pH 7.4), are incubated with DVD1 or DVD2 for 30 min on ice, are washed with 200 µL flow cytometry buffer, and are stained with 647 conjugated polyclonal (Fab')$_2$ donkey anti-human Fc (Jackson ImmunoResearch Laboratories) for 20 min on ice. After washing twice with 200 µL ice-cold flow cytometry buffer, the cells are analyzed using a Canto II Flow Cytometer (Becton-Dickinson). Data were analyzed using FlowJo software (Tree Star). Referring to FIG. 46, flow cytometry data indicate the binding of all DVDs against target expressing cells.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. An immunoconjugate having the formula Ig-(L-D)$_n$, wherein:
   (a) Ig is a dual variable domain immunoglobulin molecule, or an antigen-binding fragment thereof, wherein the dual variable domain immunoglobulin molecule comprises:
   (i) a first variable domain that binds to a binding target; and
   (ii) a second variable domain that comprises the variable domain of a humanized catalytic antibody 38C2 (h38C2);
   wherein the first variable domain of Ig is positioned closer to an N-terminus than the second variable domain;
   (b) L is a linker that is covalently conjugated to the reactive lysine residue of h38C2;
   (c) D is a drug moiety; and
   (d) n is selected from an integer from 1 to 12.

2. The immunoconjugate according to claim 1, wherein n is 1 or 2.

3. The immunoconjugate according to claim 1, wherein D comprises 2 or more of the same or different drug moieties.

4. The immunoconjugate according to claim 1, wherein the first variable domain is a Fab or a Fv.

5. The immunoconjugate according to claim 1, wherein the Ig comprises a chimeric immunoglobulin sequence, a humanized immunoglobulin sequence, or a human immunoglobulin sequence.

6. The immunoconjugate according to claim 1, wherein the second variable domain of Ig comprises the amino acid sequence of SEQ ID NO: 3 and SEQ ID NO:4.

7. The immunoconjugate according to claim 1, wherein the binding target is a tumor cell surface antigen.

8. The immunoconjugate according to claim 7, wherein the tumor cell surface antigen is selected from HER2, FOLR1, CD138 and CD79b.

9. The immunoconjugate according to claim 8, wherein the first variable domain of Ig binds to HER2, FLOR1, CD138, or CD79b.

10. The immunoconjugate according to claim 1, wherein the drug moiety is a cytotoxic agent.

11. The immunoconjugate according to claim 10, wherein the cytotoxic agent is selected from a toxin, a chemotherapeutic agent, an antibiotic, a radioactive isotope, a chelated radioactive isotope and a nucleolytic enzyme.

12. The immunoconjugate according to claim 1, wherein D is an auristatin, a dolostatin, a cemadotin, a camptothecin, a maytansinoid, a pyrrolobenzodiazepine (PBD), an enediyne, a doxorubicin, or an siRNA.

13. The immunoconjugate according to claim 1, wherein L is a reversible linker, an irreversible linker, a cleavable linker, a non-cleavable linker, a branched linker or a linear linker.

14. A pharmaceutical composition for the treatment of cancer, wherein the pharmaceutical composition comprises an effective amount of the immunoconjugate according to claim 1 and a pharmaceutically acceptable carrier.

15. A method for treating cancer in a subject, comprising administering to the subject the pharmaceutical composition of claim 14.

16. The immunoconjugate according to claim 12, wherein:
   (a) Ig comprises (1) the amino acid sequences of SEQ ID NOs: 5 and 6 and the binding target of the first variable domain is HER2; (2) the amino acid sequences of SEQ ID NOs: 7 and 8 and the binding target of the first variable domain is HER2; (3) the amino acid sequences of SEQ ID NOs: 9 and 10 and the binding target of the first variable domain is FOLR1; (4) the amino acid sequences of SEQ ID NOs: 11 and 12 and the binding target of the first variable domain is FOLR1; (5) the amino acid sequences of SEQ ID NOs: 13 and 14 and the binding target of the first variable domain is FOLR1; (6) the amino acid sequences of SEQ ID NOs: 15 and 16 and the binding target of the first variable domain is FOLR1; (7) the amino acid sequences of SEQ ID NOs: 17 and 18 and the binding target of the first variable domain is CD 138; (8) the amino acid sequences of SEQ ID NOs: 19 and 20 and the binding target of the first variable domain is CD138; (9) the amino acid sequences of SEQ ID NOs: 21 and 22 and the binding target of the first variable domain is CD79b; or (10) the amino acid sequences of SEQ ID NOs: 23 and 24 and the binding target of the first variable domain is CD79b;
   (b) L is a linear, irreversible linker that is covalently conjugated to the reactive lysine residue of Ig;
   (c) D is MMAF; and
   (d) n is 1 to 12.

17. The immunoconjugate according to claim 16, wherein n is 1 or 2.

18. The method of claim 15, wherein the cancer is a hematological cancer, a carcinoma, a sarcoma, a melanoma, or a central nervous system cancer.

19. The method of claim 15, further administering to the subject an effective amount of a second therapeutic agent.

20. The method of claim 19, wherein the second therapeutic agent is an antibody, an anti-neoplastic agent, a cytotoxic agent, an anti-angiogenic agent, or an immunosuppressive agent.

21. The method of claim 20, wherein the second therapeutic agent is selected from the group consisting of cisplatin, carboplatin, oxaliplatin, mechlorethamine, cyclophosphamide, chlorambucil, ifosfamide, doxorubicin, daunorubicin, valrubicin, idarubicin, epirubicin, actinomycin, bleomycin, plicamycin, mitomycin, bevacizumab, imatinib, erlotinib, gefitinib, ibrutinib, idelalisib, lenalidomide, vincristine, vinblastine, vinorelbine, vindesine, paclitaxel, and docetaxel.

* * * * *